US008937408B2

(12) United States Patent
Ganem et al.

(10) Patent No.: US 8,937,408 B2
(45) Date of Patent: Jan. 20, 2015

(54) WIRELESS ENERGY TRANSFER FOR MEDICAL APPLICATIONS

(75) Inventors: Steven J. Ganem, Westwood, MA (US); Morris P. Kesler, Bedford, MA (US); Katherine L. Hall, Westford, MA (US); David A. Schatz, Needham, MA (US)

(73) Assignee: WiTricity Corporation, Watertown, MA (US)

( * ) Notice: Subject to any disclaimer, the term of this patent is extended or adjusted under 35 U.S.C. 154(b) by 409 days.

(21) Appl. No.: 13/090,369

(22) Filed: Apr. 20, 2011

(65) Prior Publication Data

US 2012/0139355 A1    Jun. 7, 2012

Related U.S. Application Data

(63) Continuation-in-part of application No. 13/021,965, filed on Feb. 7, 2011, which is a continuation-in-part of application No. 12/986,018, filed on Jan. 6, 2011, now Pat. No. 8,643,326, and a continuation-in-part of application No. 12/789,611, filed on May 28, 2010, (Continued)

(51) Int. Cl.
| | |
|---|---|
| *H01F 37/00* | (2006.01) |
| *H01F 38/00* | (2006.01) |
| *H03H 7/40* | (2006.01) |
| *A61B 19/00* | (2006.01) |
| *H02J 5/00* | (2006.01) |
| *H02J 7/02* | (2006.01) |
| *A61B 17/00* | (2006.01) |

(52) U.S. Cl.
CPC ....... *H02J 7/025* (2013.01); *A61B 2017/00367* (2013.01); *H03H 7/40* (2013.01); *A61B 19/2203* (2013.01); *A61B 2017/00221* (2013.01); *H02J 5/005* (2013.01)
USPC .......................................................... 307/104

(58) Field of Classification Search
USPC .......................................................... 307/104
See application file for complete search history.

(56) References Cited

U.S. PATENT DOCUMENTS

| | | | |
|---|---|---|---|
| 645,576 | A | 3/1900 | Tesla |
| 649,621 | A | 5/1900 | Tesla |
| 787,412 | A | 4/1905 | Tesla |
| 1,119,732 | A | 12/1914 | Tesla |
| 2,133,494 | A | 10/1938 | Waters |
| 2,947,957 | A | 8/1960 | Spindler |
| 3,517,350 | A | 6/1970 | Beaver |
| 3,535,543 | A | 10/1970 | Dailey |

(Continued)

FOREIGN PATENT DOCUMENTS

| | | |
|---|---|---|
| CA | 142352 | 8/1912 |
| CN | 102239633 A | 11/2011 |

(Continued)

OTHER PUBLICATIONS

Extended European Search Report for 11184066.6 mailed Mar. 28, 2013, Massachusetts Institute of Technology, 7 pages.

(Continued)

*Primary Examiner* — Hal Kaplan
(74) *Attorney, Agent, or Firm* — Fish & Richardson P.C.

(57) ABSTRACT

Described herein are improved configurations for a wireless power transfer. Described are methods and designs for medical environments and devices. Wireless energy transfer is utilized to eliminate cords and power cables from operating instruments and electronic equipment requiring mobility.

18 Claims, 23 Drawing Sheets

Related U.S. Application Data now Pat. No. 8,598,743, which is a continuation-in-part of application No. 12/770,137, filed on Apr. 29, 2010, and a continuation-in-part of application No. 12/767,633, filed on Apr. 26, 2010, now Pat. No. 8,497,601, and a continuation-in-part of application No. 12/759,047, filed on Apr. 13, 2010, which is a continuation-in-part of application No. 12/757,716, filed on Apr. 9, 2010, which is a continuation-in-part of application No. 12/749,571, filed on Mar. 30, 2010, now Pat. No. 8,692,412, which is a continuation-in-part of application No. 12/639,489, filed on Dec. 16, 2009, now Pat. No. 8,410,636, and a continuation-in-part of application No. 12/647,705, filed on Dec. 28, 2009, now Pat. No. 8,482,158, and a continuation-in-part of application No. 12/567,716, filed on Sep. 25, 2009, now Pat. No. 8,461,719, said application No. 12/757,716 is a continuation-in-part of application No. 12/721,118, filed on Mar. 10, 2010, now Pat. No. 8,723,366, which is a continuation-in-part of application No. 12/705,582, filed on Feb. 13, 2010.

(60) Provisional application No. 61/326,051, filed on Apr. 20, 2010, provisional application No. 61/292,768, filed on Jan. 6, 2010, provisional application No. 61/173,747, filed on Apr. 29, 2009, provisional application No. 61/172,633, filed on Apr. 24, 2009, provisional application No. 61/100,721, filed on Sep. 27, 2008, provisional application No. 61/108,743, filed on Oct. 27, 2008, provisional application No. 61/147,386, filed on Jan. 26, 2009, provisional application No. 61/152,086, filed on Feb. 12, 2009, provisional application No. 61/178,508, filed on May 15, 2009, provisional application No. 61/182,768, filed on Jun. 1, 2009, provisional application No. 61/121,159, filed on Dec. 9, 2008, provisional application No. 61/142,977, filed on Jan. 7, 2009, provisional application No. 61/142,885, filed on Jan. 6, 2009, provisional application No. 61/142,796, filed on Jan. 6, 2009, provisional application No. 61/142,889, filed on Jan. 6, 2009, provisional application No. 61/142,880, filed on Jan. 6, 2009, provisional application No. 61/142,818, filed on Jan. 6, 2009, provisional application No. 61/142,887, filed on Jan. 6, 2009, provisional application No. 61/156,764, filed on Mar. 2, 2009, provisional application No. 61/143,058, filed on Jan. 7, 2009, provisional application No. 61/163,695, filed on Mar. 26, 2009, provisional application No. 61/169,240, filed on Apr. 14, 2009, provisional application No. 61/152,390, filed on Feb. 13, 2009.

(56) References Cited

U.S. PATENT DOCUMENTS

| | | | |
|---|---|---|---|
| 3,780,425 | A | 12/1973 | Penn et al. |
| 3,810,303 | A | 5/1974 | Hoell |
| 3,871,176 | A | 3/1975 | Schukei |
| 4,088,999 | A | 5/1978 | Fletcher et al. |
| 4,095,998 | A | 6/1978 | Hanson |
| 4,180,795 | A | 12/1979 | Matsuda et al. |
| 4,280,129 | A | 7/1981 | Wells |
| 4,450,431 | A | 5/1984 | Hochstein |
| 4,577,175 | A | 3/1986 | Burgher et al. |
| 4,588,978 | A | 5/1986 | Allen |
| 5,027,709 | A | 7/1991 | Slagle |
| 5,033,295 | A | 7/1991 | Schmid et al. |
| 5,034,658 | A | 7/1991 | Hierig et al. |
| 5,053,774 | A | 10/1991 | Schuermann et al. |
| 5,070,293 | A | 12/1991 | Ishii et al. |
| 5,118,997 | A | 6/1992 | El-hamamsy |
| 5,216,402 | A | 6/1993 | Carosa |
| 5,229,652 | A | 7/1993 | Hough |
| 5,287,112 | A | 2/1994 | Schuermann |
| 5,341,083 | A | 8/1994 | Klontz et al. |
| 5,367,242 | A | 11/1994 | Hulman |
| 5,374,930 | A | 12/1994 | Schuermann |
| 5,408,209 | A | 4/1995 | Tanzer et al. |
| 5,437,057 | A | 7/1995 | Richley et al. |
| 5,455,467 | A | 10/1995 | Young et al. |
| 5,493,691 | A | 2/1996 | Barrett |
| 5,522,856 | A | 6/1996 | Reineman |
| 5,528,113 | A | 6/1996 | Boys et al. |
| 5,541,604 | A | 7/1996 | Meier |
| 5,550,452 | A | 8/1996 | Shirai et al. |
| 5,565,763 | A | 10/1996 | Arrendale et al. |
| 5,630,835 | A | 5/1997 | Brownlee |
| 5,697,956 | A | 12/1997 | Bornzin |
| 5,703,461 | A | 12/1997 | Minoshima et al. |
| 5,703,573 | A | 12/1997 | Fujimoto et al. |
| 5,710,413 | A | 1/1998 | King et al. |
| 5,742,471 | A | 4/1998 | Barbee, Jr. et al. |
| 5,821,728 | A | 10/1998 | Schwind |
| 5,821,731 | A | 10/1998 | Kuki et al. |
| 5,864,323 | A | 1/1999 | Berthon |
| 5,898,579 | A | 4/1999 | Boys et al. |
| 5,903,134 | A | 5/1999 | Takeuchi |
| 5,923,544 | A | 7/1999 | Urano |
| 5,940,509 | A | 8/1999 | Jovanovich et al. |
| 5,957,956 | A | 9/1999 | Kroll et al. |
| 5,959,245 | A | 9/1999 | Moe et al. |
| 5,986,895 | A | 11/1999 | Stewart et al. |
| 5,993,996 | A | 11/1999 | Firsich |
| 5,999,308 | A | 12/1999 | Nelson et al. |
| 6,012,659 | A | 1/2000 | Nakazawa et al. |
| 6,047,214 | A | 4/2000 | Mueller et al. |
| 6,057,668 | A | 5/2000 | Chao |
| 6,066,163 | A | 5/2000 | John |
| 6,067,473 | A | 5/2000 | Greeninger et al. |
| 6,108,579 | A | 8/2000 | Snell et al. |
| 6,127,799 | A | 10/2000 | Krishnan |
| 6,176,433 | B1 | 1/2001 | Uesaka et al. |
| 6,184,651 | B1 | 2/2001 | Fernandez et al. |
| 6,207,887 | B1 | 3/2001 | Bass et al. |
| 6,232,841 | B1 | 5/2001 | Bartlett et al. |
| 6,238,387 | B1 | 5/2001 | Miller, III |
| 6,252,762 | B1 | 6/2001 | Amatucci |
| 6,356,773 | B1 | 3/2002 | Rinot |
| 6,406,168 | B1 | 6/2002 | Whiting |
| 6,436,299 | B1 | 8/2002 | Baarman et al. |
| 6,450,946 | B1 | 9/2002 | Forsell |
| 6,452,465 | B1 | 9/2002 | Brown et al. |
| 6,459,218 | B2 | 10/2002 | Boys et al. |
| 6,473,028 | B1 | 10/2002 | Luc |
| 6,483,202 | B1 | 11/2002 | Bozs |
| 6,515,878 | B1 | 2/2003 | Meins et al. |
| 6,535,133 | B2 | 3/2003 | Gohara |
| 6,561,975 | B1 | 5/2003 | Pool et al. |
| 6,563,425 | B2 | 5/2003 | Nicholson et al. |
| 6,597,076 | B2 | 7/2003 | Scheible et al. |
| 6,609,023 | B1 | 8/2003 | Fischell et al. |
| 6,631,072 | B1 | 10/2003 | Paul et al. |
| 6,650,227 | B1 | 11/2003 | Bradin |
| 6,664,770 | B1 | 12/2003 | Bartels |
| 6,673,250 | B2 | 1/2004 | Kuennen et al. |
| 6,683,256 | B2 | 1/2004 | Kao |
| 6,696,647 | B2 | 2/2004 | Ono et al. |
| 6,703,921 | B1 | 3/2004 | Wuidart et al. |
| 6,731,071 | B2 | 5/2004 | Baarman |
| 6,749,119 | B2 | 6/2004 | Scheible et al. |
| 6,772,011 | B2 | 8/2004 | Dolgin |
| 6,798,716 | B1 | 9/2004 | Charych |
| 6,803,744 | B1 | 10/2004 | Sabo |
| 6,806,649 | B2 | 10/2004 | Mollema et al. |
| 6,812,645 | B2 | 11/2004 | Baarman |
| 6,825,620 | B2 | 11/2004 | Kuennen et al. |
| 6,831,417 | B2 | 12/2004 | Baarman |

(56) References Cited

U.S. PATENT DOCUMENTS

| | | | |
|---|---|---|---|
| 6,839,035 B1 | 1/2005 | Addonisio et al. |
| 6,844,702 B2 | 1/2005 | Giannopoulos et al. |
| 6,856,291 B2 | 2/2005 | Mickle et al. |
| 6,858,970 B2 | 2/2005 | Malkin et al. |
| 6,906,495 B2 | 6/2005 | Cheng et al. |
| 6,917,163 B2 | 7/2005 | Baarman |
| 6,917,431 B2 | 7/2005 | Soljacic et al. |
| 6,937,130 B2 | 8/2005 | Scheible |
| 6,960,968 B2 | 11/2005 | Odendaal et al. |
| 6,961,619 B2 | 11/2005 | Casey |
| 6,967,462 B1 | 11/2005 | Landis |
| 6,975,198 B2 | 12/2005 | Baarman et al. |
| 6,988,026 B2 | 1/2006 | Breed et al. |
| 7,027,311 B2 | 4/2006 | Vanderelli et al. |
| 7,035,076 B1 | 4/2006 | Stevenson |
| 7,042,196 B2 | 5/2006 | Ka-Lai et al. |
| 7,069,064 B2 | 6/2006 | Gevorgian et al. |
| 7,076,206 B2 | 7/2006 | Elferich et al. |
| 7,084,605 B2 | 8/2006 | Mickle et al. |
| 7,116,200 B2 | 10/2006 | Baarman et al. |
| 7,118,240 B2 | 10/2006 | Baarman et al. |
| 7,126,450 B2 | 10/2006 | Baarman et al. |
| 7,127,293 B2 | 10/2006 | MacDonald |
| 7,132,918 B2 | 11/2006 | Baarman et al. |
| 7,147,604 B1 | 12/2006 | Allen et al. |
| 7,180,248 B2 | 2/2007 | Kuennen et al. |
| 7,191,007 B2 | 3/2007 | Desai et al. |
| 7,193,418 B2 | 3/2007 | Freytag |
| D541,322 S | 4/2007 | Garrett et al. |
| 7,212,414 B2 | 5/2007 | Baarman |
| 7,221,966 B2 | 5/2007 | Birli et al. |
| 7,233,137 B2 | 6/2007 | Nakamura et al. |
| D545,855 S | 7/2007 | Garrett et al. |
| 7,239,110 B2 | 7/2007 | Cheng et al. |
| 7,248,017 B2 | 7/2007 | Cheng et al. |
| 7,251,527 B2 | 7/2007 | Lyden |
| 7,288,918 B2 | 10/2007 | DiStefano |
| 7,340,304 B2 | 3/2008 | MacDonald |
| 7,375,492 B2 | 5/2008 | Calhoon et al. |
| 7,375,493 B2 | 5/2008 | Calhoon et al. |
| 7,378,817 B2 | 5/2008 | Calhoon et al. |
| 7,382,636 B2 | 6/2008 | Baarman et al. |
| 7,385,357 B2 | 6/2008 | Kuennen et al. |
| 7,443,135 B2 | 10/2008 | Cho |
| 7,462,951 B1 | 12/2008 | Baarman |
| 7,466,213 B2 | 12/2008 | Löbl et al. |
| 7,471,062 B2 | 12/2008 | Bruning |
| 7,474,058 B2 | 1/2009 | Baarman |
| 7,492,247 B2 | 2/2009 | Schmidt et al. |
| 7,514,818 B2 | 4/2009 | Abe et al. |
| 7,518,267 B2 | 4/2009 | Baarman |
| 7,521,890 B2 | 4/2009 | Lee et al. |
| 7,525,283 B2 | 4/2009 | Cheng et al. |
| 7,545,337 B2 | 6/2009 | Guenther |
| 7,554,316 B2 | 6/2009 | Stevens et al. |
| 7,599,743 B2 | 10/2009 | Hassler, Jr. et al. |
| 7,615,936 B2 | 11/2009 | Baarman et al. |
| 7,639,514 B2 | 12/2009 | Baarman |
| 7,741,734 B2 | 6/2010 | Joannopoulos et al. |
| 7,795,708 B2 | 9/2010 | Katti |
| 7,825,543 B2 | 11/2010 | Karalis et al. |
| 7,825,544 B2 | 11/2010 | Jansen et al. |
| 7,835,417 B2 | 11/2010 | Heideman et al. |
| 7,843,288 B2 | 11/2010 | Lee et al. |
| 7,844,306 B2 | 11/2010 | Shearer et al. |
| 7,863,859 B2 | 1/2011 | Soar |
| 7,880,337 B2 | 2/2011 | Farkas |
| 7,884,697 B2 | 2/2011 | Wei et al. |
| 7,885,050 B2 | 2/2011 | Lee |
| 7,919,886 B2 | 4/2011 | Tanaka |
| 7,923,870 B2 | 4/2011 | Jin |
| 7,932,798 B2 | 4/2011 | Tolle et al. |
| 7,948,209 B2 * | 5/2011 | Jung ............ 320/108 |
| 7,952,322 B2 | 5/2011 | Partovi et al. |
| 7,963,941 B2 * | 6/2011 | Wilk ............ 604/101.01 |
| 7,969,045 B2 | 6/2011 | Schmidt et al. |
| 7,994,880 B2 | 8/2011 | Chen et al. |
| 7,999,506 B1 | 8/2011 | Hollar et al. |
| 8,022,576 B2 | 9/2011 | Joannopoulos et al. |
| 8,035,255 B2 | 10/2011 | Kurs et al. |
| 8,076,800 B2 | 12/2011 | Joannopoulos et al. |
| 8,076,801 B2 | 12/2011 | Karalis et al. |
| 8,084,889 B2 | 12/2011 | Joannopoulos et al. |
| 8,097,983 B2 | 1/2012 | Karalis et al. |
| 8,106,539 B2 | 1/2012 | Schatz et al. |
| 8,115,448 B2 | 2/2012 | John |
| 8,131,378 B2 | 3/2012 | Greenberg et al. |
| 8,178,995 B2 | 5/2012 | Amano et al. |
| 8,193,769 B2 | 6/2012 | Azancot et al. |
| 8,212,414 B2 | 7/2012 | Howard et al. |
| 8,260,200 B2 | 9/2012 | Shimizu et al. |
| 8,304,935 B2 | 11/2012 | Karalis et al. |
| 8,324,759 B2 | 12/2012 | Karalis et al. |
| 8,334,620 B2 | 12/2012 | Park et al. |
| 8,362,651 B2 | 1/2013 | Hamam et al. |
| 8,395,282 B2 | 3/2013 | Joannopoulos et al. |
| 8,395,283 B2 | 3/2013 | Joannopoulos et al. |
| 8,400,017 B2 | 3/2013 | Kurs et al. |
| 8,400,018 B2 | 3/2013 | Joannopoulos et al. |
| 8,400,019 B2 | 3/2013 | Joannopoulos et al. |
| 8,400,020 B2 | 3/2013 | Joannopoulos et al. |
| 8,400,021 B2 | 3/2013 | Joannopoulos et al. |
| 8,400,022 B2 | 3/2013 | Joannopoulos et al. |
| 8,400,023 B2 | 3/2013 | Joannopoulos et al. |
| 8,400,024 B2 | 3/2013 | Joannopoulos et al. |
| 8,410,636 B2 | 4/2013 | Kurs et al. |
| 8,441,154 B2 | 5/2013 | Karalis et al. |
| 8,457,547 B2 | 6/2013 | Meskens |
| 8,461,719 B2 | 6/2013 | Kesler et al. |
| 8,461,720 B2 | 6/2013 | Kurs et al. |
| 8,461,721 B2 | 6/2013 | Karalis et al. |
| 8,461,722 B2 | 6/2013 | Kurs et al. |
| 8,461,817 B2 | 6/2013 | Martin et al. |
| 8,466,583 B2 | 6/2013 | Karalis et al. |
| 8,471,410 B2 | 6/2013 | Karalis et al. |
| 8,476,788 B2 | 7/2013 | Karalis et al. |
| 8,482,157 B2 | 7/2013 | Cook et al. |
| 8,482,158 B2 | 7/2013 | Kurs et al. |
| 8,487,480 B1 | 7/2013 | Kesler et al. |
| 8,497,601 B2 | 7/2013 | Hall et al. |
| 8,552,592 B2 | 10/2013 | Schatz et al. |
| 8,569,914 B2 | 10/2013 | Karalis et al. |
| 8,587,153 B2 | 11/2013 | Schatz et al. |
| 8,587,155 B2 | 11/2013 | Giler et al. |
| 8,598,743 B2 | 12/2013 | Hall et al. |
| 8,618,696 B2 | 12/2013 | Karalis et al. |
| 8,629,578 B2 | 1/2014 | Kurs |
| 8,643,326 B2 | 2/2014 | Campanella et al. |
| 8,669,676 B2 | 3/2014 | Karalis et al. |
| 8,686,598 B2 | 4/2014 | Schatz et al. |
| 8,692,410 B2 | 4/2014 | Schatz et al. |
| 8,692,412 B2 | 4/2014 | Fiorello et al. |
| 2002/0032471 A1 | 3/2002 | Loftin et al. |
| 2002/0105343 A1 | 8/2002 | Scheible et al. |
| 2002/0118004 A1 | 8/2002 | Scheible et al. |
| 2002/0130642 A1 | 9/2002 | Ettes et al. |
| 2002/0167294 A1 | 11/2002 | Odaohhara |
| 2003/0038641 A1 | 2/2003 | Scheible |
| 2003/0062794 A1 | 4/2003 | Scheible et al. |
| 2003/0062980 A1 | 4/2003 | Scheible et al. |
| 2003/0071034 A1 | 4/2003 | Thompson et al. |
| 2003/0124050 A1 | 7/2003 | Yadav et al. |
| 2003/0126948 A1 | 7/2003 | Yadav et al. |
| 2003/0160590 A1 | 8/2003 | Schaefer et al. |
| 2003/0199778 A1 | 10/2003 | Mickle et al. |
| 2003/0214255 A1 | 11/2003 | Baarman et al. |
| 2004/0000974 A1 | 1/2004 | Odenaal et al. |
| 2004/0026998 A1 | 2/2004 | Henriott et al. |
| 2004/0100338 A1 | 5/2004 | Clark |
| 2004/0113847 A1 | 6/2004 | Qi et al. |
| 2004/0130425 A1 | 7/2004 | Dayan et al. |
| 2004/0130915 A1 | 7/2004 | Baarman |
| 2004/0130916 A1 | 7/2004 | Baarman |
| 2004/0142733 A1 | 7/2004 | Parise |

(56) References Cited

U.S. PATENT DOCUMENTS

| | | |
|---|---|---|
| 2004/0150934 A1 | 8/2004 | Baarman |
| 2004/0189246 A1 | 9/2004 | Bulai et al. |
| 2004/0201361 A1 | 10/2004 | Koh et al. |
| 2004/0222751 A1 | 11/2004 | Mollema et al. |
| 2004/0227057 A1 | 11/2004 | Tuominen et al. |
| 2004/0232845 A1 | 11/2004 | Baarman |
| 2004/0233043 A1 | 11/2004 | Yazawa et al. |
| 2004/0267501 A1 | 12/2004 | Freed et al. |
| 2005/0007067 A1 | 1/2005 | Baarman et al. |
| 2005/0021134 A1 | 1/2005 | Opie |
| 2005/0027192 A1 | 2/2005 | Govari et al. |
| 2005/0033382 A1 | 2/2005 | Single |
| 2005/0040983 A1 | 2/2005 | Madau |
| 2005/0085873 A1 | 4/2005 | Gord et al. |
| 2005/0093475 A1 | 5/2005 | Kuennen et al. |
| 2005/0104064 A1 | 5/2005 | Hegarty et al. |
| 2005/0104453 A1 | 5/2005 | Vanderelli et al. |
| 2005/0116650 A1 | 6/2005 | Baarman |
| 2005/0116683 A1 | 6/2005 | Cheng et al. |
| 2005/0122058 A1 | 6/2005 | Baarman et al. |
| 2005/0122059 A1 | 6/2005 | Baarman et al. |
| 2005/0125093 A1 | 6/2005 | Kikuchi et al. |
| 2005/0127849 A1 | 6/2005 | Baarman et al. |
| 2005/0127850 A1 | 6/2005 | Baarman et al. |
| 2005/0127866 A1 | 6/2005 | Hamilton et al. |
| 2005/0135122 A1 | 6/2005 | Cheng et al. |
| 2005/0140482 A1 | 6/2005 | Cheng et al. |
| 2005/0151511 A1 | 7/2005 | Chary |
| 2005/0156560 A1 | 7/2005 | Shimaoka et al. |
| 2005/0189945 A1 | 9/2005 | Reiderman |
| 2005/0194926 A1 | 9/2005 | DiStefano |
| 2005/0253152 A1 | 11/2005 | Klimov et al. |
| 2005/0288739 A1 | 12/2005 | Hassler, Jr. et al. |
| 2005/0288740 A1 | 12/2005 | Hassler, Jr. |
| 2005/0288741 A1 | 12/2005 | Hassler, Jr. et al. |
| 2005/0288742 A1 | 12/2005 | Giordano et al. |
| 2006/0001509 A1 | 1/2006 | Gibbs |
| 2006/0010902 A1 | 1/2006 | Trinh et al. |
| 2006/0022636 A1 | 2/2006 | Xian et al. |
| 2006/0044103 A1 | 3/2006 | Roebke et al. |
| 2006/0053296 A1 | 3/2006 | Busboom et al. |
| 2006/0061323 A1 | 3/2006 | Cheng et al. |
| 2006/0066443 A1 | 3/2006 | Hall |
| 2006/0090956 A1 | 5/2006 | Peshkovskiy et al. |
| 2006/0132045 A1 | 6/2006 | Baarman |
| 2006/0164866 A1 | 7/2006 | Vanderelli et al. |
| 2006/0181242 A1 | 8/2006 | Freed et al. |
| 2006/0184209 A1 | 8/2006 | John et al. |
| 2006/0184210 A1 | 8/2006 | Singhal et al. |
| 2006/0185809 A1 | 8/2006 | Elfrink et al. |
| 2006/0199620 A1 | 9/2006 | Greene et al. |
| 2006/0202665 A1 | 9/2006 | Hsu |
| 2006/0205381 A1 | 9/2006 | Beart et al. |
| 2006/0214626 A1 | 9/2006 | Nilson et al. |
| 2006/0219448 A1 | 10/2006 | Grieve et al. |
| 2006/0238365 A1 | 10/2006 | Vecchione et al. |
| 2006/0250205 A1 | 11/2006 | De et al. |
| 2006/0270440 A1 | 11/2006 | Shearer et al. |
| 2006/0277666 A1 | 12/2006 | Gertsch et al. |
| 2006/0281435 A1 | 12/2006 | Shearer et al. |
| 2007/0010295 A1 | 1/2007 | Greene et al. |
| 2007/0013483 A1 | 1/2007 | Stewart |
| 2007/0016089 A1 | 1/2007 | Fischell et al. |
| 2007/0021140 A1 | 1/2007 | Keyes, IV et al. |
| 2007/0024246 A1 | 2/2007 | Flaugher |
| 2007/0064406 A1 | 3/2007 | Beart |
| 2007/0069687 A1 | 3/2007 | Suzuki |
| 2007/0096875 A1 | 5/2007 | Waterhouse et al. |
| 2007/0105429 A1 | 5/2007 | Kohl et al. |
| 2007/0117596 A1 | 5/2007 | Greene et al. |
| 2007/0126650 A1 | 6/2007 | Guenther |
| 2007/0145830 A1 | 6/2007 | Lee et al. |
| 2007/0164839 A1 | 7/2007 | Naito |
| 2007/0171681 A1 | 7/2007 | Baarman |
| 2007/0176840 A1 | 8/2007 | Pristas et al. |
| 2007/0178945 A1 | 8/2007 | Cook et al. |
| 2007/0182367 A1 | 8/2007 | Partovi |
| 2007/0208263 A1 | 9/2007 | John et al. |
| 2007/0222542 A1 | 9/2007 | Joannopoulos et al. |
| 2007/0257636 A1 | 11/2007 | Phillips et al. |
| 2007/0267918 A1 | 11/2007 | Gyland |
| 2007/0276538 A1 | 11/2007 | Kjellsson et al. |
| 2008/0012569 A1 | 1/2008 | Hall et al. |
| 2008/0014897 A1 | 1/2008 | Cook et al. |
| 2008/0030415 A1 | 2/2008 | Homan et al. |
| 2008/0036588 A1 | 2/2008 | Iverson et al. |
| 2008/0047727 A1 | 2/2008 | Sexton et al. |
| 2008/0051854 A1 | 2/2008 | Bulkes et al. |
| 2008/0067874 A1 | 3/2008 | Tseng |
| 2008/0132909 A1 | 6/2008 | Jascob et al. |
| 2008/0154331 A1 | 6/2008 | John et al. |
| 2008/0176521 A1 | 7/2008 | Singh et al. |
| 2008/0191638 A1 | 8/2008 | Kuennen et al. |
| 2008/0197710 A1 | 8/2008 | Kreitz et al. |
| 2008/0197802 A1 | 8/2008 | Onishi et al. |
| 2008/0211320 A1 | 9/2008 | Cook et al. |
| 2008/0238364 A1 | 10/2008 | Weber et al. |
| 2008/0255901 A1 | 10/2008 | Carroll et al. |
| 2008/0265684 A1 | 10/2008 | Farkas |
| 2008/0266748 A1 | 10/2008 | Lee |
| 2008/0272860 A1 | 11/2008 | Pance |
| 2008/0273242 A1 | 11/2008 | Woodgate et al. |
| 2008/0278264 A1 | 11/2008 | Karalis et al. |
| 2008/0291277 A1 | 11/2008 | Jacobsen et al. |
| 2008/0300657 A1 | 12/2008 | Stultz |
| 2008/0300660 A1 | 12/2008 | John |
| 2009/0010028 A1 | 1/2009 | Baarman et al. |
| 2009/0015075 A1 | 1/2009 | Cook et al. |
| 2009/0033280 A1 | 2/2009 | Choi et al. |
| 2009/0033564 A1 | 2/2009 | Cook et al. |
| 2009/0038623 A1 | 2/2009 | Farbarik et al. |
| 2009/0045772 A1 | 2/2009 | Cook et al. |
| 2009/0051224 A1 | 2/2009 | Cook et al. |
| 2009/0058189 A1 | 3/2009 | Cook et al. |
| 2009/0058361 A1 | 3/2009 | John |
| 2009/0067198 A1 | 3/2009 | Graham |
| 2009/0072627 A1 | 3/2009 | Cook et al. |
| 2009/0072628 A1 | 3/2009 | Cook et al. |
| 2009/0072629 A1 | 3/2009 | Cook et al. |
| 2009/0072782 A1 | 3/2009 | Randall |
| 2009/0079268 A1 | 3/2009 | Cook et al. |
| 2009/0079387 A1 | 3/2009 | Jin et al. |
| 2009/0085408 A1 | 4/2009 | Bruhn et al. |
| 2009/0085706 A1 | 4/2009 | Baarman et al. |
| 2009/0096413 A1 | 4/2009 | Partovi et al. |
| 2009/0102292 A1 | 4/2009 | Cook et al. |
| 2009/0108679 A1 | 4/2009 | Porwal |
| 2009/0108997 A1 | 4/2009 | Petterson et al. |
| 2009/0115628 A1 | 5/2009 | Dicks et al. |
| 2009/0127937 A1 | 5/2009 | Widmer et al. |
| 2009/0134712 A1 | 5/2009 | Cook et al. |
| 2009/0146892 A1 | 6/2009 | Shimizu et al. |
| 2009/0153273 A1 | 6/2009 | Chen et al. |
| 2009/0160261 A1 | 6/2009 | Elo |
| 2009/0161078 A1 | 6/2009 | Wu et al. |
| 2009/0167449 A1 | 7/2009 | Cook et al. |
| 2009/0174263 A1 | 7/2009 | Baarman et al. |
| 2009/0179502 A1 | 7/2009 | Cook et al. |
| 2009/0188396 A1 | 7/2009 | Hofmann et al. |
| 2009/0189458 A1 | 7/2009 | Kawasaki |
| 2009/0195332 A1 | 8/2009 | Joannopoulos et al. |
| 2009/0195333 A1 | 8/2009 | Joannopoulos et al. |
| 2009/0212636 A1 | 8/2009 | Cook et al. |
| 2009/0213028 A1 | 8/2009 | Cook et al. |
| 2009/0218884 A1 | 9/2009 | Soar |
| 2009/0224608 A1 | 9/2009 | Cook et al. |
| 2009/0224609 A1 | 9/2009 | Cook et al. |
| 2009/0224723 A1 | 9/2009 | Tanabe |
| 2009/0224856 A1 | 9/2009 | Karalis et al. |
| 2009/0230777 A1 | 9/2009 | Baarman et al. |
| 2009/0237194 A1 | 9/2009 | Waffenschmidt et al. |
| 2009/0243394 A1 | 10/2009 | Levine |
| 2009/0243397 A1 | 10/2009 | Cook et al. |
| 2009/0251008 A1 | 10/2009 | Sugaya |

(56) References Cited

U.S. PATENT DOCUMENTS

| | | |
|---|---|---|
| 2009/0261778 A1 | 10/2009 | Kook |
| 2009/0267558 A1 | 10/2009 | Jung |
| 2009/0267709 A1 | 10/2009 | Joannopoulos et al. |
| 2009/0267710 A1 | 10/2009 | Joannopoulos et al. |
| 2009/0271047 A1 | 10/2009 | Wakamatsu |
| 2009/0271048 A1 | 10/2009 | Wakamatsu |
| 2009/0273242 A1 | 11/2009 | Cook |
| 2009/0273318 A1 | 11/2009 | Rondoni et al. |
| 2009/0281678 A1 | 11/2009 | Wakamatsu |
| 2009/0284082 A1 | 11/2009 | Mohammadian |
| 2009/0284083 A1 | 11/2009 | Karalis |
| 2009/0284218 A1 | 11/2009 | Mohammadian et al. |
| 2009/0284220 A1 | 11/2009 | Toncich et al. |
| 2009/0284227 A1 | 11/2009 | Mohammadian et al. |
| 2009/0284245 A1 | 11/2009 | Kirby et al. |
| 2009/0284369 A1 | 11/2009 | Toncich et al. |
| 2009/0286470 A1 | 11/2009 | Mohammadian et al. |
| 2009/0286475 A1 | 11/2009 | Toncich et al. |
| 2009/0286476 A1 | 11/2009 | Toncich et al. |
| 2009/0289595 A1 | 11/2009 | Chen et al. |
| 2009/0299918 A1 | 12/2009 | Cook et al. |
| 2009/0322158 A1 | 12/2009 | Stevens et al. |
| 2009/0322280 A1 | 12/2009 | Kamijo et al. |
| 2010/0015918 A1 | 1/2010 | Liu et al. |
| 2010/0017249 A1 | 1/2010 | Fincham et al. |
| 2010/0033021 A1 | 2/2010 | Bennett |
| 2010/0034238 A1 | 2/2010 | Bennett |
| 2010/0036773 A1 | 2/2010 | Bennett |
| 2010/0038970 A1 | 2/2010 | Cook et al. |
| 2010/0045114 A1 | 2/2010 | Sample |
| 2010/0052431 A1 | 3/2010 | Mita |
| 2010/0052811 A1 | 3/2010 | Smith et al. |
| 2010/0060077 A1 | 3/2010 | Paulus et al. |
| 2010/0065352 A1 | 3/2010 | Ichikawa |
| 2010/0066349 A1 | 3/2010 | Lin et al. |
| 2010/0076524 A1 | 3/2010 | Forsberg et al. |
| 2010/0081379 A1 | 4/2010 | Cooper et al. |
| 2010/0094381 A1 | 4/2010 | Kim et al. |
| 2010/0096934 A1 | 4/2010 | Joannopoulos |
| 2010/0100997 A1 | 4/2010 | Lee et al. |
| 2010/0102639 A1 | 4/2010 | Joannopoulos |
| 2010/0102640 A1 | 4/2010 | Joannopoulos |
| 2010/0102641 A1 | 4/2010 | Joannopoulos |
| 2010/0104031 A1 | 4/2010 | Lacour |
| 2010/0109443 A1 | 5/2010 | Cook et al. |
| 2010/0109445 A1 | 5/2010 | Kurs et al. |
| 2010/0109604 A1 | 5/2010 | Boys |
| 2010/0115474 A1 | 5/2010 | Takada et al. |
| 2010/0117454 A1 | 5/2010 | Cook et al. |
| 2010/0117455 A1 | 5/2010 | Joannopoulos |
| 2010/0117456 A1 | 5/2010 | Karalis |
| 2010/0117596 A1 | 5/2010 | Cook et al. |
| 2010/0123353 A1 | 5/2010 | Joannopoulos |
| 2010/0123354 A1 | 5/2010 | Joannopoulos |
| 2010/0123355 A1 | 5/2010 | Joannopoulos |
| 2010/0123452 A1 | 5/2010 | Amano et al. |
| 2010/0123530 A1 | 5/2010 | Park et al. |
| 2010/0127573 A1 | 5/2010 | Joannopoulos |
| 2010/0127574 A1 | 5/2010 | Joannopoulos |
| 2010/0127575 A1 | 5/2010 | Joannopoulos |
| 2010/0127660 A1 | 5/2010 | Cook et al. |
| 2010/0133918 A1 | 6/2010 | Joannopoulos |
| 2010/0133919 A1 | 6/2010 | Joannopoulos |
| 2010/0133920 A1 | 6/2010 | Joannopoulos |
| 2010/0141042 A1 | 6/2010 | Kesler et al. |
| 2010/0148589 A1 | 6/2010 | Hamam |
| 2010/0148723 A1 | 6/2010 | Cook et al. |
| 2010/0151808 A1 | 6/2010 | Toncich et al. |
| 2010/0156346 A1 | 6/2010 | Takada et al. |
| 2010/0156355 A1 | 6/2010 | Bauerle et al. |
| 2010/0156570 A1 | 6/2010 | Hong et al. |
| 2010/0164295 A1 | 7/2010 | Ichikawa et al. |
| 2010/0164296 A1 | 7/2010 | Kurs et al. |
| 2010/0164297 A1 | 7/2010 | Kurs et al. |
| 2010/0164298 A1 | 7/2010 | Karalis et al. |
| 2010/0171368 A1 | 7/2010 | Schatz et al. |
| 2010/0171370 A1 | 7/2010 | Karalis et al. |
| 2010/0179384 A1 | 7/2010 | Hoeg et al. |
| 2010/0181843 A1 | 7/2010 | Schatz et al. |
| 2010/0181844 A1 | 7/2010 | Karalis et al. |
| 2010/0181845 A1 | 7/2010 | Fiorello et al. |
| 2010/0181961 A1 | 7/2010 | Von Novak et al. |
| 2010/0181964 A1 | 7/2010 | Huggins et al. |
| 2010/0184371 A1 | 7/2010 | Cook et al. |
| 2010/0187911 A1 | 7/2010 | Joannopoulos |
| 2010/0187913 A1 | 7/2010 | Smith et al. |
| 2010/0188183 A1 | 7/2010 | Shpiro |
| 2010/0190435 A1 | 7/2010 | Cook et al. |
| 2010/0190436 A1 | 7/2010 | Cook et al. |
| 2010/0194206 A1 | 8/2010 | Burdo et al. |
| 2010/0194207 A1 | 8/2010 | Graham |
| 2010/0194334 A1 | 8/2010 | Kirby et al. |
| 2010/0194335 A1 | 8/2010 | Kirby et al. |
| 2010/0201189 A1 | 8/2010 | Kirby et al. |
| 2010/0201201 A1 | 8/2010 | Mobarhan et al. |
| 2010/0201202 A1 | 8/2010 | Kirby et al. |
| 2010/0201203 A1 | 8/2010 | Schatz et al. |
| 2010/0201204 A1 | 8/2010 | Sakoda et al. |
| 2010/0201205 A1 | 8/2010 | Karalis et al. |
| 2010/0201310 A1 | 8/2010 | Vorenkamp et al. |
| 2010/0201312 A1 | 8/2010 | Kirby et al. |
| 2010/0201313 A1 | 8/2010 | Vorenkamp et al. |
| 2010/0201316 A1 | 8/2010 | Takada et al. |
| 2010/0201513 A1 | 8/2010 | Vorenkamp et al. |
| 2010/0207458 A1 | 8/2010 | Joannopoulos |
| 2010/0210233 A1 | 8/2010 | Cook et al. |
| 2010/0213770 A1 | 8/2010 | Kikuchi |
| 2010/0213895 A1 | 8/2010 | Keating et al. |
| 2010/0217553 A1 | 8/2010 | Von Novak et al. |
| 2010/0219694 A1 | 9/2010 | Kurs |
| 2010/0219695 A1 | 9/2010 | Komiyama et al. |
| 2010/0219696 A1 | 9/2010 | Kojima |
| 2010/0222010 A1 | 9/2010 | Ozaki et al. |
| 2010/0225175 A1 | 9/2010 | Karalis et al. |
| 2010/0225270 A1 | 9/2010 | Jacobs et al. |
| 2010/0225271 A1 | 9/2010 | Oyobe et al. |
| 2010/0225272 A1 | 9/2010 | Kirby et al. |
| 2010/0231053 A1 | 9/2010 | Karalis et al. |
| 2010/0231163 A1 | 9/2010 | Mashinsky |
| 2010/0231340 A1 | 9/2010 | Fiorello |
| 2010/0234922 A1 | 9/2010 | Forsell |
| 2010/0235006 A1 | 9/2010 | Brown |
| 2010/0237706 A1 | 9/2010 | Karalis |
| 2010/0237707 A1 | 9/2010 | Karalis |
| 2010/0237708 A1 | 9/2010 | Karalis et al. |
| 2010/0237709 A1 | 9/2010 | Hall et al. |
| 2010/0244576 A1 | 9/2010 | Hillan et al. |
| 2010/0244577 A1 | 9/2010 | Shimokawa |
| 2010/0244578 A1 | 9/2010 | Yoshikawa et al. |
| 2010/0244579 A1 | 9/2010 | Sogabe et al. |
| 2010/0244580 A1 | 9/2010 | Uchida et al. |
| 2010/0244581 A1 | 9/2010 | Uchida |
| 2010/0244582 A1 | 9/2010 | Yoshikawa |
| 2010/0244583 A1 | 9/2010 | Shimokawa |
| 2010/0244767 A1 | 9/2010 | Turner et al. |
| 2010/0244839 A1 | 9/2010 | Yoshikawa |
| 2010/0248622 A1 | 9/2010 | Kirby et al. |
| 2010/0253152 A1 | 10/2010 | Karalis |
| 2010/0253281 A1 | 10/2010 | Li |
| 2010/0256481 A1 | 10/2010 | Mareci et al. |
| 2010/0256831 A1 | 10/2010 | Abramo et al. |
| 2010/0259108 A1 | 10/2010 | Giler et al. |
| 2010/0259109 A1 | 10/2010 | Sato |
| 2010/0259110 A1 | 10/2010 | Kurs et al. |
| 2010/0264745 A1 | 10/2010 | Karalis et al. |
| 2010/0264746 A1 | 10/2010 | Kazama et al. |
| 2010/0264747 A1 | 10/2010 | Hall et al. |
| 2010/0276995 A1 | 11/2010 | Marzetta et al. |
| 2010/0277003 A1 | 11/2010 | Von Novak et al. |
| 2010/0277004 A1 | 11/2010 | Suzuki et al. |
| 2010/0277005 A1 | 11/2010 | Karalis et al. |
| 2010/0277120 A1 | 11/2010 | Cook et al. |
| 2010/0277121 A1 | 11/2010 | Hall et al. |
| 2010/0289341 A1 | 11/2010 | Ozaki et al. |

(56) References Cited

U.S. PATENT DOCUMENTS

| | | |
|---|---|---|
| 2010/0289449 A1 | 11/2010 | Elo |
| 2010/0295505 A1 | 11/2010 | Jung et al. |
| 2010/0295506 A1 | 11/2010 | Ichikawa |
| 2010/0308939 A1 | 12/2010 | Kurs |
| 2010/0314946 A1 | 12/2010 | Budde et al. |
| 2010/0327660 A1 | 12/2010 | Karalis et al. |
| 2010/0327661 A1 | 12/2010 | Karalis et al. |
| 2010/0328044 A1 | 12/2010 | Waffenschmidt et al. |
| 2011/0004269 A1 | 1/2011 | Strother et al. |
| 2011/0012431 A1 | 1/2011 | Karalis et al. |
| 2011/0018361 A1 | 1/2011 | Karalis et al. |
| 2011/0025131 A1 | 2/2011 | Karalis et al. |
| 2011/0031928 A1 | 2/2011 | Soar |
| 2011/0043046 A1 | 2/2011 | Joannopoulos et al. |
| 2011/0043047 A1 | 2/2011 | Karalis et al. |
| 2011/0043048 A1 | 2/2011 | Karalis et al. |
| 2011/0043049 A1 | 2/2011 | Karalis et al. |
| 2011/0049995 A1 | 3/2011 | Hashiguchi |
| 2011/0049996 A1 | 3/2011 | Karalis et al. |
| 2011/0049998 A1 | 3/2011 | Karalis et al. |
| 2011/0074218 A1 | 3/2011 | Karalis et al. |
| 2011/0074346 A1 | 3/2011 | Hall et al. |
| 2011/0074347 A1 | 3/2011 | Karalis et al. |
| 2011/0089895 A1 | 4/2011 | Karalis et al. |
| 2011/0095618 A1 | 4/2011 | Schatz et al. |
| 2011/0115303 A1 | 5/2011 | Baarman et al. |
| 2011/0115431 A1 | 5/2011 | Dunworth et al. |
| 2011/0121920 A1 | 5/2011 | Kurs et al. |
| 2011/0128015 A1 | 6/2011 | Dorairaj et al. |
| 2011/0140544 A1 | 6/2011 | Karalis et al. |
| 2011/0148219 A1 | 6/2011 | Karalis et al. |
| 2011/0162895 A1 | 7/2011 | Karalis et al. |
| 2011/0169339 A1 | 7/2011 | Karalis et al. |
| 2011/0181122 A1 | 7/2011 | Karalis et al. |
| 2011/0193416 A1 | 8/2011 | Campanella et al. |
| 2011/0193419 A1 | 8/2011 | Karalis et al. |
| 2011/0198939 A1 | 8/2011 | Karalis et al. |
| 2011/0215086 A1 | 9/2011 | Yeh |
| 2011/0221278 A1 | 9/2011 | Karalis et al. |
| 2011/0227528 A1 | 9/2011 | Karalis et al. |
| 2011/0227530 A1 | 9/2011 | Karalis et al. |
| 2011/0241618 A1 | 10/2011 | Karalis et al. |
| 2011/0248573 A1 | 10/2011 | Kanno et al. |
| 2011/0254377 A1 | 10/2011 | Wildmer et al. |
| 2011/0254503 A1 | 10/2011 | Widmer et al. |
| 2011/0266878 A9 | 11/2011 | Cook et al. |
| 2011/0278943 A1 | 11/2011 | Eckhoff et al. |
| 2011/0282415 A1 | 11/2011 | Eckhoff et al. |
| 2012/0001492 A9 | 1/2012 | Cook et al. |
| 2012/0001593 A1 | 1/2012 | DiGuardo |
| 2012/0007435 A1 | 1/2012 | Sada et al. |
| 2012/0007441 A1 | 1/2012 | John |
| 2012/0025602 A1 | 2/2012 | Boys et al. |
| 2012/0032522 A1 | 2/2012 | Schatz et al. |
| 2012/0038525 A1 | 2/2012 | Monsalve Carcelen et al. |
| 2012/0062345 A1 | 3/2012 | Kurs et al. |
| 2012/0068549 A1 | 3/2012 | Karalis et al. |
| 2012/0086284 A1 | 4/2012 | Capanella et al. |
| 2012/0086867 A1 | 4/2012 | Kesler et al. |
| 2012/0091794 A1 | 4/2012 | Campanella et al. |
| 2012/0091795 A1 | 4/2012 | Fiorello et al. |
| 2012/0091796 A1 | 4/2012 | Kesler et al. |
| 2012/0091797 A1 | 4/2012 | Kesler et al. |
| 2012/0091819 A1 | 4/2012 | Kulikowski et al. |
| 2012/0091820 A1 | 4/2012 | Campanella et al. |
| 2012/0091949 A1 | 4/2012 | Campanella et al. |
| 2012/0091950 A1 | 4/2012 | Campanella et al. |
| 2012/0098350 A1 | 4/2012 | Campanella et al. |
| 2012/0112531 A1 | 5/2012 | Kesler et al. |
| 2012/0112532 A1 | 5/2012 | Kesler et al. |
| 2012/0112534 A1 | 5/2012 | Kesler et al. |
| 2012/0112535 A1 | 5/2012 | Karalis et al. |
| 2012/0112536 A1 | 5/2012 | Karalis et al. |
| 2012/0112538 A1 | 5/2012 | Kesler et al. |
| 2012/0112691 A1 | 5/2012 | Kurs et al. |
| 2012/0119569 A1 | 5/2012 | Karalis et al. |
| 2012/0119575 A1 | 5/2012 | Kurs et al. |
| 2012/0119576 A1 | 5/2012 | Kesler et al. |
| 2012/0119698 A1 | 5/2012 | Karalis et al. |
| 2012/0139355 A1 | 6/2012 | Ganem et al. |
| 2012/0146575 A1 | 6/2012 | Armstrong et al. |
| 2012/0153732 A1 | 6/2012 | Kurs et al. |
| 2012/0153733 A1 | 6/2012 | Schatz et al. |
| 2012/0153734 A1 | 6/2012 | Kurs et al. |
| 2012/0153735 A1 | 6/2012 | Karalis et al. |
| 2012/0153736 A1 | 6/2012 | Karalis et al. |
| 2012/0153737 A1 | 6/2012 | Karalis et al. |
| 2012/0153738 A1 | 6/2012 | Karalis et al. |
| 2012/0153893 A1 | 6/2012 | Schatz et al. |
| 2012/0184338 A1 | 7/2012 | Kesler et al. |
| 2012/0206096 A1 | 8/2012 | John |
| 2012/0223573 A1 | 9/2012 | Schatz et al. |
| 2012/0228952 A1 | 9/2012 | Hall et al. |
| 2012/0228953 A1 | 9/2012 | Kesler et al. |
| 2012/0228954 A1 | 9/2012 | Kesler et al. |
| 2012/0235500 A1 | 9/2012 | Kesler et al. |
| 2012/0235501 A1 | 9/2012 | Kesler et al. |
| 2012/0235502 A1 | 9/2012 | Kesler et al. |
| 2012/0235503 A1 | 9/2012 | Kesler et al. |
| 2012/0235504 A1 | 9/2012 | Kesler et al. |
| 2012/0235505 A1 | 9/2012 | Schatz et al. |
| 2012/0235566 A1 | 9/2012 | Karalis et al. |
| 2012/0235567 A1 | 9/2012 | Karalis et al. |
| 2012/0235633 A1 | 9/2012 | Kesler et al. |
| 2012/0235634 A1 | 9/2012 | Hall et al. |
| 2012/0239117 A1 | 9/2012 | Kesler et al. |
| 2012/0242159 A1 | 9/2012 | Lou et al. |
| 2012/0242225 A1 | 9/2012 | Karalis et al. |
| 2012/0248884 A1 | 10/2012 | Karalis et al. |
| 2012/0248886 A1 | 10/2012 | Kesler et al. |
| 2012/0248887 A1 | 10/2012 | Kesler et al. |
| 2012/0248888 A1 | 10/2012 | Kesler et al. |
| 2012/0248981 A1 | 10/2012 | Karalis et al. |
| 2012/0256494 A1 | 10/2012 | Kesler et al. |
| 2012/0267960 A1 | 10/2012 | Low et al. |
| 2012/0280765 A1 | 11/2012 | Kurs et al. |
| 2012/0313449 A1 | 12/2012 | Kurs et al. |
| 2012/0313742 A1 | 12/2012 | Kurs et al. |
| 2013/0007949 A1 | 1/2013 | Kurs et al. |
| 2013/0020878 A1 | 1/2013 | Karalis et al. |
| 2013/0033118 A1 | 2/2013 | Karalis et al. |
| 2013/0038402 A1 | 2/2013 | Karalis et al. |
| 2013/0057364 A1 | 3/2013 | Kesler et al. |
| 2013/0062966 A1 | 3/2013 | Verghese et al. |
| 2013/0069441 A1 | 3/2013 | Verghese et al. |
| 2013/0069753 A1 | 3/2013 | Kurs et al. |
| 2013/0099587 A1 | 4/2013 | Lou et al. |
| 2013/0154383 A1 | 6/2013 | Kasturi et al. |
| 2013/0154389 A1 | 6/2013 | Kurs et al. |
| 2013/0159956 A1 | 6/2013 | Verghese et al. |
| 2013/0175874 A1 | 7/2013 | Lou et al. |
| 2013/0175875 A1 | 7/2013 | Kurs et al. |
| 2013/0200716 A1 | 8/2013 | Kesler et al. |
| 2013/0200721 A1 | 8/2013 | Kurs et al. |
| 2013/0221744 A1 | 8/2013 | Hall et al. |
| 2013/0278073 A1 | 10/2013 | Kurs et al. |
| 2013/0278074 A1 | 10/2013 | Kurs et al. |
| 2013/0278075 A1 | 10/2013 | Kurs et al. |
| 2013/0300353 A1 | 11/2013 | Kurs et al. |
| 2013/0307349 A1 | 11/2013 | Hall et al. |
| 2013/0320773 A1 | 12/2013 | Schatz et al. |
| 2013/0334892 A1 | 12/2013 | Hall et al. |
| 2014/0002012 A1 | 1/2014 | McCauley et al. |
| 2014/0021798 A1 | 1/2014 | Kesler et al. |
| 2014/0035378 A1 | 2/2014 | Kesler et al. |
| 2014/0035704 A1 | 2/2014 | Efe et al. |
| 2014/0044281 A1 | 2/2014 | Ganem et al. |
| 2014/0044293 A1 | 2/2014 | Ganem et al. |
| 2014/0049118 A1 | 2/2014 | Karalis et al. |

(56) References Cited

U.S. PATENT DOCUMENTS

| | | |
|---|---|---|
| 2014/0070764 A1 | 3/2014 | Keeling |
| 2014/0084703 A1 | 3/2014 | Hall et al. |

FOREIGN PATENT DOCUMENTS

| | | |
|---|---|---|
| CN | 102439669 | 5/2012 |
| CN | 103329397 | 9/2013 |
| DE | 3824972 | 1/1989 |
| DE | 10029147 | 12/2001 |
| DE | 20016655 U1 | 2/2002 |
| DE | 10221484 A1 | 11/2003 |
| DE | 10304584 | 8/2004 |
| DE | 102005036290 | 2/2007 |
| DE | 102006044057 | 4/2008 |
| EP | 1335477 | 8/2003 |
| EP | 1 521 206 | 4/2005 |
| EP | 1 524 010 | 4/2005 |
| EP | 2340611 A1 | 7/2011 |
| EP | 2357716 A2 | 8/2011 |
| EP | 2396796 A1 | 12/2011 |
| IN | 1734/KOLNP/2011 | 9/2011 |
| JP | 02097005 A | 4/1990 |
| JP | 04265875 A | 9/1992 |
| JP | 6-341410 | 12/1994 |
| JP | 09182323 A | 7/1997 |
| JP | 09298847 A | 11/1997 |
| JP | 10164837 A | 6/1998 |
| JP | 11075329 A | 3/1999 |
| JP | 11188113 A | 7/1999 |
| JP | 2001309580 A | 11/2001 |
| JP | 2002010535 A | 1/2002 |
| JP | 2003179526 A | 6/2003 |
| JP | 2004166459 A | 6/2004 |
| JP | 2004201458 A | 7/2004 |
| JP | 2004-229144 | 8/2004 |
| JP | 2005057444 A | 3/2005 |
| JP | 2005110409 A | 4/2005 |
| JP | 2005149238 A | 6/2005 |
| JP | 2005218021 A | 8/2005 |
| JP | 2006-074848 | 3/2006 |
| JP | 2007505480 A | 3/2007 |
| JP | 2007-266892 | 10/2007 |
| JP | 2007537637 A | 12/2007 |
| JP | 2008508842 A | 3/2008 |
| JP | 2008206231 A | 9/2008 |
| JP | 2008206327 A | 9/2008 |
| JP | 2011072074 A | 4/2011 |
| JP | 2012504387 A | 2/2012 |
| JP | 2013543718 A | 12/2013 |
| KR | 10-2007-0017804 | 2/2007 |
| KR | 1020080007635 A | 1/2008 |
| KR | 1020090122072 A | 11/2009 |
| KR | 1020110050920 A | 5/2011 |
| SG | 112842 | 7/2005 |
| WO | WO-92/17929 | 10/1992 |
| WO | WO-93/23908 | 11/1993 |
| WO | WO-94/28560 | 12/1994 |
| WO | WO 95/11545 | 4/1995 |
| WO | WO-96/02970 | 2/1996 |
| WO | WO-98/50993 | 11/1998 |
| WO | WO-00/77910 | 12/2000 |
| WO | WO-03/092329 | 11/2003 |
| WO | WO-03/096361 | 11/2003 |
| WO | WO-03/096512 | 11/2003 |
| WO | WO 2004/015885 | 2/2004 |
| WO | WO-2004/038888 | 5/2004 |
| WO | WO-2004/055654 | 7/2004 |
| WO | WO 2004/055654 | 7/2004 |
| WO | WO-2004/073150 | 8/2004 |
| WO | WO-2004/073166 | 8/2004 |
| WO | WO-2004/073176 | 8/2004 |
| WO | WO-2004/073177 | 8/2004 |
| WO | WO-2004/112216 | 12/2004 |
| WO | WO-2005/024865 | 3/2005 |
| WO | WO-2005/060068 | 6/2005 |
| WO | WO-2005/109597 | 11/2005 |
| WO | WO-2005/109598 | 11/2005 |
| WO | 2006011769 A1 | 2/2006 |
| WO | WO2007/008646 A2 | 1/2007 |
| WO | WO-2007/008646 A2 | 1/2007 |
| WO | WO-2007/020583 | 2/2007 |
| WO | WO-2007/042952 | 4/2007 |
| WO | WO-2007/084716 | 7/2007 |
| WO | WO-2007/084717 | 7/2007 |
| WO | WO-2008/109489 | 9/2008 |
| WO | WO-2008/118178 | 10/2008 |
| WO | 2009014125 A1 | 1/2009 |
| WO | WO-2009/009559 | 1/2009 |
| WO | WO-2009/018568 | 2/2009 |
| WO | WO-2009/023155 | 2/2009 |
| WO | WO-2009/023646 | 2/2009 |
| WO | WO-2009/033043 | 3/2009 |
| WO | 2009062438 A1 | 5/2009 |
| WO | WO-2009/070730 | 6/2009 |
| WO | WO-2009/126963 | 10/2009 |
| WO | WO/2009/140506 | 11/2009 |
| WO | WO-2009/140506 | 11/2009 |
| WO | WO2009/149464 | 12/2009 |
| WO | WO-2009/149464 | 12/2009 |
| WO | WO-2009/155000 | 12/2009 |
| WO | WO-2010/030977 | 3/2010 |
| WO | WO2010/030977 | 3/2010 |
| WO | WO/2010/039967 | 4/2010 |
| WO | WO-2010/039967 | 4/2010 |
| WO | WO-2010036980 A1 | 4/2010 |
| WO | WO-2010/090538 | 8/2010 |
| WO | WO-2010/090539 | 8/2010 |
| WO | WO-2010/093997 | 8/2010 |
| WO | WO/2010/093997 | 8/2010 |
| WO | 2010104569 A1 | 9/2010 |
| WO | 2011061388 A1 | 5/2011 |
| WO | 2011061821 A1 | 5/2011 |
| WO | 2011062827 A2 | 5/2011 |
| WO | 2011112795 A1 | 9/2011 |
| WO | 2012037279 A1 | 3/2012 |
| WO | 2012170278 A2 | 12/2012 |
| WO | 2012170278 A3 | 1/2013 |
| WO | 2013013235 A2 | 1/2013 |
| WO | 2013020138 A2 | 2/2013 |
| WO | 2013036947 A2 | 3/2013 |
| WO | 2013020138 A3 | 4/2013 |
| WO | 2013059441 A1 | 4/2013 |
| WO | 2013013235 A3 | 5/2013 |
| WO | 2013036947 A3 | 5/2013 |
| WO | 2013067484 A1 | 5/2013 |
| WO | 2013113017 A1 | 8/2013 |
| WO | 2013142840 A1 | 9/2013 |
| WO | 2014004843 A1 | 1/2014 |

OTHER PUBLICATIONS

U.S. Appl. No. 12/759,047, Non Final Office Action mailed Jul. 18, 2013, 7 pages.

International Application Serial No. PCT/US2011/051634, International Preliminary Report on Patentability mailed Mar. 28, 2013, Witricity Corporation et al, 8 pages.

International Application Serial No. PCT/US2012/040184, International Search Report and Written Opinion mailed Nov. 28, 2012, Witricity Corporation et al., 8 pages.

International Application Serial No. PCT/US2012/047844, International Search Report and Written Opinion mailed Mar. 25, 2013, Witricity Corporation et al, 9 pages.

International Application Serial No. PCT/US2012/049777, International Search Report and Written Opinion mailed Jan. 23, 2013, 10 pages.

International Application Serial No. PCT/US2012/054490, International Search Report and Written Opinion mailed Feb. 28, 2013, Witricity Corporation et al, 8 pages.

International Application Serial No. PCT/US2012/060793, International Search Report and Written Opinion mailed Mar. 8, 2013, Witricity Corporation, 13 pages.

(56) References Cited

OTHER PUBLICATIONS

International Application Serial No. PCT/US2012/063530, International Search Report and Written Opinion mailed Mar. 13, 2013, Witricity Corporation, 16 pages.
International Application Serial No. PCT/US2013/023478, International Search Report and Written Opinion mailed Jun. 25, 2013, Witricity Corporation, 15 pages.
International Application No. PCT/US2011/027868, International Search Report and Written Opinion mailed Jul. 5, 2011, 9 pages.
International Application Serial No. PCT/US2009/058499, International Preliminary Report on Patentability issued on Mar. 29, 2011, 5 pages.
International Application Serial No. PCT/US2010/024199, International Search Report and Written Opinion mailed May 14, 2010, 8 pages.
International Application Serial No. PCT/US2011/051634, International Search Report and Written Opinion mailed on Jan. 6, 2012, 11 pages.
International Application Serial No. PCT/US2011/054544, International Search Report mailed on Jan. 30, 2012, 2 pages.
Kurs et al., "Optimized design of a low-resistance electrical conductor for the multimegahertz range," Applied Physics Letter, vol. 98, Issue 17, Apr. 28, 2011, pp. 172504-1-172504-3.
Kurs et al., "Simultaneous mid-range power transfer to multiple devices", Applied Physics Letters, vol. 96, No. 044102, Feb. 2, 2010, pp. 044102-1-044102-3.
Schneider, David, "Electrons Unplugged, Wireless power at a distance is still far away," IEEE Spectrum, May 2010, pp. 35-39.
Schuder et al., "Energy Transport Into the Closed Chest From a Set of Very-Large Mutually Orthogonal Coils", Communication Electronics, vol. 64, Jan. 1963, pp. 527-534.
Schuder et al., "An Inductively Coupled RF System for the Transmission of 1 kW of Power Through the Skin", IEEE Transactions on Bio-Medical Engineering, vol. BME-18, No. 4, Jul. 1971, pp. 265-273.
Schuder, John C., "Powering an Artificial Heart: Birth of the Inductively Coupled-Radio Frequency System in 1960", Artificial Organs, vol. 26, No. 11, Jun. 2002, pp. 909-915.
Soljacic, Marin, "Wireless non-radiative energy transfer", Visions of Discovery New Light on Physics, Cosmology, and Consciousness, Cambridge University Press, New York, 2011, pp. 530-542.
Stark III, Joseph C., "Wireless Power Transmission Utilizing a Phased Array of Tesla Coils", Master Thesis, Massachusetts Institute of Technology, May 2004, 247 pages.
U.S. Appl. No. 60/698,442, "Wireless Non-Radiative Energy Transfer", filed Jul. 12, 2005, 14 pages.
U.S. Appl. No. 60/908,666, "Wireless Energy Transfer", filed Mar. 28, 2007, 108 pages.
International Application Serial No. PCT/US2011/027868, International Preliminary Report on Patentability mailed Sep. 20, 2012, 8 pages.
Castelvecchi, Davide ""The Power of Induction—Cutting the last cord could resonate with our increasingly gadget-dependent lives"", Science News Online vol. 172 No. 3 week of Jul. 21, 2007.
"Tutorial overview of inductively coupled RFID systems", UPM Rafsec May 2003 , 7 pages.
"ISR and WO for Int'l Appl. No. PCT/US2007/070892", PCT/US2007/070892 Mar. 3, 2008.
Baker, ""Feedback Analysis and Design of RF Power Linksw for Low-Power Bionic Systems"", IEEE Transactions on Biomedical Circuits and Systems 1(1):28-38 Mar. 2007.
Mediano, A "Design of class E amplifier with nonlinear and linear shunt capacitances for any duty cycle", IEEE Trans. Microwave Theor. vol. 55 No. 3, Mar. 2007 , 484-492.
Hirai, ""Study on Intelligent Battery Charging Using Inductive Transmission of Power and Information"", IEEE 15(2) Mar. 2000 , 335-345.
Abe, ""A noncontact Charger Using a Resonant Converter with Parallel Capacitor of the Secondary Coil"", IEEE 36(2) Mar./Apr. 2000 , 444-451.
Sekiya, H. "FM/PWM control scheme in class DE inverter.", IEEE Trans. Circuits Syst. 1, vol. 51, No. 7, Jul. 2004 Jul. 2007, 1250-1260.
Tesla, Nikola ""High Frequency Oscillators for Electro-Therapeutic and Other Purposes"", Proceedings of the IEEE, vol. 87 Jul. 1999 , 1282-1292.
""Physics Update, Unwired Energy"", Physics Today, (see http://arxiv.org/abs/physics/0611063) Jan. 2007 , 26.
Hirai, ""Integral Motor with Driver and Wireless Transmission of Power and Information for Autonomous Subspindle Drive"", IEEE 15(1) Jan. 2000 , 13-20.
Hirai, ""Wireless Transmission of Power and Information and Information for Cableless Linear Motor Drive"", IEEE vol. 15 No. 1 Transactions on Power Electronics Jan. 2000 , 21-27.
Burri, ""Invention Description"", Feb. 5, 2008.
""The Big Story for CES 2007: The public debut of eCoupled Intelligent Wireless Power"", Press Release Fulton Innovation LLC Las Vegas, NV Dec. 27, 2006.
Someya, Takao ""The world's first sheet-type wireless power transmission system"", University of Tokyo Dec. 12, 2006.
""The world's first sheet-type wireless power transmission system: Will a socket be replaced by e-wall?"", Press Release, Tokyo, Japan Dec. 12, 2006.
Geyi, Wen ""A Method for the Evaluation of Small Antenna Q."", IEEE Transactions on Antennas and Propagation vol. 51, No. 8 Aug. 2003.
Liang, ""Silicon waveguide two-photon absorption detector at 1.5 µm wavelength for autocorrelation measurements"", Applied Physics Letters 81(7) Aug. 12, 2002 , 1323-1325.
Hirai, ""Practical Study on Wireless Transmission of Power and Information for Autonomous Decentralized Manufacturing System"", Transactions on Industrial Electronics IEEE vol. 46, No. 2 Apr. 1999 , 349-359.
Splashpower, ""Splashpower—World Leaders in Wireless Power"", Powerpoint presentation Sep. 3, 2007 , 30 pages.
""Unwired energy questions asked, answered"", Physics Today Sep. 2007 , 16-17.
""HF Antenna Design Notes—Technical Application Report"", Texas Instruments Literature No. 11/08/003 Sep. 2003 , 47 pages.
Soljacic, Marin ""Photonic-crystal slow light enhancement of non-linear phase sensitivity"", J. Opt. Soc. Am B vol. 19, No. 9 Sep. 2002 , 2052-2059.
"Australian Application No. 2006069374—Examination Report", Australian Application No. 2006069374—Examination Report Sep. 18, 2008.
Thomsen, ""Ultrahigh speed all-optical demultiplexing based on two-photo absorption in a laser diode"", Electronics Letters, 34(19) Sep. 17, 1998 , 1871-1872.
Markoff, John ""Intel Moves to Free Gadgets of Their Recharging Cords"", The New York Times—nytimes.com Aug. 21, 2008.
Kurs, Andre ""Wireless Power Transfer via Strongly Coupled Magnetic Resonances"", Science vol. 317 Jul. 6, 2007 , 83-86.
Zierhofer, Clemens ""High Efficiency Coupling-Insensitive Transcutaneous Power and Data Transmission Via an Inductive link"", IEEE Transactions on Biomedical Engineering, vol. 37, No. 7 Jul. 1990 , 716-722.
Boyle, Alan ""Electro-nirvana? Not so fast"", MSNBC Jun. 8, 2007.
Bulkeley, William M. ""MIT Scientists Pave the Way for Wireless Battery Charging"", The Wall Street Journal (See http://online.wsj.com/articleSB118123955549228045.html?mod=googlenews_wsj) Jun. 8, 2007.
Reidy, Chris ""MIT discovery could unplug your iPod forever"", Globe staff Boston.com (see http://www.boston.com/business/ticker/2007/06/mit_discovery_c.html) Jun. 7, 2007.
Hadley, Franklin "MIT Team Experimentally Demonstrates Wireless Power Transfer, Potentially Useful for Power Laptops, Cell-Phones Without Cords,—Good-Bye Wires . . . ", Institute for Soldier Nanotechnologies, Massachusetts Institute of Technology Jun. 7, 2007.
Derbyshire, David ""The end of the plug? Scientists invent wireless device that beams electricity through your home"", Daily Mail (see http://www.dailymail.co.uk/pages/live/articles/technology.html?in_article_id=4) Jun. 7, 2007.

(56) References Cited

OTHER PUBLICATIONS

Minkel, J R. ""Wireless Energy Lights Bulb from Seven Feet Away—Physicists vow to cut the cord between your laptop battery and the wall socket—with just a simple loop of wire"", ScientificAmerican.com (see http://www.sciam.com/article.cfm?articleid-07511C52-E7F2-99DF-3FA6ED2D7DC9AA2 . . . ) Jun. 7, 2007.

Fildes, Jonathan ""Wireless energy promise powers up"", Science and Technology Report BBC News (see http://news.bbc.co.uk/2/hi/technology/67259585.stm) Jun. 7, 2007.

Highfield, Roger ""Wireless revolution could spell end of plugs"", Science Editor Telegraph.co.uk (see http://www.telegraph.co.uk/news/main.jhtml?xml=/news/2007/06/07/nwirelss107.xml) Jun. 7, 2007.

"Scientists light bulb with 'wireless electricity'", www.chinaview.cn (see http://news.xinhuanet.com/english/2007-06/08/content_6215681.htm) Jun. 2007.

Senge, Miebi ""MIT's wireless electricity for mobile phones"", Vanguard (see http://www.vanguardngr.com/articles/2002/features/gsm/gsm211062007.htm) Jun. 11, 2007.

""Wireless power transfer possible"", PressTV (See http://www.presstv.ir/detail.aspx?id-12754§ionid-3510208) Jun. 11, 2007.

Yariv, Amnon ""Coupled-resonator optical waveguide: a proposal and analysis"", Optics Letters vol. 24, No. 11 Jun. 1, 1999, 711-713.

Kawamura, ""Wireless Transmission of Power and Information Through One High-Frequency Resonant AC Link Inverter for Robot Manipulator Applications"", IEEE 32(3) May/Jun. 1996, 503-508.

"International Application Serial No. PCT/US2010/024199, Search Report and Written Opinion mailed May 14, 2010", PCT/US2010/024199 May 14, 2010, 12.

Sekitani, ""A large-area wireless power transmission sheet using printed organic transistors and plastic MEMS switches"", www.nature.com/naturematerials Published online Apr. 29, 2007.

Apneseth, ""Introducing wireless proximity switches"", ABB Review Apr. 2002.

Karalis, Aristeidis ""Efficient Wireless non-readiative mid-range energy transfer"", Annals of Physics vol. 323 2008, 34-48.

Aoki, T. ""Observation of strong coupling between one atom and a monolithic microresonator"", Nature 443 2006, 671-674.

Chang, Angela ""Recharging, The Wireless Way—Even physicists forget to recharge their cell phones sometimes."", PC Magazine, ABC News Internet Ventures 2006.

Balanis, C A. ""Antenna Theory: Analysis and Design"", 3rd Edition Sections 4.2, 4.3, 5.2, 5.3 Wiley, New Jersey, 2005, 151-255.

Valtchev, ""Efficient Resonant Inductive Coupling Energy Transfer Using New Magnetic and Design Criteria"", IEEE 2005, 1293-1298.

Pendry, J B. ""A Chiral Route to Negative Refraction"", Science 306 2004, 1353-1355.

Vilkomerson, David ""Implantable Doppler System for Self-Monitoring Sascular Grafts"", IEEE Ultrasonics Symposium 2004, 461-465.

Fernandez, C ""A simple dc-dc converter for the power supply of a cochlear implant"", IEEE 2003, 1965-1970.

O'Brien, ""Analysis of Wireless Power Supplies for Industrial Automation Systems"", IEEE 2003, 367-372.

Lee, ""Antenna Circuit Design for RFID Applications"Microchip Technology Inc", AN710 2003, 50 pages.

O'Brien, ""Design of Large Air-Gap Transformers for Wireless Power Supplies"", IEEE 2003, 1257-1562.

Jacob, M V. ""Lithium Tantalate—A High Permittivity Dielectric Material for Microwave Communication Systems"", Proceedings of IEEE TENCON Poster papers 2003, 1362-1366.

""White Paper"", Pwercast LLC Pwercast simply wire free 2003.

Schutz, J ""Load Adaptive Medium Frequency Resonant Power Supply"", IEEE 2002.

Scheible, G ""Novel Wireless Power Supply System for Wireless Communication Devices in Industrial Automation Systems"", IEEE 2002.

"microID 13.56 MHz Design Guide—MCRF355/360 Reader Reference Design", Microchip Technology, Inc. 2001, 24 pages.

Vandevoorde, ""Wireless energy transfer for stand-alone systems: a comparison between low and high power applicability"", Sensors and Actuators A 92 2001, 305-311.

Fenske, ""Dielectric Materials at Microwave Frequencies"", Applied Microwave & Wireless 2000, 92-100.

Jackson, J. D. ""Classical Electrodynamics"", 3rd Edition Sections 1.11, 5.5, 5.17, 6.9, 8.1, 8.8, 9.2, 9.3 Wiley, New York 1999, all.

Yoshihiro, Konishi Microwave Electronic Circuit Technology Chapter 4 (Marcel Dekker, Inc., New York, NY 1998), 145-197.

Staelin, David H. Electromagnetic Waves, Chapters 2,3,4, and 8 Prentice Hall Upper Saddle River, New Jersey 1998, 46-176 and 336-405.

Lee, ""RFID Coil Design"", Microchip Technology, Inc. AN678 1998, 21 Pgs.

Sakamoto, ""A Novel Circuit for Non-Contact Charging Through Electro-Magnetic Coupling"", IEEE 1992, 168-174.

Esser, ""A New Approach to Power Supplies for Robots"", Transactions of Industry Applications vol. 27, No. 5 Sep. / Oct. 1991, 872-875.

Haus, H A. ""Waves and Fields in Optoelectronics"", Coupling of Modes—Resonators and Couplers Chapter 7 Prentice-Hall, New Jersey, 1984, 197-234.

Sensiper, S. "Electromagnetic wave propogation on helical conductors", PhD Thesis Massachusetts Institute of Technology 1951.

Risen, Clay ""Wireless Energy"", The New York Times Dec. 9, 2007.

"International Search Report & WO for PCTUS0959244", PCTUS0959244 Dec. 7, 2009, 1-12.

""In pictures: A year in technology"", BBC News Dec. 28, 2007.

Fildes, Jonathan ""the technology with impact 2007"", BBC News Dec. 27, 2007.

Sekitani, ""A large-area flexible wireless power transmission sheet using printed plastic MLMS switches and organic field-effect transistors"", Dec. 11-13, 2006, 1-3.

Cooks, Gareth "The vision of an MIT physicist: Getting rid of pesky rechargers", Globe Staff Boston.com Dec. 11, 2006.

"International Application Serial No. PCT/US09/58499, Search Report and Written Opinion mailed Dec. 10, 2009", PCT/US09/58499 Dec. 10, 2009.

"ISR and WO for Int'l Appl. No. PCT/US2006/026480", Examiner Susanne Gundlach Dec. 21, 2007.

""Intel CTO Says Gap between Humans, Machines WII Close by 2050"", Intel News Release (see intel.com/.../20080821comp.htm?iid-S . . . ) Printed Nov. 6, 2009.

Cass, Stephen ""Air Power—Wireless data connections are common—now scientists are working on wireless power"", Sponsored by Spectrum (see http://spectrum.ieee.org/computing/hardware/airpower) Nov. 2006.

Freedman, D. H. ""Power on a Chip"", MIT Technology Review Nov. 2004.

""Recharging gadgets without cables"", Infotech Online Printed from infortech.indiatimes.com Nov. 17, 2006.

Tesla, Nikola ""High Frequency Oscillators for Electro-Therapeutic and Other Purposes"", The Electrical Engineer vol. XXVI, No. 50 Nov. 17, 1898.

Morgan, James ""Lab report: Pull the plug for a positive charge"", The Herald, Web Issue 2680 Nov. 16, 2006.

Borenstein, Seth ""Man tries wirelessly boosting batteries"", The Associated Press USA Today Nov. 16, 2006.

Biever, Celeste ""'Evanescent coupling' could power gadgets wirelessly"", NewScientistsTech.com (see http://newscientisttech.com/article.ns?id=dn575&print=true) Nov. 15, 2006.

Lamb, Gregory M. "Look, Ma—no wires! —Electricity broadcast through the air may someday run your home", Staff Writer The Christian Science Monitor (see http://www.csmonitor.com/2006/1116/p14s01-stct.html) Nov. 15, 2006.

Borenstein, Seth ""Man tries wirelessly boosting batteries"", AP Science Writer Boston.com (See http://www.boston.com/business/technology/articles/2006/11/15/man_tries_wirelessly_boosting_batteries) Nov. 15, 2006.

Fildes, Jonathan ""Physics Promises Wireless Power"", Science and Technology Reporter, BBC News Nov. 15, 2006.

(56) References Cited

OTHER PUBLICATIONS

Berardelli, Phil ""Outlets Are Out"", ScienceNOW Daily News, Science Now (See http://sciencenow.sciencemag.org/cgi/content/full/2006/1114/2) Nov. 14, 2006.

""Wireless Energy Transfer Can Potentially Recharge Laptops, Cell Phones Without Cords"", Soljacic, Marin : Massachusetts Institute of Technology and Castelvecchi : American Institute of Physics Nov. 14, 2006 , all.

""Wireless Energy Transfer May Power Devices at a Distance"", ScientificAmerican.com Nov. 14, 2006.

Peterson, Gary ""MIT WiTricity Not So Original After All"", Feed Line No. 9 (See http://www.tfcbooks.com/articles/witricity.htm) printed Nov. 12, 2009 , 1-3.

Soljacic, Marin ""Wireless Non-Radiative Energy Transfer"", Power Point Presentation Massachusetts Institute of Technology Oct. 6, 2005.

Heikkinen, ""Performance and Efficiency of Planar Rectennas for Short-Range Weireless Power Transfer at 2.45 GHz"", Microwave and Optical Technology Letters 31(2) Oct. 20, 2001 , 86-91.

"PCT/US2007/070892—Int'l Prelim Report on Patentability", Oct. 8, 2009.

U.S. Appl. No. 12/613,686, Notice of Allowance mailed Jan. 6, 2011, 10.

ISR on Patentability for Int'l Appl. No. PCT/US2006/026480, PCT/US2006/026480 Jan. 29, 2008.

European Examination Report, Application No. 06 786 588.1-1242 Jan. 15, 2009 , all.

International Search Report & WO for PCT/US09/43970, PCT/US09/43970 Jul. 14, 2009 , all.

"Electricity Unplugged, Feature Wireless Energy", Physics World Feb. 2009 , 23-25.

U.S. Appl. No. 12/613,686, Notice of Allowance mailed Mar. 7, 2011, U.S. Appl. No. 12/613,686 , 27.

U.S. Appl. No. 60/908,383, filed Mar. 27, 2007.

Machine Translation for Japanese Patent JPH09182323 which published on Jul. 11, 1997, 8 pages.

Budhia, Mickel et al.,"A New IPT Magnetic Coupler for Electric Vehicle Charging Systems",IECON 2010—36th Annual Conference on IEEE Industrial Electronics Society, Glendale, AZ,Nov. 7-10, 2010,pp. 2487-2492.

Budhia, Mickel et al.,"Development and evaluation of single sided flux couplers for contactless electric vehicle charging", 2011 IEEE Energy Conversion Congress and Exposition (ECCE), Phoenix, AZ,Sep. 17-22, 2011,pp. 614-621.

Budhia, Mickel et al.,"Development of a Single-Sided Flux Magnetic Coupler for Electric Vehicle IPT", IEEE Transactions on Industrial Electronics, vol. 60, No. 1, Jan. 2013, pp. 318-328.

Jackson, J. D., "Classical Electrodynamics", 3rd Edition, Wiley, New York,1999,pp. 201-203.

Kesler, Dr. Morris, "Highly Resonant Wireless Power Transfer: Safe, Efficient, and over Distance", WiTricity Corporation, WiTricity Corporation, 2013,32 Pages.

PCT/US2012/040184, International Application Serial No. PCT/US2012/040184, International Preliminary Report on Patentability and Written Opinion mailed Dec. 27, 2013, Witricity Corporation, 7 Pages.

PCT/US2012/047844, International Application Serial No. PCT/US2012/047844, International Preliminary Report on Patentability with Written Opinion mailed Jan. 30, 2014, Witricity Corporation et al, 6 Pages.

PCT/US2012/049777, International Application Serial No. PCT/US2012/049777, International Preliminary Report on Patentability mailed Feb. 13, 2014, Witricity Corporation et at, 6 Pages.

PCT/US2012/054490, International Application Serial No. PCT/US2012/054490, International Preliminary Report on Patentability and Written Opinion mailed Mar. 20, 2014, Witricity Corporation et al, 8 Pages.

PCT/US2013/033599, International Application Serial No. PCT/US2013/033599, International Search Report and Written Opinion mailed Jul. 25, 2013, Witricity Corporation, 13 pages.

PCT/US2013/048210, International Application Serial No. PCT/US2013/048210, International Search Report mailed Oct. 15, 2013, Witricity Corporation, 12-Pages.

Tang, S.C et al., "Evaluation of the Shielding Effects on Printed-Circuit-Board Transformers Using Ferrite Plates and Copper Sheets", IEEE Transactions on Power Electronics, vol. 17, No. 6, Nov. 2002, pp. 1080-1088.

Villeneuve, Pierre R. et al., "Microcavities in photonic crystals: Mode symmetry, tunability, and coupling efficiency", Physical Review B, vol. 54, No. 11, Sep. 15, 1996, pp. 7837-7842.

"Next Little Thing 2010 Electricity without wires", CNN Money (See money.cnn.com/galleries/2009/smallbusiness/0911/gallery.next_little_thing_2010.smb/) (dated Nov. 30, 2009).

Ahmadian, M. et al., "Miniature Transmitter for Implantable Micro Systems", *Proceedings of the 25th Annual International Conference of the IEEE EMBS* Cancun, Mexico, pp. 3028-3031 (Sep. 17-21, 2003).

Eisenberg, Anne, "Automatic Recharging, From a Distance", The New York Times, (see www.nytimes.com/2012/03/11/business/built-in-wireless-chargeing-for-electronic-devices.html?_r=0) (published on Mar. 10, 2012).

Fan, Shanhui et al., "Rate-Equation Analysis of Output Efficiency and Modulation Rate of Photomic-Crystal Light-Emitting Diodes", IEEE Journal of Quantum Electronics, vol. 36(10):1123-1130 (Oct. 2000).

Ferris, David, "How Wireless Charging Will Make Life Simpler (And Greener)", Forbes (See forbes.com/sites/davidferris/2012/07/24/how-wireless-charging-will-make-life-simpler-and-greener/print/) (dated Jul. 24, 2012).

Fildes, J., "The technology with impact 2007", BBC News, (Dec. 27, 2007) 3 pages.

Finkenzeller, Klaus, "RFID Handbook—Fundamentals and Applications in Contactless Smart Cards", Nikkan Kohgyo-sya, Kanno Taihei, first version, pp. 32-37, 253 (Aug. 21, 2001).

Finkenzeller, Klaus, "RFID Handbook (2nd Edition)", The Nikkan Kogyo Shimbun, Ltd., pp. 19, 20, 38, 39, 43, 44, 62, 63, 67, 68, 87, 88, 291, 292 (Published on May 31, 2004).

Ho, S. L. et al., "A Comparative Study Between Novel Witricity and Traditional Inductive Magnetic Coupling in Wireless Charging", IEEE Transactions on Magnetics, vol. 47(5):1522-1525 (May 2011).

Kurs, A. et al., "Simultaneous mid-range power transfer to multiple devices", *Applied Physics Letters*, vol. 96, No. 044102 (2010).

Moskvitch, Katia, "Wireless charging—the future for electric cars?", BBC News Technology (See www.bbc.co.uk/news/technology-14183409) (dated Jul. 21, 2011).

Schneider, David, "Electrons Unplugged. Wireless power at a distance is still far away", *IEEE Spectrum*, pp. 35-39 (May 2010).

Stewart, W., "The Power to Set you Free", Science, vol. 317:55-56 (Jul. 6, 2007).

Yates, David C. et al., "Optimal Transmission Frequency for Ultralow-Power Short-Range Radio Links", IEEE Transactions on Circuits and Systems—1, Regular Papers, vol. 51:1405-1413 (Jul. 2004).

Ziaie, Babak et al., "A Low-Power Miniature Transmitter Using A Low-Loss Silicon Platform for Biotelemetry", *Proceedings—19th International Conference IEEE/EMBS*, pp. 2221-2224, (Oct. 30-Nov. 2, 1997) 4 pages.

Mourad, Rasem, Final Office Action, U.S. Appl. No. 13/279,014, mailed on Mar. 24, 2014, 17 pages.

Mourad, Rasem, Non-Final Office Action, U.S. Appl. No. 13/279,014, mailed on Sep. 13, 2013, 12 pages.

Fish & Richardson, Reply to Action of Mar. 24, 2014, U.S. Appl. No. 13/279,014, filed May 14, 2014, 8 pages.

Fish & Richardson, Reply to Action of Sep. 13, 2013, U.S. Appl. No. 13/279,014, filed Feb. 13, 2014, 8 pages.

\* cited by examiner

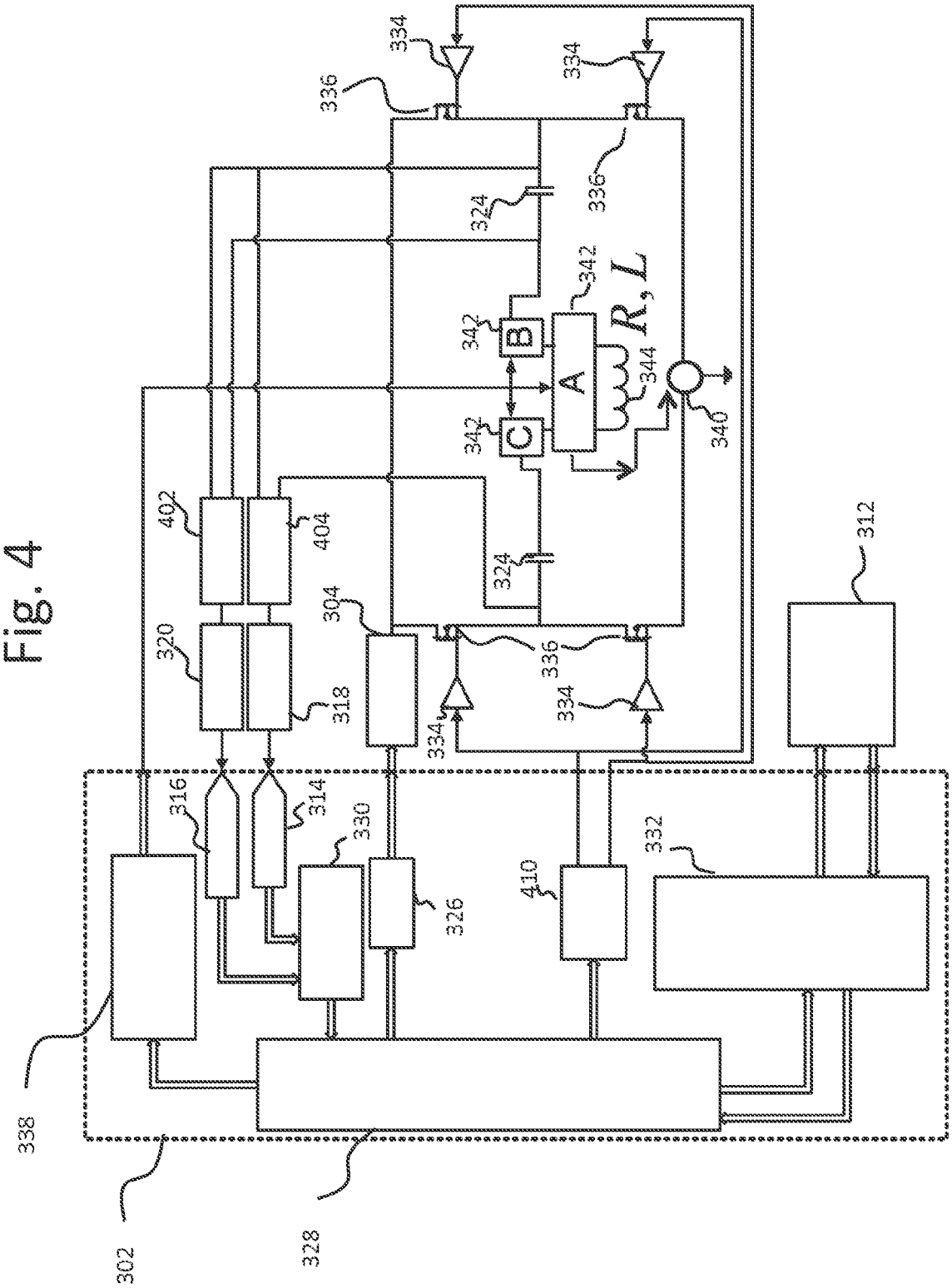

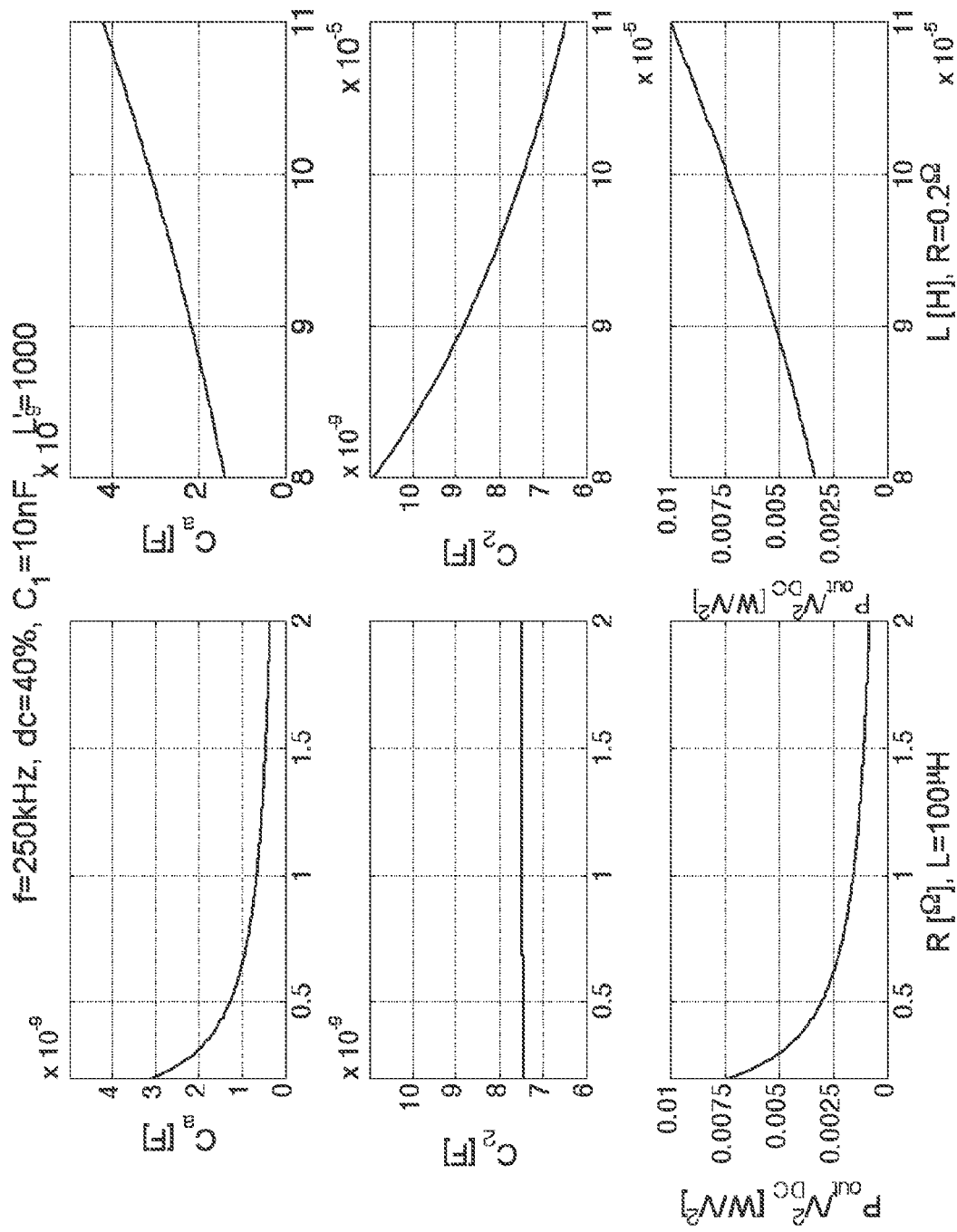

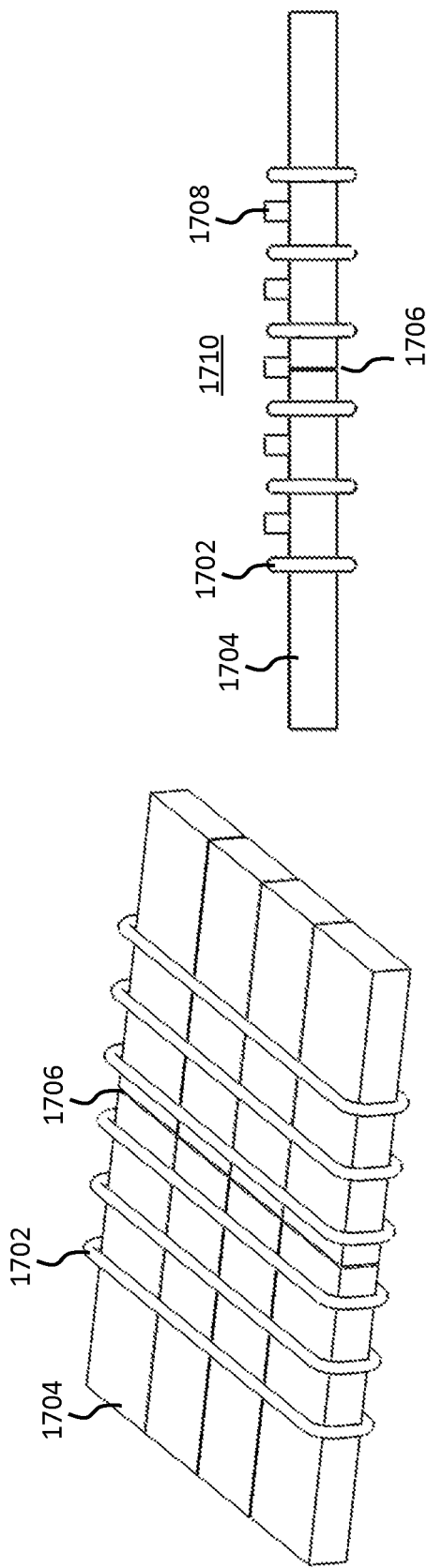
Fig. 17A
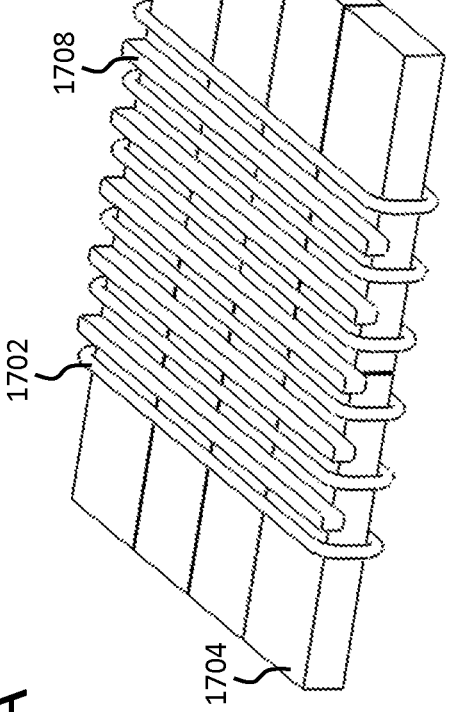
Fig. 17B
Fig. 17C

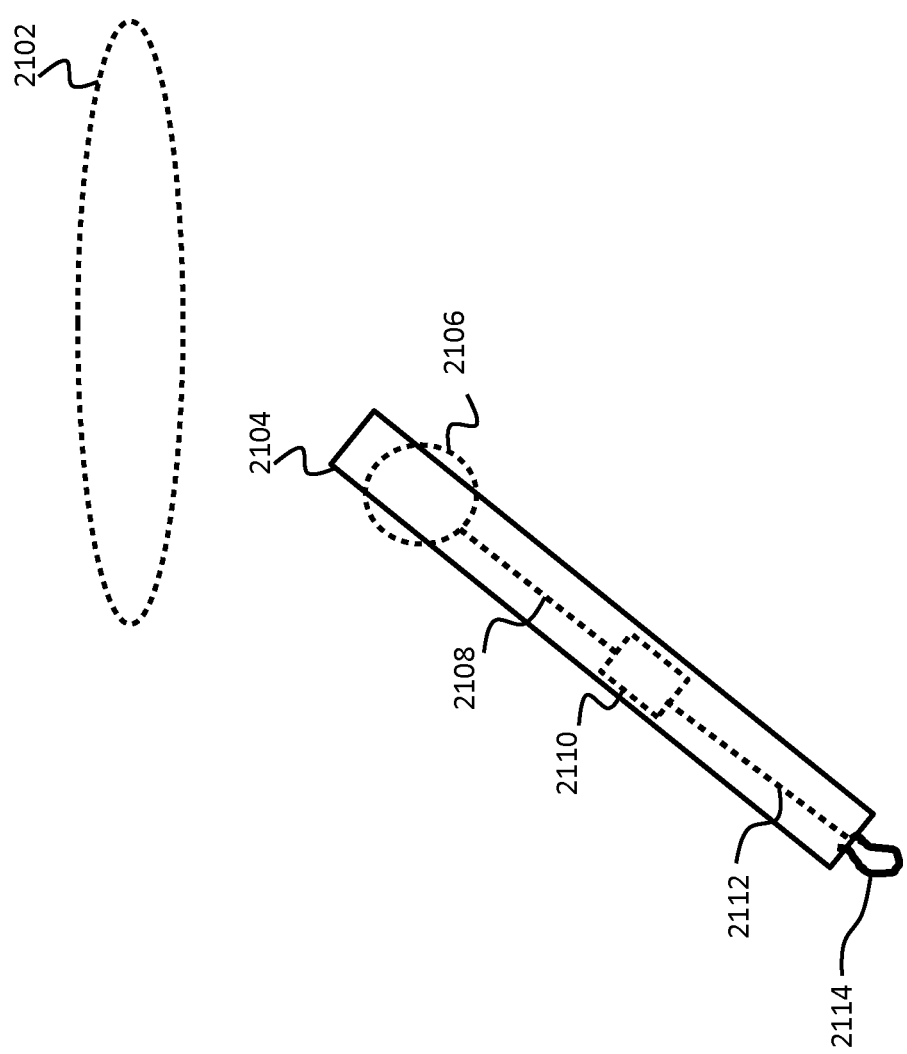

WIRELESS ENERGY TRANSFER FOR MEDICAL APPLICATIONS

CROSS-REFERENCE TO RELATED APPLICATIONS

This application claims the benefit of U.S. Provisional Appl. No. 61/326,051 filed Apr. 20, 2010.

This application is a continuation-in-part of U.S. patent application Ser. No. 13/021,965 filed Feb. 7, 2011 which is a continuation-in-part of U.S. patent application Ser. No. 12/986,018 filed Jan. 6, 2011, which claims the benefit of U.S. Provisional Appl. No. 61/292,768 filed Jan. 6, 2010.

The Ser. No. 12/986,018 application is a continuation-in-part of U.S. patent application Ser. No. 12/789,611 filed May 28, 2010.

The Ser. No. 12/789,611 application is a continuation-in-part of U.S. patent application Ser. No. 12/770,137 filed Apr. 29, 2010 which claims the benefit of U.S. Provisional Application No. 61/173,747 filed Apr. 29, 2009.

The Ser. No. 12/770,137 application is a continuation-in-part of U.S. application Ser. No. 12/767,633 filed Apr. 26, 2010, which claims the benefit of U.S. Provisional Application No. 61/172,633 filed Apr. 24, 2009.

Application Ser. No. 12/767,633 is a continuation-in-part of U.S. application Ser. No. 12/759,047 filed Apr. 13, 2010 which is a continuation-in-part of U.S. application Ser. No. 12/757,716 filed Apr. 9, 2010, which is a continuation-in-part of U.S. application Ser. No. 12/749,571 filed Mar. 30, 2010.

The Ser. No. 12/749,571 application is a continuation-in-part of the following U.S. Applications: U.S. application Ser. No. 12/639,489 filed Dec. 16, 2009; and U.S. application Ser. No. 12/647,705 filed Dec. 28, 2009.

The Ser. No. 12/749,571 application a continuation-in-part of U.S. application Ser. No. 12/567,716 filed Sep. 25, 2009, which claims the benefit of the following U.S. patent applications: U.S. App. No. 61/100,721 filed Sep. 27, 2008; U.S. App. No. 61/108,743 filed Oct. 27, 2008; U.S. App. No. 61/147,386 filed Jan. 26, 2009; U.S. App. No. 61/152,086 filed Feb. 12, 2009; U.S. App. No. 61/178,508 filed May 15, 2009; U.S. App. No. 61/182,768 filed Jun. 1, 2009; U.S. App. No. 61/121,159 filed Dec. 9, 2008; U.S. App. No. 61/142,977 filed Jan. 7, 2009; U.S. App. No. 61/142,885 filed Jan. 6, 2009; U.S. App. No. 61/142,796 filed Jan. 6, 2009; U.S. App. No. 61/142,889 filed Jan. 6, 2009; U.S. App. No. 61/142,880 filed Jan. 6, 2009; U.S. App. No. 61/142,818 filed Jan. 6, 2009; U.S. App. No. 61/142,887 filed Jan. 6, 2009; U.S. App. No. 61/156,764 filed Mar. 2, 2009; U.S. App. No. 61/143,058 filed Jan. 7, 2009; U.S. App. No. 61/163,695 filed Mar. 26, 2009; U.S. App. No. 61/172,633 filed Apr. 24, 2009; U.S. App. No. 61/169,240 filed Apr. 14, 2009, U.S. App. No. 61/173,747 filed Apr. 29, 2009.

The Ser. No. 12/757,716 application is a continuation-in-part of U.S. application Ser. No. 12/721,118 filed Mar. 10, 2010, which is a continuation-in-part of U.S. application Ser. No. 12/705,582 filed Feb. 13, 2010 which claims the benefit of U.S. Provisional Application No. 61/152,390 filed Feb. 13, 2009.

Each of the foregoing applications is incorporated herein by reference in its entirety.

BACKGROUND

1. Field

This disclosure relates to wireless energy transfer, methods, systems and apparati to accomplish such transfer, and applications.

2. Description of the Related Art

Energy or power may be transferred wirelessly using a variety of techniques as detailed, for example, in commonly owned U.S. patent application Ser. No. 12/789,611 published on Sep. 23, 2010 as U.S. Pat. Pub. No. 2010/0237709 and entitled "RESONATOR ARRAYS FOR WIRELESS ENERGY TRANSFER," and U.S. patent application Ser. No. 12/722,050 published on Jul. 22, 2010 as U.S. Pat. Pub. No. 2010/0181843 and entitled "WIRELESS ENERGY TRANSFER FOR REFRIGERATOR APPLICATION" the contents of which are incorporated in their entirety as if fully set forth herein. Prior art wireless energy transfer systems have been limited by a variety of factors including concerns over user safety, low energy transfer efficiencies and restrictive physical proximity/alignment tolerances for the energy supply and sink components.

Medical equipment and surgical devices are often troublesome and cumbersome due to their restrictive and cumbersome wiring. Traditional electronic patient monitoring systems, drug delivery systems, computer carts, beds, patient positioning devices require a wired connection for power to operate or recharge their batteries. The large number of devices and equipment makes cable management difficult especially when the equipment of often moved and repositioned which can result in cable tangles.

Problems with power delivery and cable management may also exist for surgical devices. Surgical devices often need to be manipulated in very confined areas within the or around the patient. Constant manipulation may result in cable management problems as multiple cables can be intertwined limiting their operational range and movement.

Therefore a need exists for methods and designs for energy delivery to medical equipment and surgical devices.

SUMMARY

Various systems and processes, in various embodiments, provide wireless energy transfer using coupled resonators. In some embodiments, the resonator structures may require or benefit from thermal management of the components of the resonators. Resonator components may require cooling to prevent their temperatures from exceeding a critical temperature. The features of such embodiments are general and may be applied to a wide range of resonators, regardless of the specific examples discussed herein.

In embodiments, a magnetic resonator may comprise some combination of inductors and capacitors. Additional circuit elements such as capacitors, inductors, resistors, switches, and the like, may be inserted between a magnetic resonator and a power source, and/or between a magnetic resonator and a power load. In this disclosure, the conducting coil that comprises the high-Q inductive loop of the resonator may be referred to as the inductor and/or the inductive load. The inductive load may also refer to the inductor when it is wirelessly coupled (through a mutual inductance) to other system or extraneous objects. In this disclosure, circuit elements other than the inductive load may be referred to as being part of an impedance matching network or IMN. It is to be understood that all, some, or none of the elements that are referred to as being part of an impedance matching network may be part of the magnetic resonator. Which elements are part of the resonator and which are separate from the resonator will depend on the specific magnetic resonator and wireless energy transfer system design.

In one aspect, medical equipment is fitted with device resonators to wirelessly capture energy from source resonators integrated into walls, floors, or other equipment.

In another aspect surgical devices are powered wirelessly. In some embodiments the surgical devices are configured to use the oscillating electrical energy of the device resonator without requiring a separate AC to DC or AC to AC converters in the device.

Unless otherwise indicated, this disclosure uses the terms wireless energy transfer, wireless power transfer, wireless power transmission, and the like, interchangeably. Those skilled in the art will understand that a variety of system architectures may be supported by the wide range of wireless system designs and functionalities described in this application.

In the wireless energy transfer systems described herein, power may be exchanged wirelessly between at least two resonators. Resonators may supply, receive, hold, transfer, and distribute energy. Sources of wireless power may be referred to as sources or supplies and receivers of wireless power may be referred to as devices, receivers and power loads. A resonator may be a source, a device, or both, simultaneously or may vary from one function to another in a controlled manner. Resonators configured to hold or distribute energy that do not have wired connections to a power supply or power drain may be called repeaters.

The resonators of the wireless energy transfer systems of this invention are able to transfer power over distances that are large compared to the size of the resonators themselves. That is, if the resonator size is characterized by the radius of the smallest sphere that could enclose the resonator structure, the wireless energy transfer system of this invention can transfer power over distances greater than the characteristic size of a resonator. The system is able to exchange energy between resonators where the resonators have different characteristic sizes and where the inductive elements of the resonators have different sizes, different shapes, are comprised of different materials, and the like.

The wireless energy transfer systems of this invention may be described as having a coupling region, an energized area or volume, all by way of describing that energy may be transferred between resonant objects that are separated from each other, they may have variable distance from each other, and that may be moving relative to each other. In some embodiments, the area or volume over which energy can be transferred is referred to as the active field area or volume. In addition, the wireless energy transfer system may comprise more than two resonators that may each be coupled to a power source, a power load, both, or neither.

Wirelessly supplied energy may be used to power electric or electronic equipment, recharge batteries or charge energy storage units. Multiple devices may be charged or powered simultaneously or power delivery to multiple devices may be serialized such that one or more devices receive power for a period of time after which power delivery may be switched to other devices. In various embodiments, multiple devices may share power from one or more sources with one or more other devices either simultaneously, or in a time multiplexed manner, or in a frequency multiplexed manner, or in a spatially multiplexed manner, or in an orientation multiplexed manner, or in any combination of time and frequency and spatial and orientation multiplexing. Multiple devices may share power with each other, with at least one device being reconfigured continuously, intermittently, periodically, occasionally, or temporarily, to operate as a wireless power source. Those of ordinary skill in the art will understand that there are a variety of ways to power and/or charge devices applicable to the technologies and applications described herein.

This disclosure references certain individual circuit components and elements such as capacitors, inductors, resistors, diodes, transformers, switches and the like; combinations of these elements as networks, topologies, circuits, and the like; and objects that have inherent characteristics such as "self-resonant" objects with capacitance or inductance distributed (or partially distributed, as opposed to solely lumped) throughout the entire object. It would be understood by one of ordinary skill in the art that adjusting and controlling variable components within a circuit or network may adjust the performance of that circuit or network and that those adjustments may be described generally as tuning, adjusting, matching, correcting, and the like. Other methods to tune or adjust the operating point of the wireless power transfer system may be used alone, or in addition to adjusting tunable components such as inductors and capacitors, or banks of inductors and capacitors. Those skilled in the art will recognize that a particular topology discussed in this disclosure can be implemented in a variety of other ways.

Unless otherwise defined, all technical and scientific terms used herein have the same meaning as commonly understood by one of ordinary skill in the art to which this disclosure belongs. In case of conflict with publications, patent applications, patents, and other references mentioned or incorporated herein by reference, the present specification, including definitions, will control.

Any of the features described above may be used, alone or in combination, without departing from the scope of this disclosure. Other features, objects, and advantages of the systems and methods disclosed herein will be apparent from the following detailed description and figures.

BRIEF DESCRIPTION OF FIGURES

FIG. 4 is a block diagram of a wireless source with a differential amplifier.

FIG. 10 shows plots of the effects of changes of parameters of a wireless power source.

FIG. 17A is a resonator with a block of magnetic material comprising smaller individual tiles and 17B and 17C is the resonator with additional strips of thermally conductive material used for thermal management.

FIG. 21 is a diagram of a wirelessly powered cauterizing tool.

DETAILED DESCRIPTION

Figure 1:
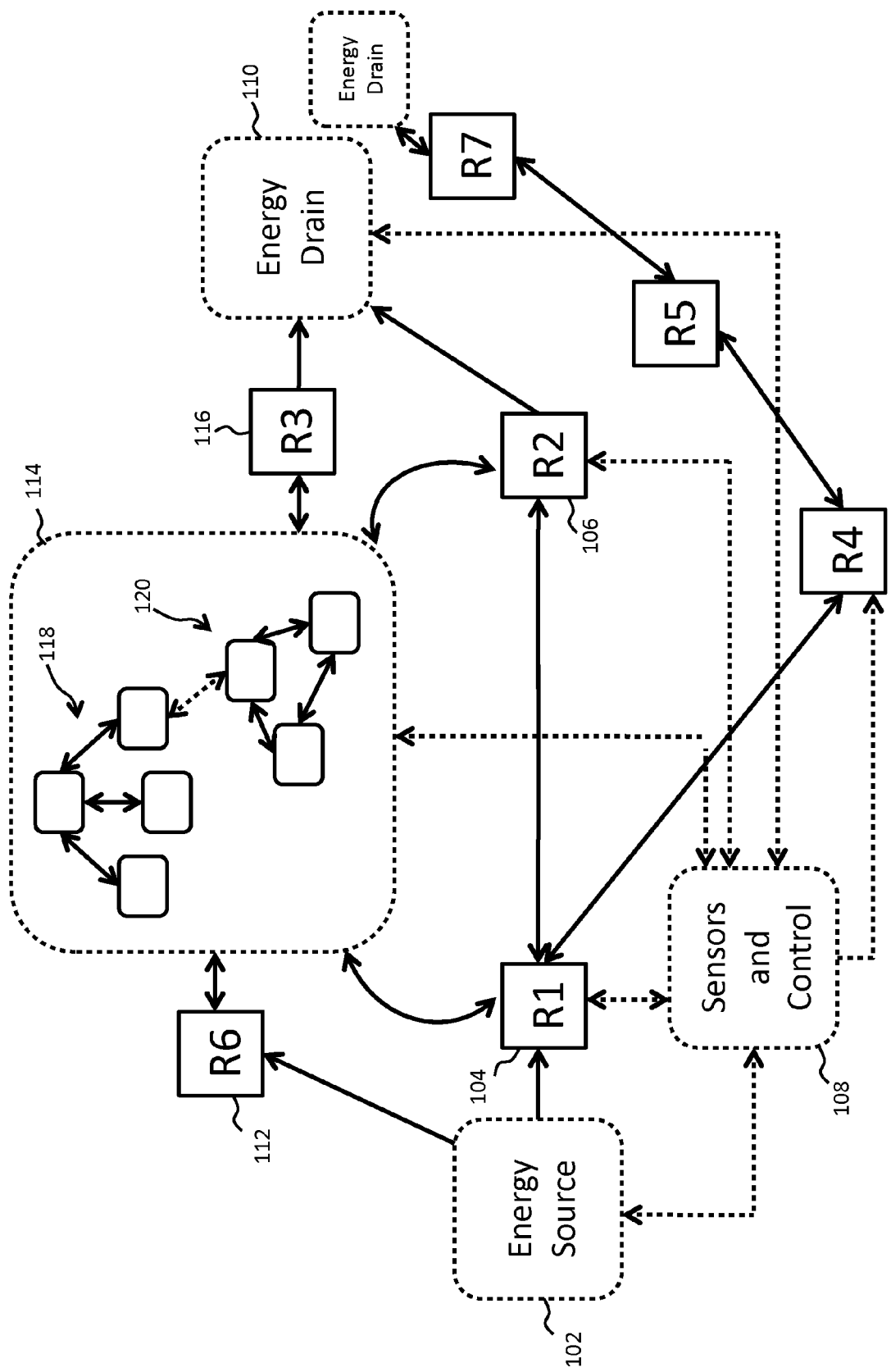
FIG. 1 is a system block diagram of wireless energy transfer configurations.

As described above, this disclosure relates to wireless energy transfer using coupled electromagnetic resonators. However, such energy transfer is not restricted to electromagnetic resonators, and the wireless energy transfer systems described herein are more general and may be implemented using a wide variety of resonators and resonant objects.

As those skilled in the art will recognize, important considerations for resonator-based power transfer include resonator efficiency and resonator coupling. Extensive discussion of such issues, e.g., coupled mode theory (CMT), coupling coefficients and factors, quality factors (also referred to as Q-factors), and impedance matching is provided, for example, in U.S. patent application Ser. No. 12/789,611 published on Sep. 23, 2010 as US 20100237709 and entitled "RESONATOR ARRAYS FOR WIRELESS ENERGY TRANSFER," and U.S. patent application Ser. No. 12/722,050 published on Jul. 22, 2010 as US 20100181843 and entitled "WIRELESS ENERGY TRANSFER FOR REFRIGERATOR APPLICATION" and incorporated herein by reference in its entirety as if fully set forth herein.

A resonator may be defined as a resonant structure that can store energy in at least two different forms, and where the stored energy oscillates between the two forms. The resonant structure will have a specific oscillation mode with a resonant (modal) frequency, f, and a resonant (modal) field. The angular resonant frequency, $\omega$, may be defined as $\omega=2\pi f$, the resonant period, T, may be defined as $T=1/f=2\pi/\omega$, and the resonant wavelength, $\lambda$, may be defined as $\lambda=c/f$, where c is the speed of the associated field waves (light, for electromagnetic resonators). In the absence of loss mechanisms, coupling mechanisms or external energy supplying or draining mechanisms, the total amount of energy stored by the resonator, W, would stay fixed, but the form of the energy would oscillate between the two forms supported by the resonator, wherein one form would be maximum when the other is minimum and vice versa.

For example, a resonator may be constructed such that the two forms of stored energy are magnetic energy and electric energy. Further, the resonator may be constructed such that the electric energy stored by the electric field is primarily confined within the structure while the magnetic energy stored by the magnetic field is primarily in the region surrounding the resonator. In other words, the total electric and magnetic energies would be equal, but their localization would be different. Using such structures, energy exchange between at least two structures may be mediated by the resonant magnetic near-field of the at least two resonators. These types of resonators may be referred to as magnetic resonators.

An important parameter of resonators used in wireless power transmission systems is the Quality Factor, or Q-factor, or Q, of the resonator, which characterizes the energy decay and is inversely proportional to energy losses of the resonator. It may be defined as $Q=\omega*W/P$, where P is the time-averaged power lost at steady state. That is, a resonator with a high-Q has relatively low intrinsic losses and can store energy for a relatively long time. Since the resonator loses energy at its intrinsic decay rate, $2\Gamma$, its Q, also referred to as its intrinsic Q, is given by $Q=\omega/2\Gamma$. The quality factor also represents the number of oscillation periods, T, it takes for the energy in the resonator to decay by a factor of $e^{-2\pi}$. Note that the quality factor or intrinsic quality factor or Q of the resonator is that due only to intrinsic loss mechanisms. The Q of a resonator connected to, or coupled to a power generator, g, or load, l, may be called the "loaded quality factor" or the "loaded Q". The Q of a resonator in the presence of an extraneous object that is not intended to be part of the energy transfer system may be called the "perturbed quality factor" or the "perturbed Q".

Resonators, coupled through any portion of their near-fields may interact and exchange energy. The efficiency of this energy transfer can be significantly enhanced if the resonators operate at substantially the same resonant frequency. By way of example, but not limitation, imagine a source resonator with $Q_s$, and a device resonator with $Q_d$. High-Q wireless energy transfer systems may utilize resonators that are high-Q. The Q of each resonator may be high. The geometric mean of the resonator Q's, $\sqrt{Q_s Q_d}$ may also or instead be high.

The coupling factor, k, is a number between $0 \leq |k| \leq 1$, and it may be independent (or nearly independent) of the resonant frequencies of the source and device resonators, when those are placed at sub-wavelength distances. Rather the coupling factor k may be determined mostly by the relative geometry and the distance between the source and device resonators where the physical decay-law of the field mediating their coupling is taken into account. The coupling coefficient used in CMT, $\kappa = k\sqrt{\omega_s \omega_d}/2$, may be a strong function of the resonant frequencies, as well as other properties of the resonator structures. In applications for wireless energy transfer utilizing the near-fields of the resonators, it is desirable to have the size of the resonator be much smaller than the resonant wavelength, so that power lost by radiation is reduced. In some embodiments, high-Q resonators are sub-wavelength structures. In some electromagnetic embodiments, high-Q resonator structures are designed to have resonant frequencies higher than 100 kHz. In other embodiments, the resonant frequencies may be less than 1 GHz.

In exemplary embodiments, the power radiated into the far-field by these sub wavelength resonators may be further reduced by lowering the resonant frequency of the resonators and the operating frequency of the system. In other embodiments, the far field radiation may be reduced by arranging for the far fields of two or more resonators to interfere destructively in the far field.

In a wireless energy transfer system a resonator may be used as a wireless energy source, a wireless energy capture device, a repeater or a combination thereof. In embodiments a resonator may alternate between transferring energy, receiving energy or relaying energy. In a wireless energy transfer system one or more magnetic resonators may be coupled to an energy source and be energized to produce an oscillating magnetic near-field. Other resonators that are within the oscillating magnetic near-fields may capture these fields and convert the energy into electrical energy that may be used to power or charge a load thereby enabling wireless transfer of useful energy.

The so-called "useful" energy in a useful energy exchange is the energy or power that must be delivered to a device in order to power or charge it at an acceptable rate. The transfer efficiency that corresponds to a useful energy exchange may be system or application-dependent. For example, high power vehicle charging applications that transfer kilowatts of power may need to be at least 80% efficient in order to supply useful amounts of power resulting in a useful energy exchange sufficient to recharge a vehicle battery without significantly heating up various components of the transfer system. In some consumer electronics applications, a useful energy exchange may include any energy transfer efficiencies greater than 10%, or any other amount acceptable to keep rechargeable batteries "topped off" and running for long periods of time. In implanted medical device applications, a useful energy exchange may be any exchange that does not harm the patient but that extends the life of a battery or wakes up a sensor or monitor or stimulator. In such applications, 100 mW of power or less may be useful. In distributed sensing applications, power transfer of microwatts may be useful, and transfer efficiencies may be well below 1%.

A useful energy exchange for wireless energy transfer in a powering or recharging application may be efficient, highly efficient, or efficient enough, as long as the wasted energy levels, heat dissipation, and associated field strengths are within tolerable limits and are balanced appropriately with related factors such as cost, weight, size, and the like.

The resonators may be referred to as source resonators, device resonators, first resonators, second resonators, repeater resonators, and the like. Implementations may include three (3) or more resonators. For example, a single source resonator may transfer energy to multiple device resonators or multiple devices. Energy may be transferred from a first device to a second, and then from the second device to the third, and so forth. Multiple sources may transfer energy to a single device or to multiple devices connected to a single device resonator or to multiple devices connected to multiple device resonators. Resonators may serve alternately or simultaneously as sources, devices, and/or they may be used to relay power from a source in one location to a device in another location. Intermediate electromagnetic resonators may be used to extend the distance range of wireless energy transfer systems and/or to generate areas of concentrated magnetic near-fields. Multiple resonators may be daisy-chained together, exchanging energy over extended distances and with a wide range of sources and devices. For example, a source resonator may transfer power to a device resonator via several repeater resonators. Energy from a source may be transferred to a first repeater resonator, the first repeater resonator may transfer the power to a second repeater resonator and the second to a third and so on until the final repeater resonator transfers its energy to a device resonator. In this respect the range or distance of wireless energy transfer may be extended and/or tailored by adding repeater resonators. High power levels may be split between multiple sources, transferred to multiple devices and recombined at a distant location.

The resonators may be designed using coupled mode theory models, circuit models, electromagnetic field models, and the like. The resonators may be designed to have tunable characteristic sizes. The resonators may be designed to handle different power levels. In exemplary embodiments, high power resonators may require larger conductors and higher current or voltage rated components than lower power resonators.

FIG. 1 shows a diagram of exemplary configurations and arrangements of a wireless energy transfer system. A wireless energy transfer system may include at least one source resonator (R1) 104 (optionally R6, 112) coupled to an energy source 102 and optionally a sensor and control unit 108. The energy source may be a source of any type of energy capable of being converted into electrical energy that may be used to drive the source resonator 104. The energy source may be a battery, a solar panel, the electrical mains, a wind or water turbine, an electromagnetic resonator, a generator, and the like. The electrical energy used to drive the magnetic resonator is converted into oscillating magnetic fields by the resonator. The oscillating magnetic fields may be captured by other resonators which may be device resonators (R2) 106, (R3) 116 that are optionally coupled to an energy drain 110. The oscillating fields may be optionally coupled to repeater resonators (R4, R5) that are configured to extend or tailor the wireless energy transfer region. Device resonators may capture the magnetic fields in the vicinity of source resonator(s), repeater resonators and other device resonators and convert them into electrical energy that may be used by an energy drain. The energy drain 110 may be an electrical, electronic, mechanical or chemical device and the like configured to receive electrical energy. Repeater resonators may capture magnetic fields in the vicinity of source, device and repeater resonator(s) and may pass the energy on to other resonators.

A wireless energy transfer system may comprise a single source resonator 104 coupled to an energy source 102 and a single device resonator 106 coupled to an energy drain 110. In embodiments a wireless energy transfer system may comprise multiple source resonators coupled to one or more energy sources and may comprise multiple device resonators coupled to one or more energy drains.

In embodiments the energy may be transferred directly between a source resonator 104 and a device resonator 106. In other embodiments the energy may be transferred from one or more source resonators 104, 112 to one or more device resonators 106, 116 via any number of intermediate resonators which may be device resonators, source resonators, repeater resonators, and the like. Energy may be transferred via a network or arrangement of resonators 114 that may include subnetworks 118, 120 arranged in any combination of topologies such as token ring, mesh, ad hoc, and the like.

In embodiments the wireless energy transfer system may comprise a centralized sensing and control system 108. In embodiments parameters of the resonators, energy sources, energy drains, network topologies, operating parameters, etc. may be monitored and adjusted from a control processor to meet specific operating parameters of the system. A central control processor may adjust parameters of individual components of the system to optimize global energy transfer efficiency, to optimize the amount of power transferred, and the like. Other embodiments may be designed to have a substantially distributed sensing and control system. Sensing and control may be incorporated into each resonator or group of resonators, energy sources, energy drains, and the like and may be configured to adjust the parameters of the individual components in the group to maximize the power delivered, to maximize energy transfer efficiency in that group and the like.

In embodiments, components of the wireless energy transfer system may have wireless or wired data communication links to other components such as devices, sources, repeaters, power sources, resonators, and the like and may transmit or receive data that can be used to enable the distributed or centralized sensing and control. A wireless communication channel may be separate from the wireless energy transfer channel, or it may be the same. In one embodiment the resonators used for power exchange may also be used to exchange information. In some cases, information may be exchanged by modulating a component in a source or device circuit and sensing that change with port parameter or other monitoring equipment. Resonators may signal each other by tuning, changing, varying, dithering, and the like, the resonator parameters such as the impedance of the resonators which may affect the reflected impedance of other resonators in the system. The systems and methods described herein may enable the simultaneous transmission of power and communication signals between resonators in wireless power transmission systems, or it may enable the transmission of power and communication signals during different time periods or at different frequencies using the same magnetic fields that are used during the wireless energy transfer. In other embodiments wireless communication may be enabled with a separate wireless communication channel such as WiFi, Bluetooth, Infrared, and the like.

In embodiments, a wireless energy transfer system may include multiple resonators and overall system performance may be improved by control of various elements in the system. For example, devices with lower power requirements may tune their resonant frequency away from the resonant frequency of a high-power source that supplies power to devices with higher power requirements. In this way, low and high power devices may safely operate or charge from a single high power source. In addition, multiple devices in a charging zone may find the power available to them regulated according to any of a variety of consumption control algorithms such as First-Come-First-Serve, Best Effort, Guaranteed Power, etc. The power consumption algorithms may be hierarchical in nature, giving priority to certain users or types of devices, or it may support any number of users by equally sharing the power that is available in the source. Power may be shared by any of the multiplexing techniques described in this disclosure.

Figure 2:
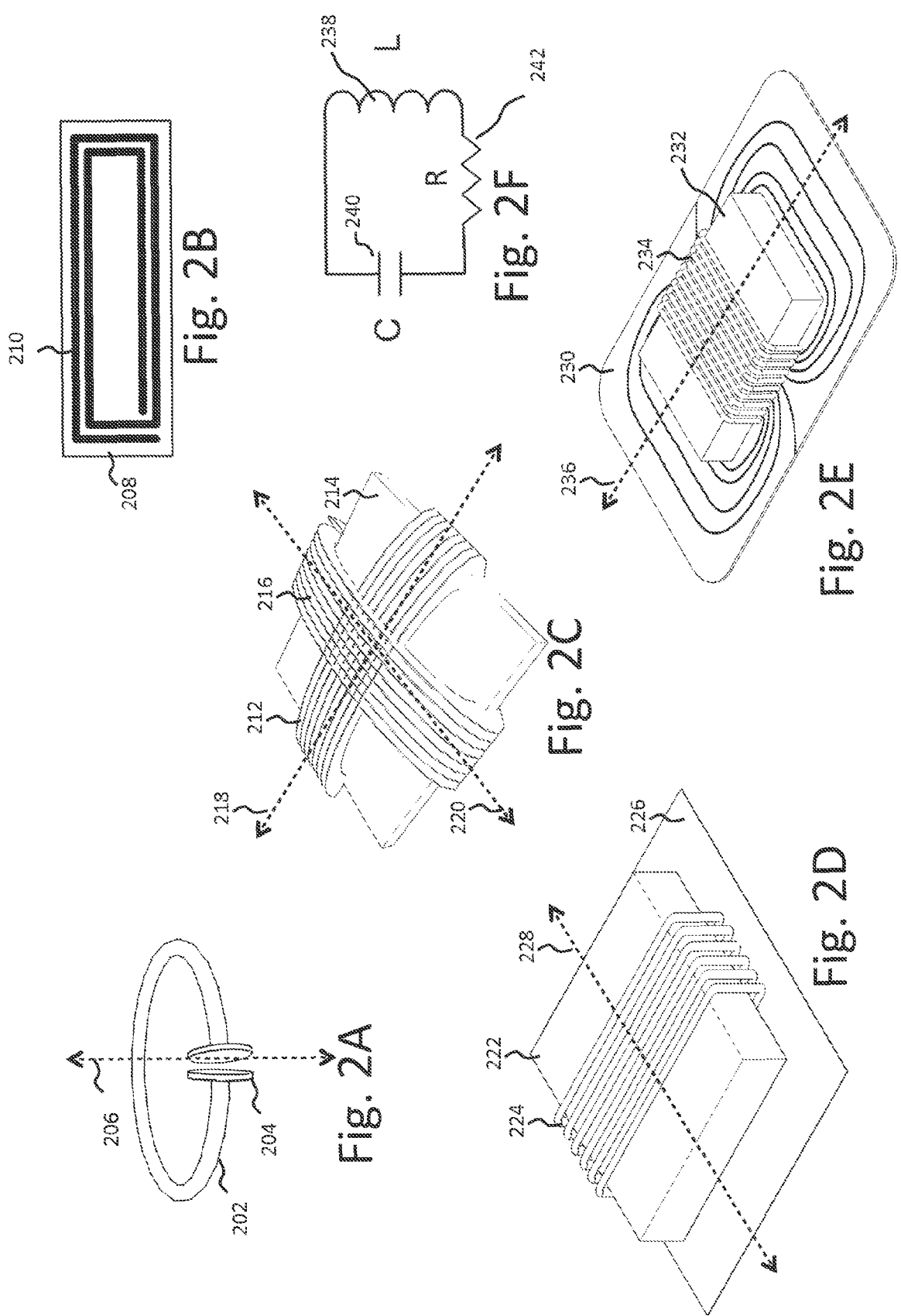
FIGS. 2A-2F are exemplary structures and schematics of simple resonator structures.

In embodiments electromagnetic resonators may be realized or implemented using a combination of shapes, structures, and configurations. Electromagnetic resonators may include an inductive element, a distributed inductance, or a combination of inductances with a total inductance, L, and a capacitive element, a distributed capacitance, or a combination of capacitances, with a total capacitance, C. A minimal circuit model of an electromagnetic resonator comprising capacitance, inductance and resistance, is shown in FIG. 2F. The resonator may include an inductive element 238 and a capacitive element 240. Provided with initial energy, such as electric field energy stored in the capacitor 240, the system will oscillate as the capacitor discharges transferring energy into magnetic field energy stored in the inductor 238 which in turn transfers energy back into electric field energy stored in the capacitor 240. Intrinsic losses in these electromagnetic resonators include losses due to resistance in the inductive and capacitive elements and to radiation losses, and are represented by the resistor, R, 242 in FIG. 2F.

FIG. 2A shows a simplified drawing of an exemplary magnetic resonator structure. The magnetic resonator may include a loop of conductor acting as an inductive element 202 and a capacitive element 204 at the ends of the conductor loop. The inductor 202 and capacitor 204 of an electromagnetic resonator may be bulk circuit elements, or the inductance and capacitance may be distributed and may result from the way the conductors are formed, shaped, or positioned, in the structure.

For example, the inductor 202 may be realized by shaping a conductor to enclose a surface area, as shown in FIG. 2A. This type of resonator may be referred to as a capacitively-loaded loop inductor. Note that we may use the terms "loop" or "coil" to indicate generally a conducting structure (wire, tube, strip, etc.), enclosing a surface of any shape and dimension, with any number of turns. In FIG. 2A, the enclosed surface area is circular, but the surface may be any of a wide variety of other shapes and sizes and may be designed to achieve certain system performance specifications. In embodiments the inductance may be realized using inductor elements, distributed inductance, networks, arrays, series and parallel combinations of inductors and inductances, and the like. The inductance may be fixed or variable and may be used to vary impedance matching as well as resonant frequency operating conditions.

There are a variety of ways to realize the capacitance required to achieve the desired resonant frequency for a resonator structure. Capacitor plates 204 may be formed and utilized as shown in FIG. 2A, or the capacitance may be distributed and be realized between adjacent windings of a multi-loop conductor. The capacitance may be realized using capacitor elements, distributed capacitance, networks, arrays, series and parallel combinations of capacitances, and the like. The capacitance may be fixed or variable and may be used to vary impedance matching as well as resonant frequency operating conditions.

The inductive elements used in magnetic resonators may contain more than one loop and may spiral inward or outward or up or down or in some combination of directions. In general, the magnetic resonators may have a variety of shapes, sizes and number of turns and they may be composed of a variety of conducing materials. The conductor 210, for example, may be a wire, a Litz wire, a ribbon, a pipe, a trace formed from conducting ink, paint, gels, and the like or from single or multiple traces printed on a circuit board. An exemplary embodiment of a trace pattern on a substrate 208 forming inductive loops is depicted in FIG. 2B.

In embodiments the inductive elements may be formed using magnetic materials of any size, shape thickness, and the like, and of materials with a wide range of permeability and loss values. These magnetic materials may be solid blocks, they may enclose hollow volumes, they may be formed from many smaller pieces of magnetic material tiled and or stacked together, and they may be integrated with conducting sheets or enclosures made from highly conducting materials. Conductors may be wrapped around the magnetic materials to generate the magnetic field. These conductors may be wrapped around one or more than one axis of the structure. Multiple conductors may be wrapped around the magnetic materials and combined in parallel, or in series, or via a switch to form customized near-field patterns and/or to orient the dipole moment of the structure. Examples of resonators comprising magnetic material are depicted in FIGS. 2C, 2D, 2E. In FIG. 2D the resonator comprises loops of conductor 224 wrapped around a core of magnetic material 222 creating a structure that has a magnetic dipole moment 228 that is parallel to the axis of the loops of the conductor 224. The resonator may comprise multiple loops of conductor 216, 212 wrapped in orthogonal directions around the magnetic material 214 forming a resonator with a magnetic dipole moment 218, 220 that may be oriented in more than one direction as depicted in FIG. 2C, depending on how the conductors are driven.

An electromagnetic resonator may have a characteristic, natural, or resonant frequency determined by its physical properties. This resonant frequency is the frequency at which the energy stored by the resonator oscillates between that stored by the electric field, $W_E$, ($W_E = q^2/2C$, where q is the charge on the capacitor, C) and that stored by the magnetic field, $W_B$, ($W_B = Li^2/2$, where i is the current through the inductor, L) of the resonator. The frequency at which this energy is exchanged may be called the characteristic frequency, the natural frequency, or the resonant frequency of the resonator, and is given by ω, $$\omega = 2\pi f = \sqrt{\frac{1}{LC}}.$$

The resonant frequency of the resonator may be changed by tuning the inductance, L, and/or the capacitance, C, of the resonator. In one embodiment system parameters are dynamically adjustable or tunable to achieve as close as possible to optimal operating conditions. However, based on the discussion above, efficient enough energy exchange may be realized even if some system parameters are not variable or components are not capable of dynamic adjustment.

In embodiments a resonator may comprise an inductive element coupled to more than one capacitor arranged in a network of capacitors and circuit elements. In embodiments the coupled network of capacitors and circuit elements may be used to define more than one resonant frequency of the resonator. In embodiments a resonator may be resonant, or partially resonant, at more than one frequency.

In embodiments, a wireless power source may comprise of at least one resonator coil coupled to a power supply, which may be a switching amplifier, such as a class-D amplifier or a class-E amplifier or a combination thereof. In this case, the resonator coil is effectively a power load to the power supply. In embodiments, a wireless power device may comprise of at least one resonator coil coupled to a power load, which may be a switching rectifier, such as a class-D rectifier or a class-E rectifier or a combination thereof. In this case, the resonator coil is effectively a power supply for the power load, and the impedance of the load directly relates also to the work-drainage rate of the load from the resonator coil. The efficiency of power transmission between a power supply and a power load may be impacted by how closely matched the output impedance of the power source is to the input impedance of the load. Power may be delivered to the load at a maximum possible efficiency, when the input impedance of the load is equal to the complex conjugate of the internal impedance of the power supply. Designing the power supply or power load impedance to obtain a maximum power transmission efficiency is often called "impedance matching", and may also referred to as optimizing the ratio of useful-to-lost powers in the system. Impedance matching may be performed by adding networks or sets of elements such as capacitors, inductors, transformers, switches, resistors, and the like, to form impedance matching networks between a power supply and a power load. In embodiments, mechanical adjustments and changes in element positioning may be used to achieve impedance matching. For varying loads, the impedance matching network may include variable components that are dynamically adjusted to ensure that the impedance at the power supply terminals looking towards the load and the characteristic impedance of the power supply remain substantially complex conjugates of each other, even in dynamic environments and operating scenarios.

In embodiments, impedance matching may be accomplished by tuning the duty cycle, and/or the phase, and/or the frequency of the driving signal of the power supply or by tuning a physical component within the power supply, such as a capacitor. Such a tuning mechanism may be advantageous because it may allow impedance matching between a power supply and a load without the use of a tunable impedance matching network, or with a simplified tunable impedance matching network, such as one that has fewer tunable components for example. In embodiments, tuning the duty cycle, and/or frequency, and/or phase of the driving signal to a power supply may yield a dynamic impedance matching system with an extended tuning range or precision, with higher power, voltage and/or current capabilities, with faster electronic control, with fewer external components, and the like.

In some wireless energy transfer systems the parameters of the resonator such as the inductance may be affected by environmental conditions such as surrounding objects, temperature, orientation, number and position of other resonators and the like. Changes in operating parameters of the resonators may change certain system parameters, such as the efficiency of transferred power in the wireless energy transfer. For example, high-conductivity materials located near a resonator may shift the resonant frequency of a resonator and detune it from other resonant objects. In some embodiments, a resonator feedback mechanism is employed that corrects its frequency by changing a reactive element (e.g., an inductive element or capacitive element). In order to achieve acceptable matching conditions, at least some of the system parameters may need to be dynamically adjustable or tunable. All the system parameters may be dynamically adjustable or tunable to achieve approximately the optimal operating conditions. However, efficient enough energy exchange may be realized even if all or some system parameters are not variable. In some examples, at least some of the devices may not be dynamically adjusted. In some examples, at least some of the sources may not be dynamically adjusted. In some examples, at least some of the intermediate resonators may not be dynamically adjusted. In some examples, none of the system parameters may be dynamically adjusted.

In some embodiments changes in parameters of components may be mitigated by selecting components with characteristics that change in a complimentary or opposite way or direction when subjected to differences in operating environment or operating point. In embodiments, a system may be designed with components, such as capacitors, that have an opposite dependence or parameter fluctuation due to temperature, power levels, frequency, and the like. In some embodiments, the component values as a function of temperature may be stored in a look-up table in a system microcontroller and the reading from a temperature sensor may be used in the system control feedback loop to adjust other parameters to compensate for the temperature induced component value changes.

In some embodiments the changes in parameter values of components may be compensated with active tuning circuits comprising tunable components. Circuits that monitor the operating environment and operating point of components and system may be integrated in the design. The monitoring circuits may provide the signals necessary to actively compensate for changes in parameters of components. For example, a temperature reading may be used to calculate expected changes in, or to indicate previously measured values of, capacitance of the system allowing compensation by switching in other capacitors or tuning capacitors to maintain the desired capacitance over a range of temperatures. In embodiments, the RF amplifier switching waveforms may be adjusted to compensate for component value or load changes in the system. In some embodiments the changes in parameters of components may be compensated with active cooling, heating, active environment conditioning, and the like.

The parameter measurement circuitry may measure or monitor certain power, voltage, and current, signals in the system, and processors or control circuits may adjust certain settings or operating parameters based on those measurements. In addition the magnitude and phase of voltage and current signals, and the magnitude of the power signals, throughout the system may be accessed to measure or monitor the system performance. The measured signals referred to throughout this disclosure may be any combination of port parameter signals, as well as voltage signals, current signals, power signals, temperatures signals and the like. These parameters may be measured using analog or digital techniques, they may be sampled and processed, and they may be digitized or converted using a number of known analog and digital processing techniques. In embodiments, preset values of certain measured quantities are loaded in a system controller or memory location and used in various feedback and control loops. In embodiments, any combination of measured, monitored, and/or preset signals may be used in feedback circuits or systems to control the operation of the resonators and/or the system.

Adjustment algorithms may be used to adjust the frequency, Q, and/or impedance of the magnetic resonators. The algorithms may take as inputs reference signals related to the degree of deviation from a desired operating point for the system and may output correction or control signals related to that deviation that control variable or tunable elements of the system to bring the system back towards the desired operating point or points. The reference signals for the magnetic resonators may be acquired while the resonators are exchanging power in a wireless power transmission system, or they may be switched out of the circuit during system operation. Corrections to the system may be applied or performed continuously, periodically, upon a threshold crossing, digitally, using analog methods, and the like.

In embodiments, lossy extraneous materials and objects may introduce potential reductions in efficiencies by absorbing the magnetic and/or electric energy of the resonators of the wireless power transmission system. Those impacts may be mitigated in various embodiments by positioning resonators to minimize the effects of the lossy extraneous materials and objects and by placing structural field shaping elements (e.g., conductive structures, plates and sheets, magnetic material structures, plates and sheets, and combinations thereof) to minimize their effect.

One way to reduce the impact of lossy materials on a resonator is to use high-conductivity materials, magnetic materials, or combinations thereof to shape the resonator fields such that they avoid the lossy objects. In an exemplary embodiment, a layered structure of high-conductivity material and magnetic material may tailor, shape, direct, reorient, etc. the resonator's electromagnetic fields so that they avoid lossy objects in their vicinity by deflecting the fields. FIG. 2D shows a top view of a resonator with a sheet of conductor 226 below the magnetic material that may used to tailor the fields of the resonator so that they avoid lossy objects that may be below the sheet of conductor 226. The layer or sheet of good 226 conductor may comprise any high conductivity materials such as copper, silver, aluminum, as may be most appropriate for a given application. In certain embodiments, the layer or sheet of good conductor is thicker than the skin depth of the conductor at the resonator operating frequency. The conductor sheet may be preferably larger than the size of the resonator, extending beyond the physical extent of the resonator.

In environments and systems where the amount of power being transmitted could present a safety hazard to a person or animal that may intrude into the active field volume, safety measures may be included in the system. In embodiments where power levels require particularized safety measures, the packaging, structure, materials, and the like of the resonators may be designed to provide a spacing or "keep away" zone from the conducting loops in the magnetic resonator. To provide further protection, high-Q resonators and power and control circuitry may be located in enclosures that confine high voltages or currents to within the enclosure, that protect the resonators and electrical components from weather, moisture, sand, dust, and other external elements, as well as from impacts, vibrations, scrapes, explosions, and other types of mechanical shock. Such enclosures call for attention to various factors such as thermal dissipation to maintain an acceptable operating temperature range for the electrical components and the resonator. In embodiments, enclosure may be constructed of non-lossy materials such as composites, plastics, wood, concrete, and the like and may be used to provide a minimum distance from lossy objects to the resonator components. A minimum separation distance from lossy objects or environments which may include metal objects, salt water, oil and the like, may improve the efficiency of wireless energy transfer. In embodiments, a "keep away" zone may be used to increase the perturbed Q of a resonator or system of resonators. In embodiments a minimum separation distance may provide for a more reliable or more constant operating parameters of the resonators.

In embodiments, resonators and their respective sensor and control circuitry may have various levels of integration with other electronic and control systems and subsystems. In some embodiments the power and control circuitry and the device resonators are completely separate modules or enclosures with minimal integration to existing systems, providing a power output and a control and diagnostics interface. In some embodiments a device is configured to house a resonator and circuit assembly in a cavity inside the enclosure, or integrated into the housing or enclosure of the device.

Example Resonator Circuitry

Figure 3:
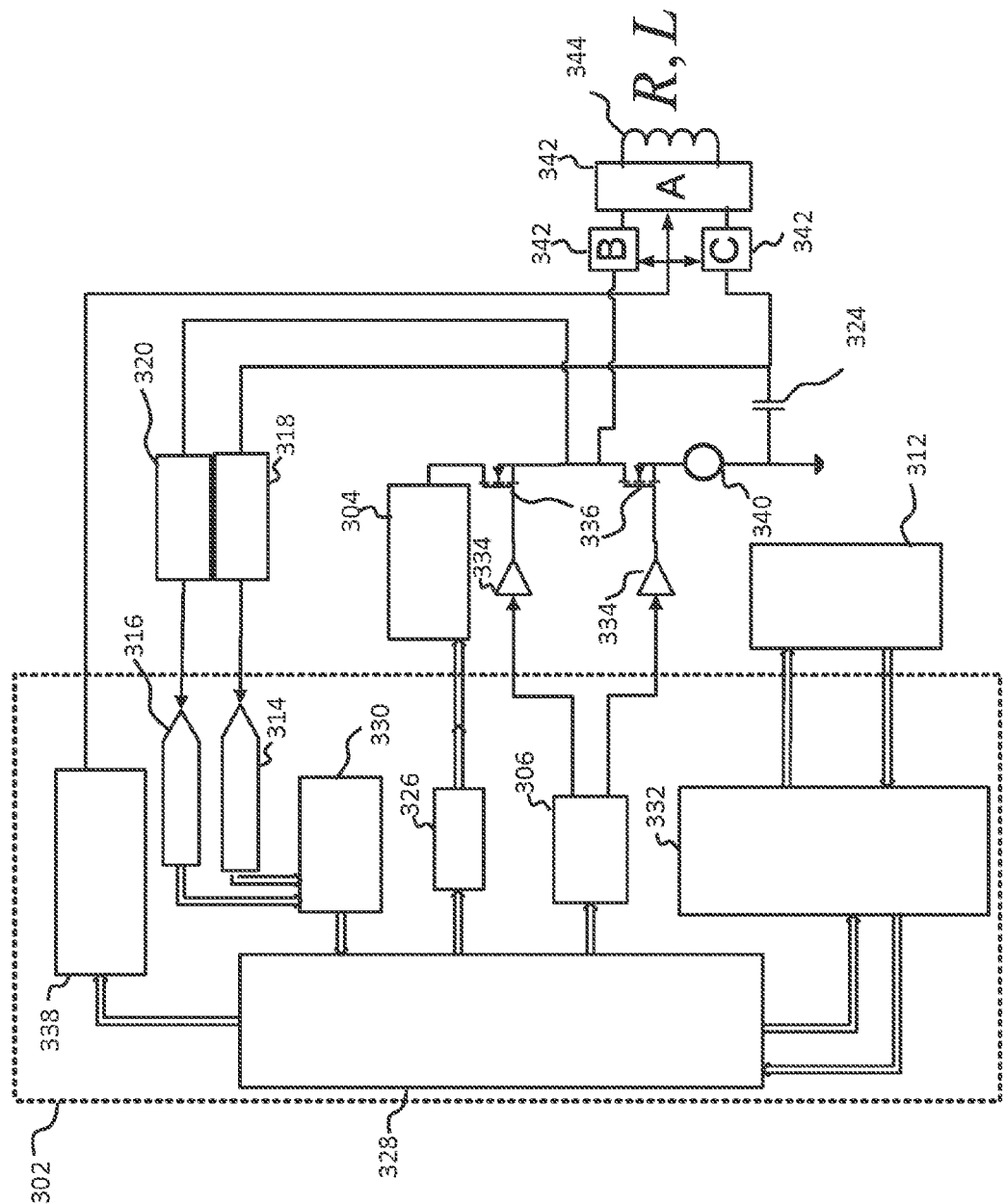
FIG. 3 is a block diagram of a wireless source with a single-ended amplifier.

FIGS. 3 and 4 show high level block diagrams depicting power generation, monitoring, and control components for exemplary sources of a wireless energy transfer system. FIG. 3 is a block diagram of a source comprising a half-bridge switching power amplifier and some of the associated measurement, tuning, and control circuitry. FIG. 4 is a block diagram of a source comprising a full-bridge switching amplifier and some of the associated measurement, tuning, and control circuitry.

The half bridge system topology depicted in FIG. 3 may comprise a processing unit that executes a control algorithm 328. The processing unit executing a control algorithm 328 may be a microcontroller, an application specific circuit, a field programmable gate array, a processor, a digital signal processor, and the like. The processing unit may be a single device or it may be a network of devices. The control algorithm may run on any portion of the processing unit. The algorithm may be customized for certain applications and may comprise a combination of analog and digital circuits and signals. The master algorithm may measure and adjust voltage signals and levels, current signals and levels, signal phases, digital count settings, and the like.

The system may comprise an optional source/device and/or source/other resonator communication controller 332 coupled to wireless communication circuitry 312. The optional source/device and/or source/other resonator communication controller 332 may be part of the same processing unit that executes the master control algorithm, it may a part or a circuit within a microcontroller 302, it may be external to the wireless power transmission modules, it may be substantially similar to communication controllers used in wire powered or battery powered applications but adapted to include some new or different functionality to enhance or support wireless power transmission.

The system may comprise a PWM generator 306 coupled to at least two transistor gate drivers 334 and may be controlled by the control algorithm. The two transistor gate drivers 334 may be coupled directly or via gate drive transformers to two power transistors 336 that drive the source resonator coil 344 through impedance matching network components 342. The power transistors 336 may be coupled and powered with an adjustable DC supply 304 and the adjustable DC supply 304 may be controlled by a variable bus voltage, Vbus. The Vbus controller may be controlled by the control algorithm 328 and may be part of, or integrated into, a microcontroller 302 or other integrated circuits. The Vbus controller 326 may control the voltage output of an adjustable DC supply 304 which may be used to control power output of the amplifier and power delivered to the resonator coil 344.

The system may comprise sensing and measurement circuitry including signal filtering and buffering circuits 318, 320 that may shape, modify, filter, process, buffer, and the like, signals prior to their input to processors and/or converters such as analog to digital converters (ADC) 314, 316, for example. The processors and converters such as ADCs 314, 316 may be integrated into a microcontroller 302 or may be separate circuits that may be coupled to a processing core 330. Based on measured signals, the control algorithm 328 may generate, limit, initiate, extinguish, control, adjust, or modify the operation of any of the PWM generator 306, the communication controller 332, the Vbus control 326, the source impedance matching controller 338, the filter/buffering elements, 318, 320, the converters, 314, 316, the resonator coil 344, and may be part of, or integrated into, a microcontroller 302 or a separate circuit. The impedance matching networks 342 and resonator coils 344 may include electrically controllable, variable, or tunable components such as capacitors, switches, inductors, and the like, as described herein, and these components may have their component values or operating points adjusted according to signals received from the source impedance matching controller 338. Components may be tuned to adjust the operation and characteristics of the resonator including the power delivered to and by the resonator, the resonant frequency of the resonator, the impedance of the resonator, the Q of the resonator, and any other coupled systems, and the like. The resonator may be any type or structure resonator described herein including a capacitively loaded loop resonator, a planer resonator comprising a magnetic material or any combination thereof.

The full bridge system topology depicted in FIG. 4 may comprise a processing unit that executes a master control algorithm 328. The processing unit executing the control algorithm 328 may be a microcontroller, an application specific circuit, a field programmable gate array, a processor, a digital signal processor, and the like. The system may comprise a source/device and/or source/other resonator communication controller 332 coupled to wireless communication circuitry 312. The source/device and/or source/other resonator communication controller 332 may be part of the same processing unit that executes that master control algorithm, it may a part or a circuit within a microcontroller 302, it may be external to the wireless power transmission modules, it may be substantially similar to communication controllers used in wire powered or battery powered applications but adapted to include some new or different functionality to enhance or support wireless power transmission.

The system may comprise a PWM generator 410 with at least two outputs coupled to at least four transistor gate drivers 334 that may be controlled by signals generated in a master control algorithm. The four transistor gate drivers 334 may be coupled to four power transistors 336 directly or via gate drive transformers that may drive the source resonator coil 344 through impedance matching networks 342. The power transistors 336 may be coupled and powered with an adjustable DC supply 304 and the adjustable DC supply 304 may be controlled by a Vbus controller 326 which may be controlled by a master control algorithm. The Vbus controller 326 may control the voltage output of the adjustable DC supply 304 which may be used to control power output of the amplifier and power delivered to the resonator coil 344.

The system may comprise sensing and measurement circuitry including signal filtering and buffering circuits 318, 320 and differential/single ended conversion circuitry 402, 404 that may shape, modify, filter, process, buffer, and the like, signals prior to being input to processors and/or converters such as analog to digital converters (ADC) 314, 316. The processors and/or converters such as ADC 314, 316 may be integrated into a microcontroller 302 or may be separate circuits that may be coupled to a processing core 330. Based on measured signals, the master control algorithm may generate, limit, initiate, extinguish, control, adjust, or modify the operation of any of the PWM generator 410, the communication controller 332, the Vbus controller 326, the source impedance matching controller 338, the filter/buffering elements, 318, 320, differential/single ended conversion circuitry 402, 404, the converters, 314, 316, the resonator coil 344, and may be part of or integrated into a microcontroller 302 or a separate circuit.

Impedance matching networks 342 and resonator coils 344 may comprise electrically controllable, variable, or tunable components such as capacitors, switches, inductors, and the like, as described herein, and these components may have their component values or operating points adjusted according to signals received from the source impedance matching controller 338. Components may be tuned to enable tuning of the operation and characteristics of the resonator including the power delivered to and by the resonator, the resonant frequency of the resonator, the impedance of the resonator, the Q of the resonator, and any other coupled systems, and the like. The resonator may be any type or structure resonator described herein including a capacitively loaded loop resonator, a planar resonator comprising a magnetic material or any combination thereof.

Impedance matching networks may comprise fixed value components such as capacitors, inductors, and networks of components as described herein. Parts of the impedance matching networks, A, B and C, may comprise inductors, capacitors, transformers, and series and parallel combinations of such components, as described herein. In some embodiments, parts of the impedance matching networks A, B, and C, may be empty (short-circuited). In some embodiments, part B comprises a series combination of an inductor and a capacitor, and part C is empty.

The full bridge topology may allow operation at higher output power levels using the same DC bus voltage as an equivalent half bridge amplifier. The half bridge exemplary topology of FIG. 3 may provide a single-ended drive signal, while the exemplary full bridge topology of FIG. 4 may provide a differential drive to the source resonator 308. The impedance matching topologies and components and the resonator structure may be different for the two systems, as discussed herein.

The exemplary systems depicted in FIGS. 3 and 4 may further include fault detection circuitry 340 that may be used to trigger the shutdown of the microcontroller in the source amplifier or to change or interrupt the operation of the amplifier. This protection circuitry may comprise a high speed comparator or comparators to monitor the amplifier return current, the amplifier bus voltage (Vbus) from the DC supply 304, the voltage across the source resonator 308 and/or the optional tuning board, or any other voltage or current signals that may cause damage to components in the system or may yield undesirable operating conditions. Preferred embodiments may depend on the potentially undesirable operating modes associated with different applications. In some embodiments, protection circuitry may not be implemented or circuits may not be populated. In some embodiments, system and component protection may be implemented as part of a master control algorithm and other system monitoring and control circuits. In embodiments, dedicated fault circuitry 340 may include an output (not shown) coupled to a master control algorithm 328 that may trigger a system shutdown, a reduction of the output power (e.g. reduction of Vbus), a change to the PWM generator, a change in the operating frequency, a change to a tuning element, or any other reasonable action that may be implemented by the control algorithm 328 to adjust the operating point mode, improve system performance, and/or provide protection.

As described herein, sources in wireless power transfer systems may use a measurement of the input impedance of the impedance matching network 342 driving source resonator coil 344 as an error or control signal for a system control loop that may be part of the master control algorithm. In exemplary embodiments, variations in any combination of three parameters may be used to tune the wireless power source to compensate for changes in environmental conditions, for changes in coupling, for changes in device power demand, for changes in module, circuit, component or subsystem performance, for an increase or decrease in the number or sources, devices, or repeaters in the system, for user initiated changes, and the like. In exemplary embodiments, changes to the amplifier duty cycle, to the component values of the variable electrical components such as variable capacitors and inductors, and to the DC bus voltage may be used to change the operating point or operating range of the wireless source and improve some system operating value. The specifics of the control algorithms employed for different applications may vary depending on the desired system performance and behavior.

Impedance measurement circuitry such as described herein, and shown in FIGS. 3 and 4, may be implemented using two-channel simultaneous sampling ADCs and these ADCs may be integrated into a microcontroller chip or may be part of a separate circuit. Simultaneously sampling of the voltage and current signals at the input to a source resonator's impedance matching network and/or the source resonator, may yield the phase and magnitude information of the current and voltage signals and may be processed using known signal processing techniques to yield complex impedance parameters. In some embodiments, monitoring only the voltage signals or only the current signals may be sufficient.

The impedance measurements described herein may use direct sampling methods which may be relatively simpler than some other known sampling methods. In embodiments, measured voltage and current signals may be conditioned, filtered and scaled by filtering/buffering circuitry before being input to ADCs. In embodiments, the filter/buffering circuitry may be adjustable to work at a variety of signal levels and frequencies, and circuit parameters such as filter shapes and widths may be adjusted manually, electronically, automatically, in response to a control signal, by the master control algorithm, and the like. Exemplary embodiments of filter/buffering circuits are shown in FIGS. 3, 4, and 5.

Figure 5A:
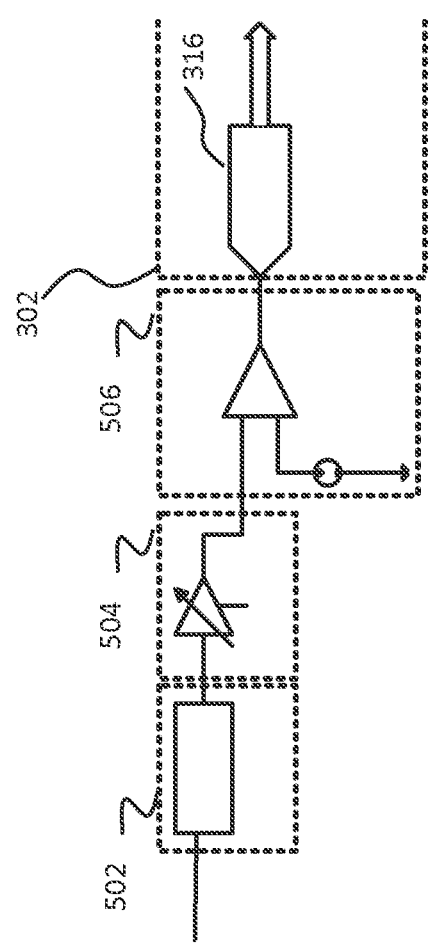
FIGS. 5A and 5B are block diagrams of sensing circuits.
Figure 5B:
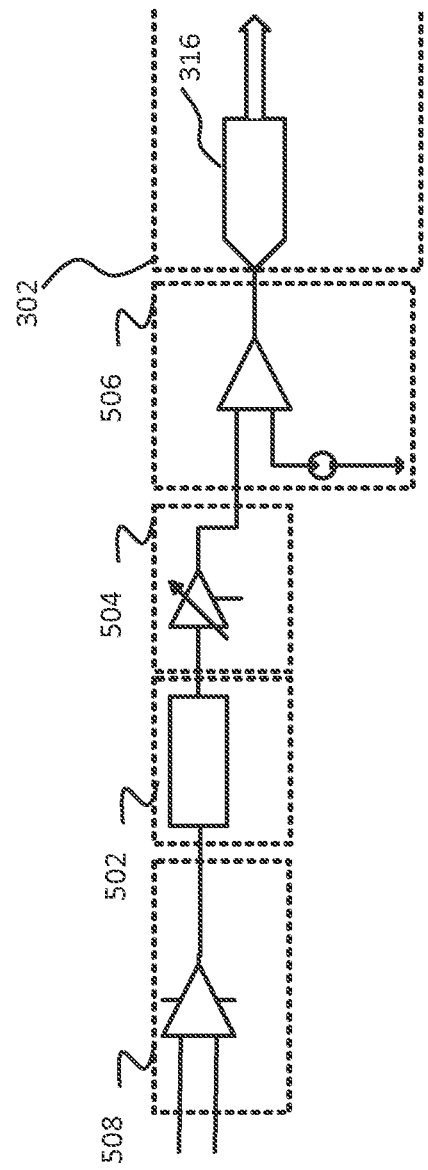

FIG. 5 shows more detailed views of exemplary circuit components that may be used in filter/buffering circuitry. In embodiments, and depending on the types of ADCs used in the system designs, single-ended amplifier topologies may reduce the complexity of the analog signal measurement paths used to characterize system, subsystem, module and/or component performance by eliminating the need for hardware to convert from differential to single-ended signal formats. In other implementations, differential signal formats may be preferable. The implementations shown in FIG. 5 are exemplary, and should not be construed to be the only possible way to implement the functionality described herein. Rather it should be understood that the analog signal path may employ components with different input requirements and hence may have different signal path architectures.

In both the single ended and differential amplifier topologies, the input current to the impedance matching networks 342 driving the resonator coils 344 may be obtained by measuring the voltage across a capacitor 324, or via a current sensor of some type. For the exemplary single-ended amplifier topology in FIG. 3, the current may be sensed on the ground return path from the impedance matching network 342. For the exemplary differential power amplifier depicted in FIG. 4, the input current to the impedance matching networks 342 driving the resonator coils 344 may be measured using a differential amplifier across the terminals of a capacitor 324 or via a current sensor of some type. In the differential topology of FIG. 4, the capacitor 324 may be duplicated at the negative output terminal of the source power amplifier.

In both topologies, after single ended signals representing the input voltage and current to the source resonator and impedance matching network are obtained, the signals may be filtered 502 to obtain the desired portions of the signal waveforms. In embodiments, the signals may be filtered to obtain the fundamental component of the signals. In embodiments, the type of filtering performed, such as low pass, bandpass, notch, and the like, as well as the filter topology used, such as elliptical, Chebyshev, Butterworth, and the like, may depend on the specific requirements of the system. In some embodiments, no filtering will be required.

The voltage and current signals may be amplified by an optional amplifier 504. The gain of the optional amplifier 504 may be fixed or variable. The gain of the amplifier may be controlled manually, electronically, automatically, in response to a control signal, and the like. The gain of the amplifier may be adjusted in a feedback loop, in response to a control algorithm, by the master control algorithm, and the like. In embodiments, required performance specifications for the amplifier may depend on signal strength and desired measurement accuracy, and may be different for different application scenarios and control algorithms.

The measured analog signals may have a DC offset added to them, 506, which may be required to bring the signals into the input voltage range of the ADC which for some systems may be 0 to 3.3V. In some systems this stage may not be required, depending on the specifications of the particular ADC used.

Figure 6A:
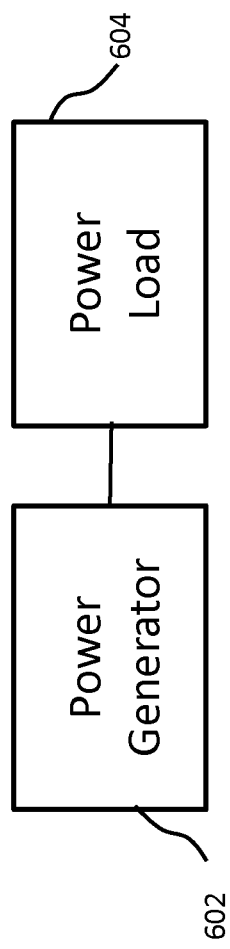
FIGS. 6A, 6B, and 6C are block diagrams of a wireless source.
Figure 6B:
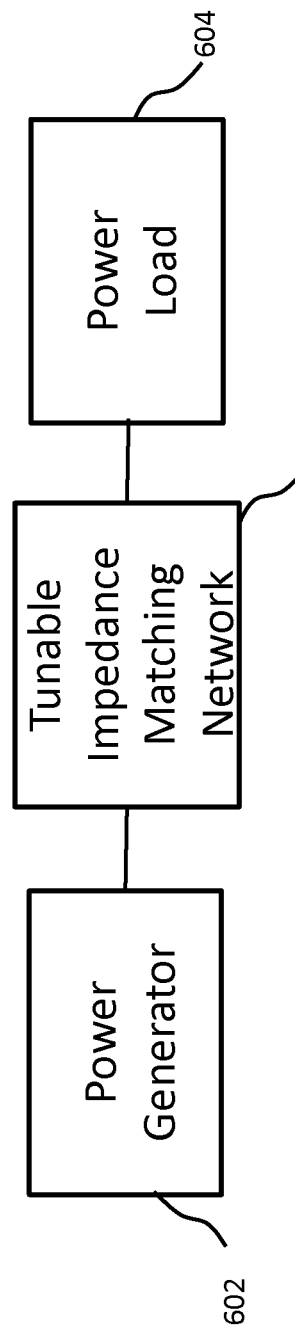
Figure 6C:
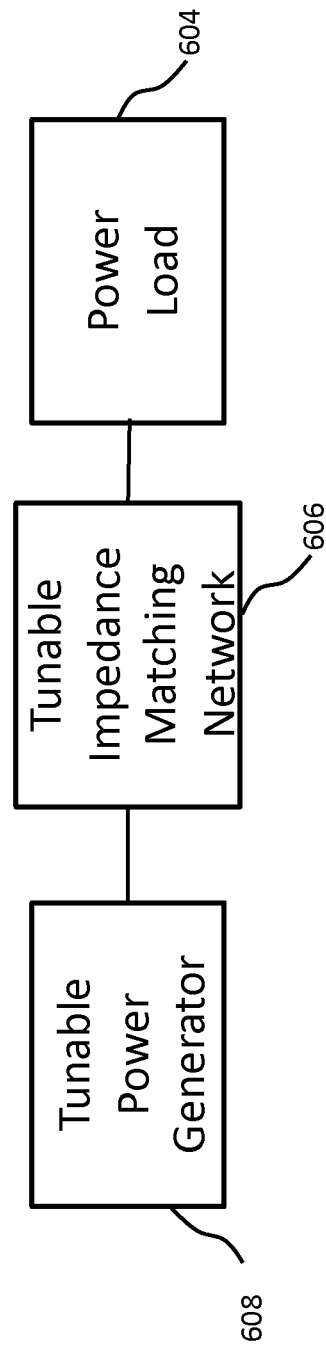

As described above, the efficiency of power transmission between a power generator and a power load may be impacted by how closely matched the output impedance of the generator is to the input impedance of the load. In an exemplary system as shown in FIG. 6A, power may be delivered to the load at a maximum possible efficiency, when the input impedance of the load 604 is equal to the complex conjugate of the internal impedance of the power generator or the power amplifier 602. Designing the generator or load impedance to obtain a high and/or maximum power transmission efficiency may be called "impedance matching". Impedance matching may be performed by inserting appropriate networks or sets of elements such as capacitors, resistors, inductors, transformers, switches and the like, to form an impedance matching network 606, between a power generator 602 and a power load 604 as shown in FIG. 6B. In other embodiments, mechanical adjustments and changes in element positioning may be used to achieve impedance matching. As described above for varying loads, the impedance matching network 606 may include variable components that are dynamically adjusted to ensure that the impedance at the generator terminals looking towards the load and the characteristic impedance of the generator remain substantially complex conjugates of each other, even in dynamic environments and operating scenarios. In embodiments, dynamic impedance matching may be accomplished by tuning the duty cycle, and/or the phase, and/or the frequency of the driving signal of the power generator or by tuning a physical component within the power generator, such as a capacitor, as depicted in FIG. 6C. Such a tuning mechanism may be advantageous because it may allow impedance matching between a power generator 608 and a load without the use of a tunable impedance matching network, or with a simplified tunable impedance matching network 606, such as one that has fewer tunable components for example. In embodiments, tuning the duty cycle, and/or frequency, and/or phase of the driving signal to a power generator may yield a dynamic impedance matching system with an extended tuning range or precision, with higher power, voltage and/or current capabilities, with faster electronic control, with fewer external components, and the like. The impedance matching methods, architectures, algorithms, protocols, circuits, measurements, controls, and the like, described below, may be useful in systems where power generators drive high-Q magnetic resonators and in high-Q wireless power transmission systems as described herein. In wireless power transfer systems a power generator may be a power amplifier driving a resonator, sometimes referred to as a source resonator, which may be a load to the power amplifier. In wireless power applications, it may be preferable to control the impedance matching between a power amplifier and a resonator load to control the efficiency of the power delivery from the power amplifier to the resonator. The impedance matching may be accomplished, or accomplished in part, by tuning or adjusting the duty cycle, and/or the phase, and/or the frequency of the driving signal of the power amplifier that drives the resonator.

Efficiency of Switching Amplifiers

Switching amplifiers, such as class D, E, F amplifiers, and the like or any combinations thereof, deliver power to a load at a maximum efficiency when no power is dissipated on the switching elements of the amplifier. This operating condition may be accomplished by designing the system so that the switching operations which are most critical (namely those that are most likely to lead to switching losses) are done when both the voltage across the switching element and the current through the switching element are zero. These conditions may be referred to as Zero Voltage Switching (ZVS) and Zero Current Switching (ZCS) conditions respectively. When an amplifier operates at ZVS and ZCS either the voltage across the switching element or the current through the switching element is zero and thus no power can be dissipated in the switch. Since a switching amplifier may convert DC (or very low frequency AC) power to AC power at a specific frequency or range of frequencies, a filter may be introduced before the load to prevent unwanted harmonics that may be generated by the switching process from reaching the load and being dissipated there. In embodiments, a switching amplifier may be designed to operate at maximum efficiency of power conversion, when connected to a resonant load, with a nontrivial quality factor (say Q>5), and of a specific impedance $Z_o^* = R_o + jX_o$, which leads to simultaneous ZVS and ZCS. We define $Z_o = R_o - jX_o$ as the characteristic impedance of the amplifier, so that achieving maximum power transmission efficiency is equivalent to impedance matching the resonant load to the characteristic impedance of the amplifier.

In a switching amplifier, the switching frequency of the switching elements, $f_{switch}$, wherein $f_{switch} = \omega/2\pi$ and the duty cycle, dc, of the ON switch-state duration of the switching elements may be the same for all switching elements of the amplifier. In this specification, we will use the term "class D" to denote both class D and class DE amplifiers, that is, switching amplifiers with dc<=50%.

Figure 7:
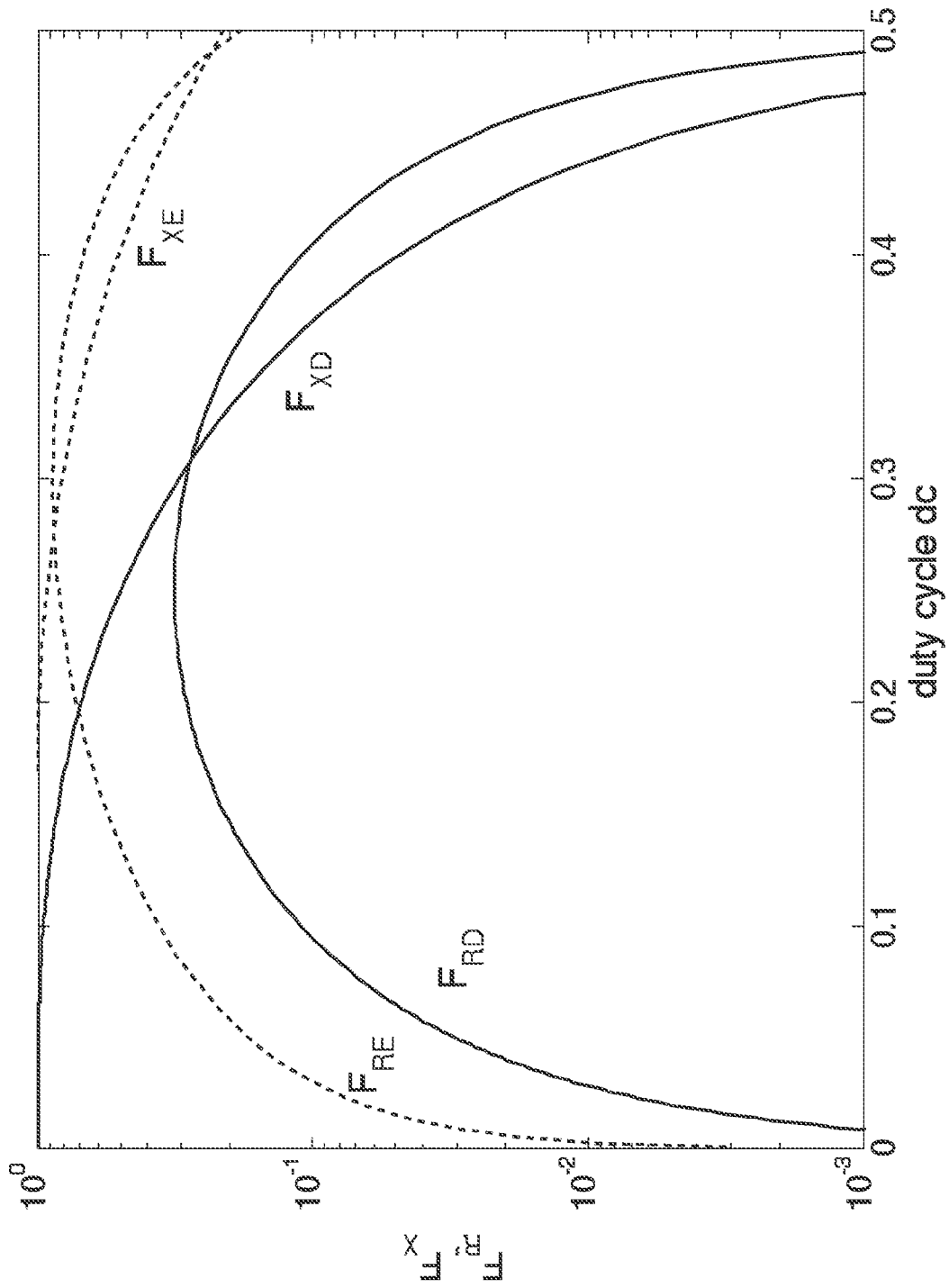
FIG. 7 is a plot showing the effects of a duty cycle on the parameters of an amplifier.

The value of the characteristic impedance of the amplifier may depend on the operating frequency, the amplifier topology, and the switching sequence of the switching elements. In some embodiments, the switching amplifier may be a half-bridge topology and, in some embodiments, a full-bridge topology. In some embodiments, the switching amplifier may be class D and, in some embodiments, class E. In any of the above embodiments, assuming the elements of the bridge are symmetric, the characteristic impedance of the switching amplifier has the form $$R_o = F_R(dc)/\omega C_a, X_o = F_X(dc)/\omega C_a, \quad (1)$$

where dc is the duty cycle of ON switch-state of the switching elements, the functions $F_R(dc)$ and $F_X(dc)$ are plotted in FIG. 7 (both for class D and E), $\omega$ is the frequency at which the switching elements are switched, and $C_a = n_a C_{switc}$ where $C_{switc}$ is the capacitance across each switch, including both the transistor output capacitance and also possible external capacitors placed in parallel with the switch, while $n_a = 1$ for a full bridge and $n_a = 2$ for a half bridge. For class D, one can also write the analytical expressions $$F_R(dc) = \sin^2 u/\pi, F_X(dc) = (u - \sin u * \cos u)/\pi, \quad (2)$$

where $u = \pi(1 - 2*dc)$, indicating that the characteristic impedance level of a class D amplifier decreases as the duty cycle, dc, increases towards 50%. For a class D amplifier operation with dc=50%, achieving ZVS and ZCS is possible only when the switching elements have practically no output capacitance ($C_a = 0$) and the load is exactly on resonance ($X_o = 0$), while $R_o$ can be arbitrary.

Impedance Matching Networks

In applications, the driven load may have impedance that is very different from the characteristic impedance of the external driving circuit, to which it is connected. Furthermore, the driven load may not be a resonant network. An Impedance Matching Network (IMN) is a circuit network that may be connected before a load as in FIG. 6B, in order to regulate the impedance that is seen at the input of the network consisting of the IMN circuit and the load. An IMN circuit may typically achieve this regulation by creating a resonance close to the driving frequency. Since such an IMN circuit accomplishes all conditions needed to maximize the power transmission efficiency from the generator to the load (resonance and impedance matching—ZVS and ZCS for a switching amplifier), in embodiments, an IMN circuit may be used between the driving circuit and the load.

For an arrangement shown in FIG. 6B, let the input impedance of the network consisting of the Impedance Matching Network (IMN) circuit and the load (denoted together from now on as IMN+load) be $Z_l = R_l(\omega) + jX_l(\omega)$. The impedance matching conditions of this network to the external circuit with characteristic impedance $Z_o = R_o - jX_o$ are then $R_l(\omega) = R_o$, $X_l(\omega) = X_o$.

Methods for Tunable Impedance Matching of a Variable Load

In embodiments where the load may be variable, impedance matching between the load and the external driving circuit, such as a linear or switching power amplifier, may be achieved by using adjustable/tunable components in the IMN circuit that may be adjusted to match the varying load to the fixed characteristic impedance $Z_o$ of the external circuit (FIG. 6B). To match both the real and imaginary parts of the impedance two tunable/variable elements in the IMN circuit may be needed.

In embodiments, the load may be inductive (such as a resonator coil) with impedance $R+j\omega L$, so the two tunable elements in the IMN circuit may be two tunable capacitance networks or one tunable capacitance network and one tunable inductance network or one tunable capacitance network and one tunable mutual inductance network.

In embodiments where the load may be variable, the impedance matching between the load and the driving circuit, such as a linear or switching power amplifier, may be achieved by using adjustable/tunable components or parameters in the amplifier circuit that may be adjusted to match the characteristic impedance $Z_o$ of the amplifier to the varying (due to load variations) input impedance of the network consisting of the IMN circuit and the load (IMN+load), where the IMN circuit may also be tunable (FIG. 6C). To match both the real and imaginary parts of the impedance, a total of two tunable/variable elements or parameters in the amplifier and the IMN circuit may be needed. The disclosed impedance matching method can reduce the required number of tunable/variable elements in the IMN circuit or even completely eliminate the requirement for tunable/variable elements in the IMN circuit. In some examples, one tunable element in the power amplifier and one tunable element in the IMN circuit may be used. In some examples, two tunable elements in the power amplifier and no tunable element in the IMN circuit may be used.

In embodiments, the tunable elements or parameters in the power amplifier may be the frequency, amplitude, phase, waveform, duty cycle and the like of the drive signals applied to transistors, switches, diodes and the like.

In embodiments, the power amplifier with tunable characteristic impedance may be a tunable switching amplifier of class D, E, F or any combinations thereof. Combining Equations (1) and (2), the impedance matching conditions for this network are $$R_l(\omega)=F_R(\text{dc})/\omega C_a, X_l(\omega)=F_X(\text{dc})/\omega C_a \quad (3).$$

In some examples of a tunable switching amplifier, one tunable element may be the capacitance $C_a$, which may be tuned by tuning the external capacitors placed in parallel with the switching elements.

In some examples of a tunable switching amplifier, one tunable element may be the duty cycle dc of the ON switch-state of the switching elements of the amplifier. Adjusting the duty cycle, dc, via Pulse Width Modulation (PWM) has been used in switching amplifiers to achieve output power control. In this specification, we disclose that PWM may also be used to achieve impedance matching, namely to satisfy Eqs. (3), and thus maximize the amplifier efficiency.

In some examples of a tunable switching amplifier one tunable element may be the switching frequency, which is also the driving frequency of the IMN+load network and may be designed to be substantially close to the resonant frequency of the IMN+load network. Tuning the switching frequency may change the characteristic impedance of the amplifier and the impedance of the IMN+load network. The switching frequency of the amplifier may be tuned appropriately together with one more tunable parameters, so that Eqs. (3) are satisfied.

Figure 8:
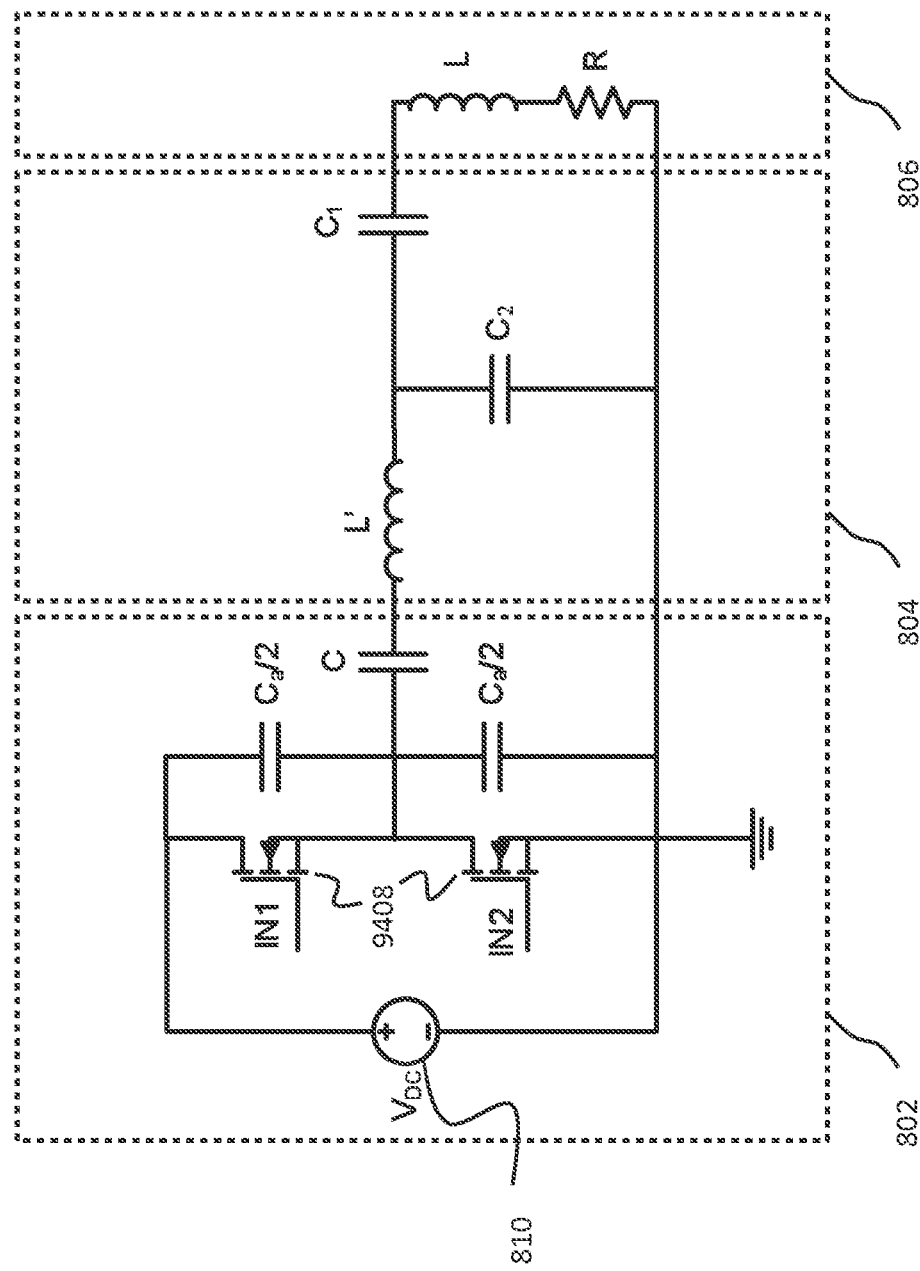
FIG. 8 is a simplified circuit diagram of a wireless power source with a switching amplifier.

A benefit of tuning the duty cycle and/or the driving frequency of the amplifier for dynamic impedance matching is that these parameters can be tuned electronically, quickly, and over a broad range. In contrast, for example, a tunable capacitor that can sustain a large voltage and has a large enough tunable range and quality factor may be expensive, slow or unavailable for with the necessary component specifications Examples of Methods for Tunable Impedance Matching of a Variable Load A simplified circuit diagram showing the circuit level structure of a class D power amplifier 802, impedance matching network 804 and an inductive load 806 is shown in FIG. 8. The diagram shows the basic components of the system with the switching amplifier 804 comprising a power source 810, switching elements 808, and capacitors. The impedance matching network 804 comprising inductors and capacitors, and the load 806 modeled as an inductor and a resistor.

An exemplary embodiment of this inventive tuning scheme comprises a half-bridge class-D amplifier operating at switching frequency f and driving a low-loss inductive element $R+j\omega L$ via an IMN, as shown in FIG. 8.

In some embodiments L' may be tunable. L' may be tuned by a variable tapping point on the inductor or by connecting a tunable capacitor in series or in parallel to the inductor. In some embodiments $C_a$ may be tunable. For the half bridge topology, $C_a$ may be tuned by varying either one or both capacitors $C_{switc}$, as only the parallel sum of these capacitors matters for the amplifier operation. For the full bridge topology, $C_a$ may be tuned by varying either one, two, three or all capacitors $C_{switc}$, as only their combination (series sum of the two parallel sums associated with the two halves of the bridge) matters for the amplifier operation.

Figure 9:
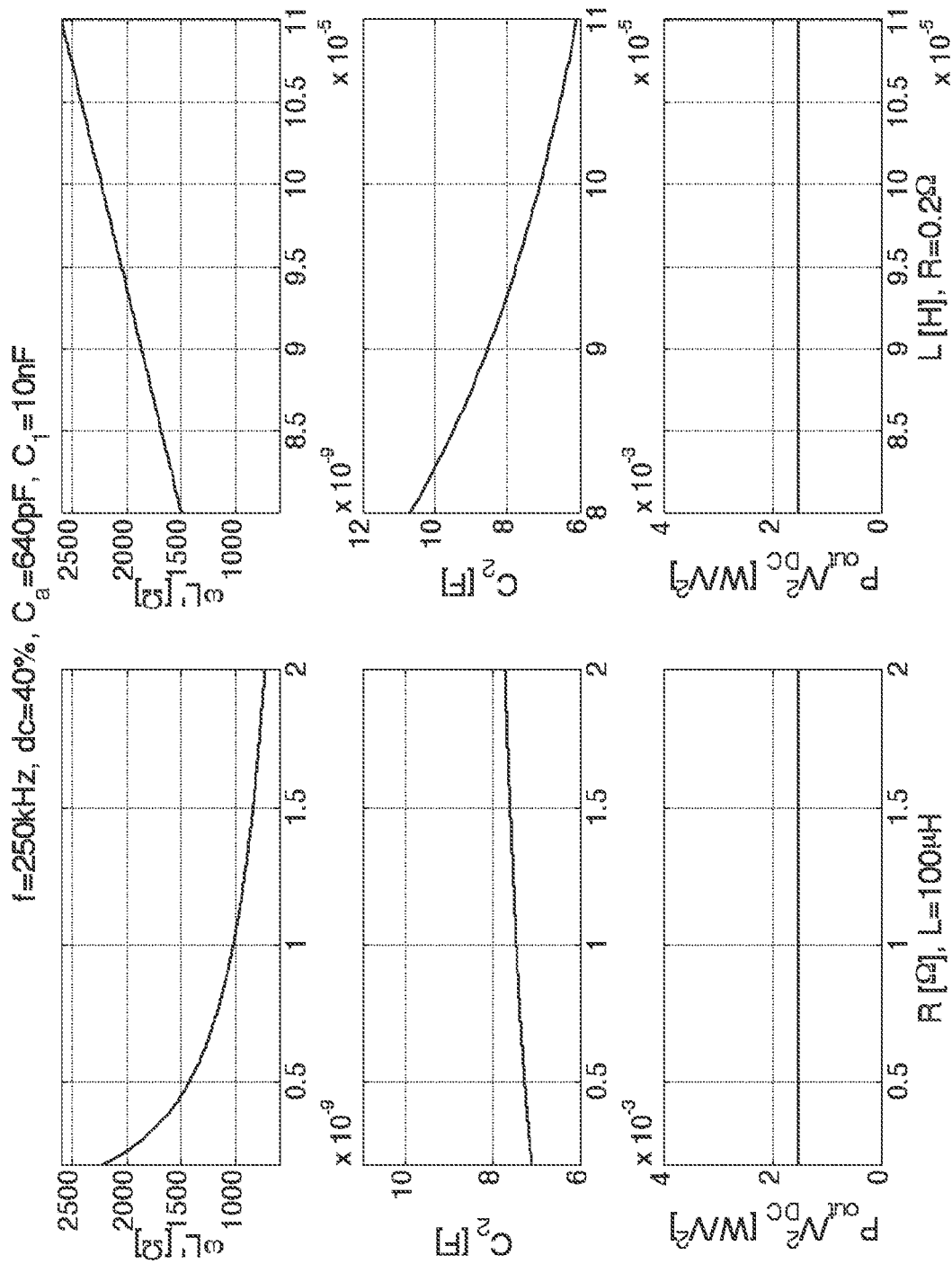
FIG. 9 shows plots of the effects of changes of parameters of a wireless power source.

In some embodiments of tunable impedance matching, two of the components of the IMN may be tunable. In some embodiments, L' and $C_2$ may be tuned. Then, FIG. 9 shows the values of the two tunable components needed to achieve impedance matching as functions of the varying R and L of the inductive element, and the associated variation of the output power (at given DC bus voltage) of the amplifier, for f=250 kHz, dc=40%, $C_a$=640 pF and $C_1$=10 nF. Since the IMN always adjusts to the fixed characteristic impedance of the amplifier, the output power is always constant as the inductive element is varying.

In some embodiments of tunable impedance matching, elements in the switching amplifier may also be tunable. In some embodiments the capacitance $C_a$ along with the IMN capacitor $C_2$ may be tuned. Then, FIG. 10 shows the values of the two tunable components needed to achieve impedance matching as functions of the varying R and L of the inductive element, and the associated variation of the output power (at given DC bus voltage) of the amplifier for f=250 kHz, dc=40%, $C_1$=10 nF and $\omega'$=1000Ω. It can be inferred from FIG. 10 that $C_2$ needs to be tuned mainly in response to variations in L and that the output power decreases as R increases.

In some embodiments of tunable impedance matching, the duty cycle dc along with the IMN capacitor $C_2$ may be tuned. Then, FIG. 11 shows the values of the two tunable parameters needed to achieve impedance matching as functions of the varying R and L of the inductive element, and the associated variation of the output power (at given DC bus voltage) of the amplifier for f=250 kHz, $C_a$=640 pF, $C_1$=10 nF and $\omega'$=1000Ω. It can be inferred from FIG. 11 that $C_2$ needs to be tuned mainly in response to variations in L and that the output power decreases as R increases.

Figure 11A:
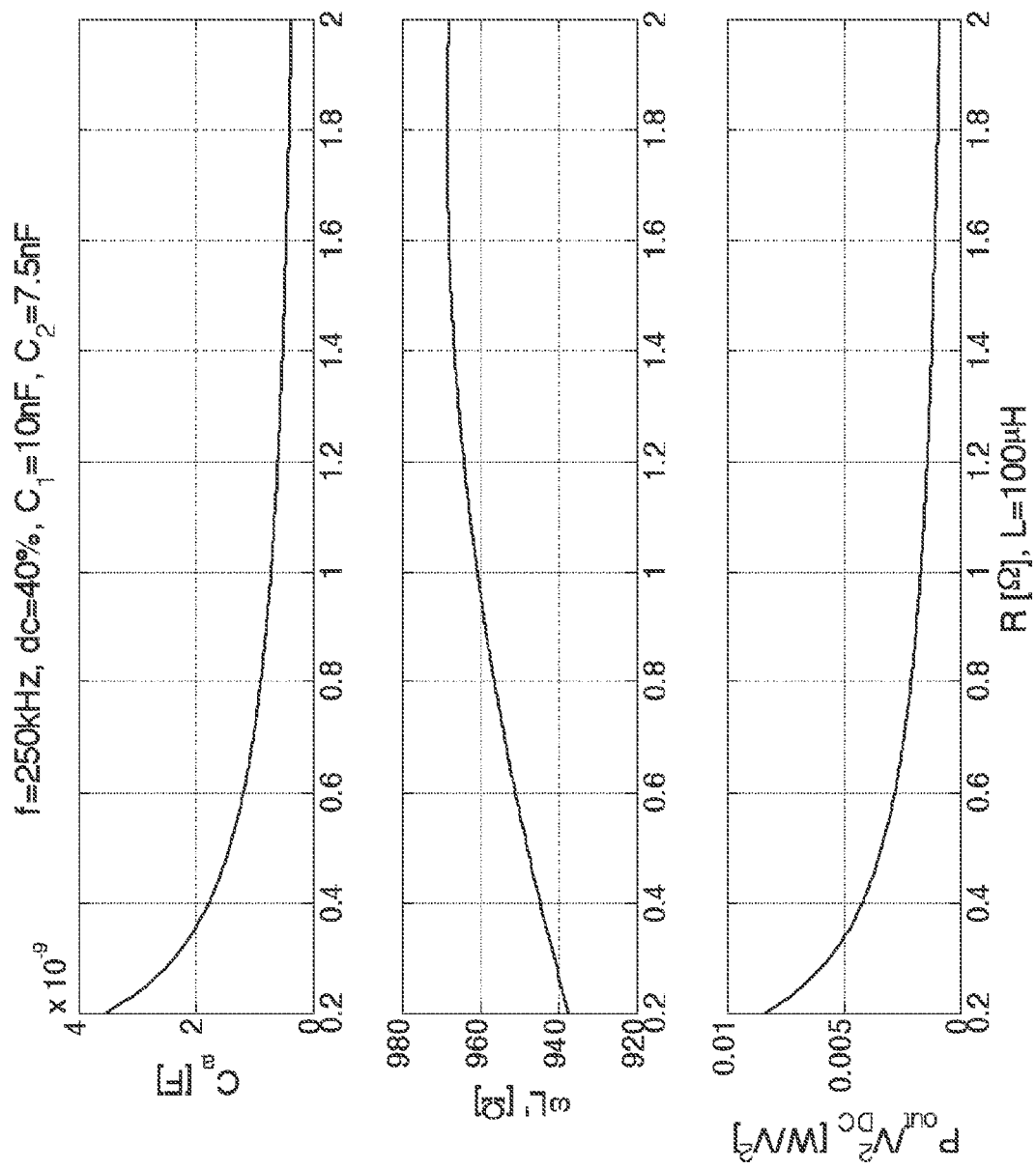
FIGS. 11A, 11B, and 11C are plots showing the effects of changes of parameters of a wireless power source.

In some embodiments of tunable impedance matching, the capacitance $C_a$ along with the IMN inductor L' may be tuned. Then, FIG. 11A shows the values of the two tunable components needed to achieve impedance matching as functions of the varying R of the inductive element, and the associated variation of the output power (at given DC bus voltage) of the amplifier for f=250 kHz, dc=40%, $C_1$=10 nF and $C_2$=7.5 nF. It can be inferred from FIG. 11A that the output power decreases as R increases.

Figure 11B:
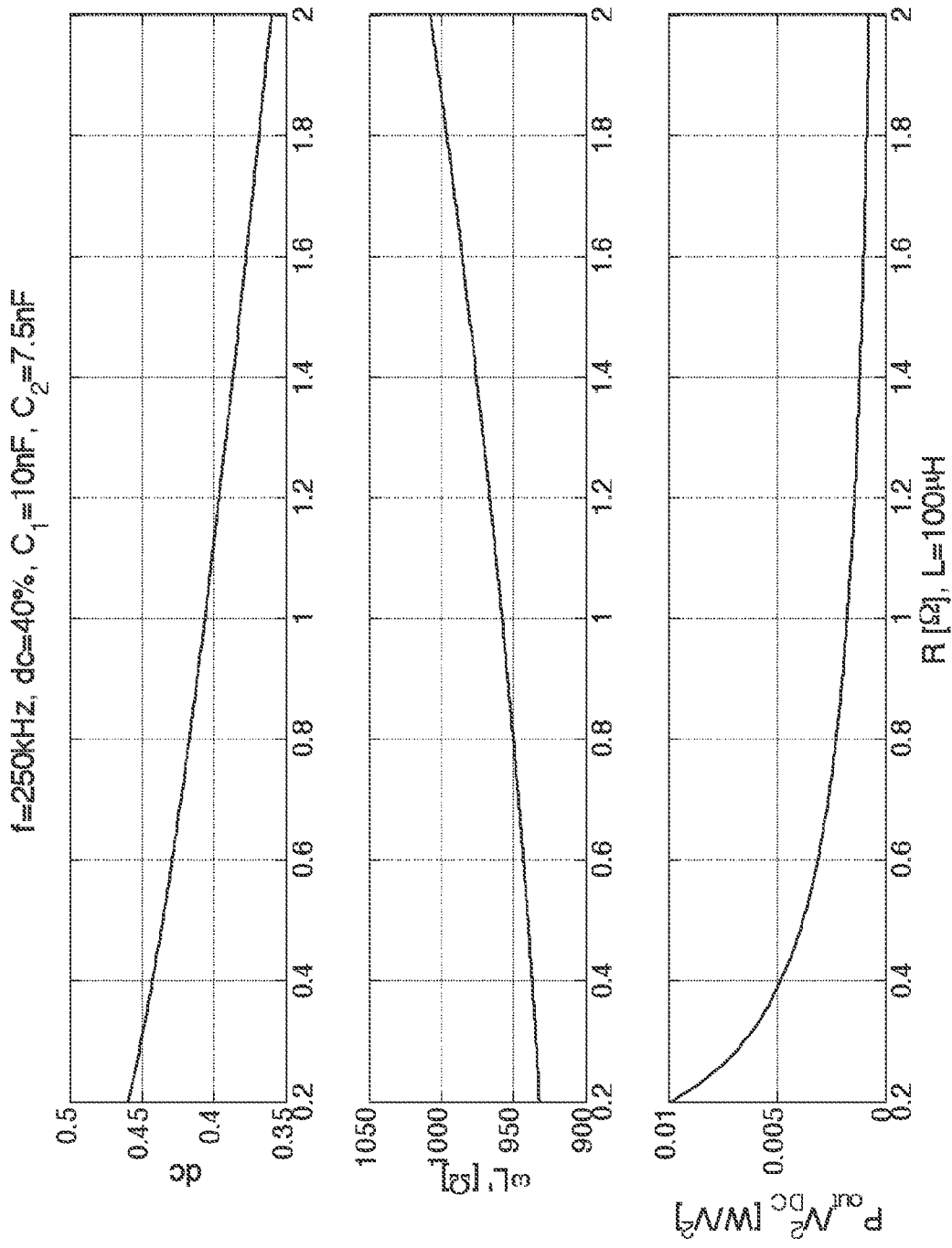

In some embodiments of tunable impedance matching, the duty cycle dc along with the IMN inductor L' may be tuned. Then, FIG. 11B shows the values of the two tunable parameters needed to achieve impedance matching as functions of the varying R of the inductive element, and the associated variation of the output power (at given DC bus voltage) of the amplifier for f=250 kHz, $C_a$=640 pF, $C_1$=10 nF and $C_2$=7.5 nF as functions of the varying R of the inductive element. It can be inferred from FIG. 11B that the output power decreases as R increases.

Figure 11C:
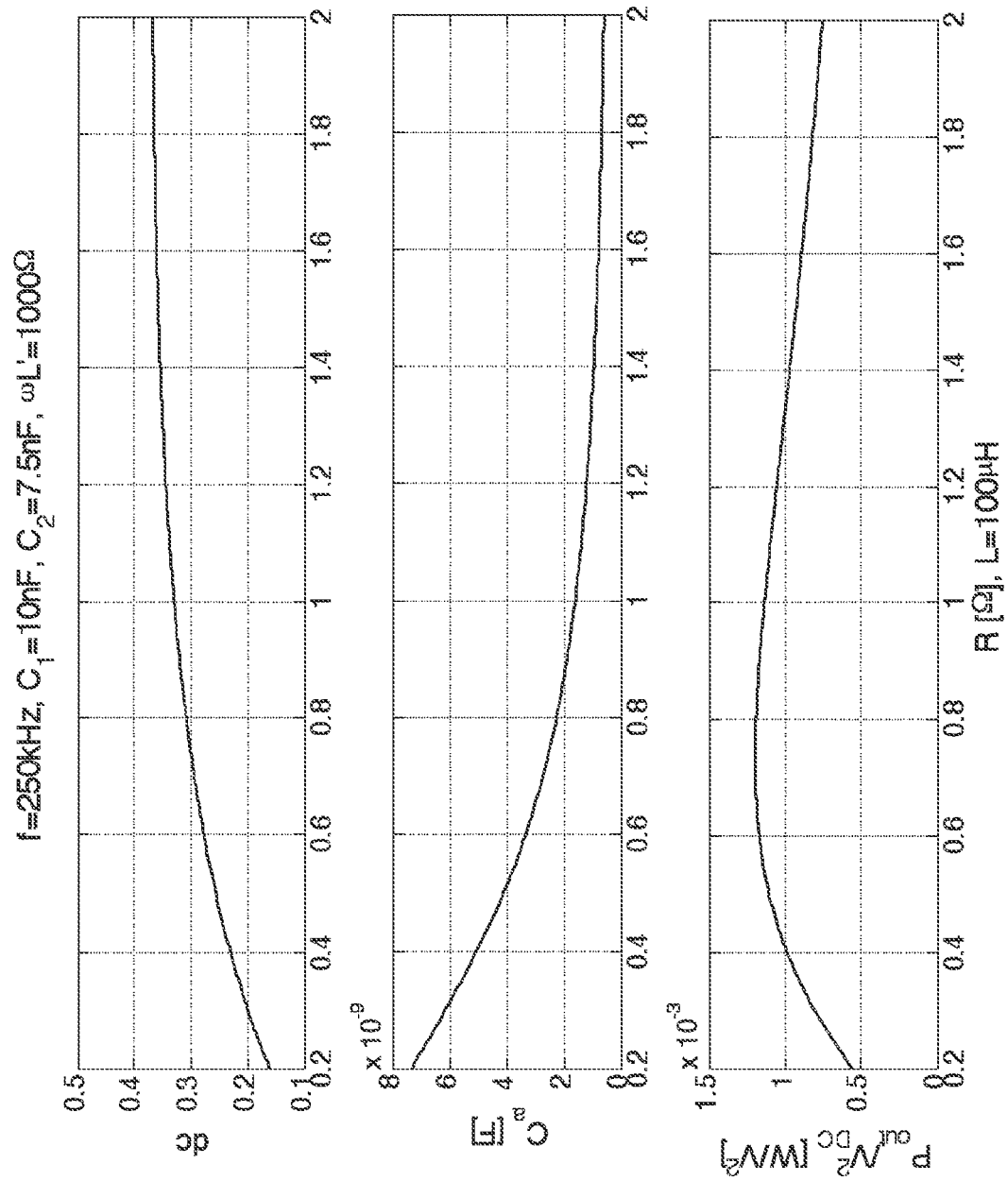

In some embodiments of tunable impedance matching, only elements in the switching amplifier may be tunable with no tunable elements in the IMN. In some embodiments the duty cycle dc along with the capacitance $C_a$ may be tuned. Then, FIG. 11C, shows the values of the two tunable parameters needed to achieve impedance matching as functions of the varying R of the inductive element, and the associated variation of the output power (at given DC bus voltage) of the amplifier for f=250 kHz, $C_1$=10 nF, $C_2$=7.5 nF and $\omega L'$=1000Ω. It can be inferred from FIG. 11C that the output power is a non-monotonic function of R. These embodiments may be able to achieve dynamic impedance matching when variations in L (and thus the resonant frequency) are modest.

Figure 12:
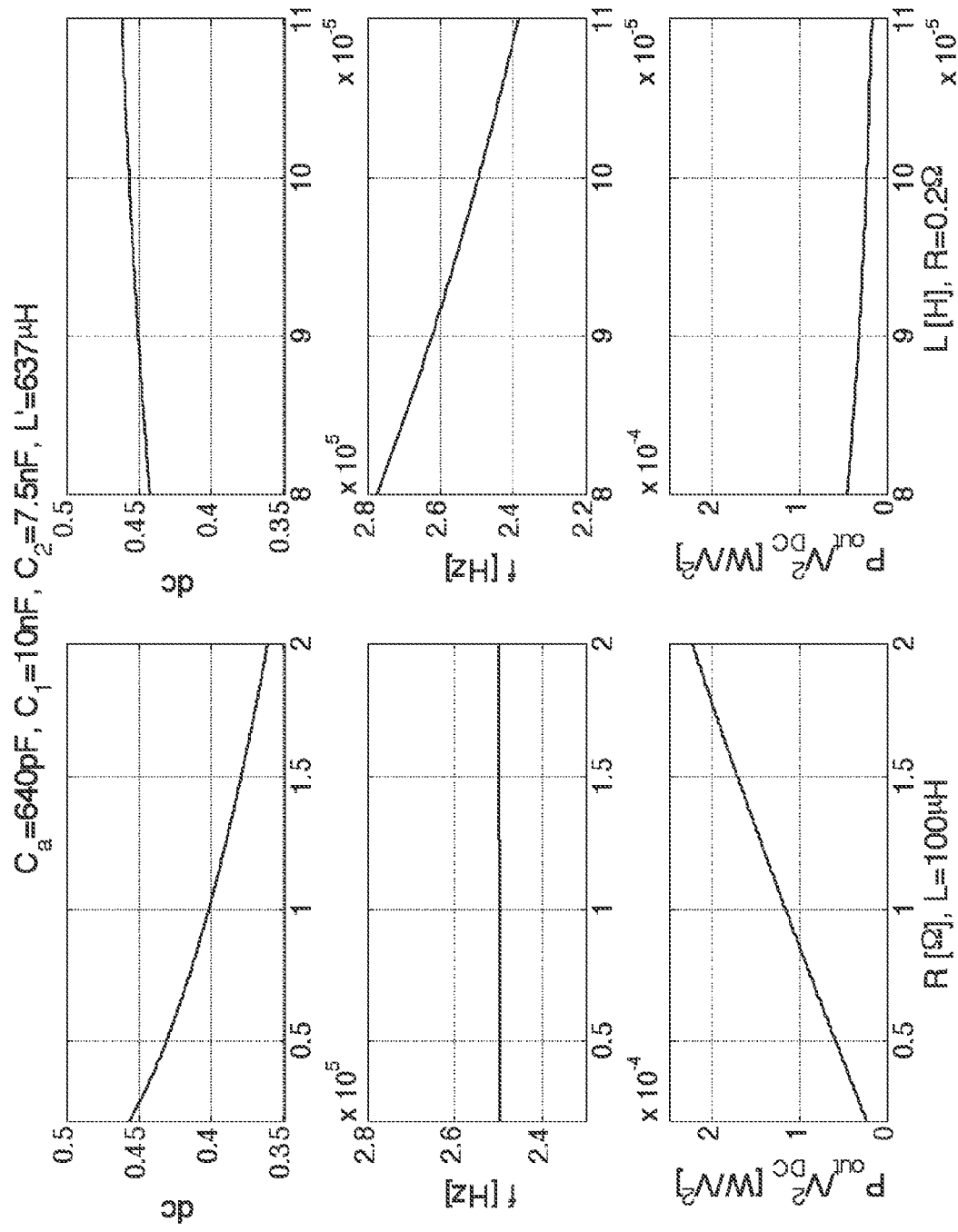
FIG. 12 shows plots of the effects of changes of parameters of a wireless power source.

In some embodiments, dynamic impedance matching with fixed elements inside the IMN, also when L is varying greatly as explained earlier, may be achieved by varying the driving frequency of the external frequency f (e.g. the switching frequency of a switching amplifier) so that it follows the varying resonant frequency of the resonator. Using the switching frequency f and the switch duty cycle dc as the two variable parameters, full impedance matching can be achieved as R and L are varying without the need of any variable components. Then, FIG. 12 shows the values of the two tunable parameters needed to achieve impedance matching as functions of the varying R and L of the inductive element, and the associated variation of the output power (at given DC bus voltage) of the amplifier for $C_a$=640 pF, $C_1$=10 nF, $C_2$=7.5 nF and L'=637 μH. It can be inferred from FIG. 12 that the frequency f needs to be tuned mainly in response to variations in L, as explained earlier.

Tunable Impedance Matching for Systems of Wireless Power Transmission

In applications of wireless power transfer the low-loss inductive element may be the coil of a source resonator coupled to one or more device resonators or other resonators, such as repeater resonators, for example. The impedance of the inductive element R+jωL may include the reflected impedances of the other resonators on the coil of the source resonator. Variations of R and L of the inductive element may occur due to external perturbations in the vicinity of the source resonator and/or the other resonators or thermal drift of components. Variations of R and L of the inductive element may also occur during normal use of the wireless power transmission system due to relative motion of the devices and other resonators with respect to the source. The relative motion of these devices and other resonators with respect to the source, or relative motion or position of other sources, may lead to varying coupling (and thus varying reflected impedances) of the devices to the source. Furthermore, variations of R and L of the inductive element may also occur during normal use of the wireless power transmission system due to changes within the other coupled resonators, such as changes in the power draw of their loads. All the methods and embodiments disclosed so far apply also to this case in order to achieve dynamic impedance matching of this inductive element to the external circuit driving it.

To demonstrate the presently disclosed dynamic impedance matching methods for a wireless power transmission system, consider a source resonator including a low-loss source coil, which is inductively coupled to the device coil of a device resonator driving a resistive load.

In some embodiments, dynamic impedance matching may be achieved at the source circuit. In some embodiments, dynamic impedance matching may also be achieved at the device circuit. When full impedance matching is obtained (both at the source and the device), the effective resistance of the source inductive element (namely the resistance of the source coil $R_s$ plus the reflected impedance from the device) is $R=R_s\sqrt{1+U_{sd}^2}$. (Similarly the effective resistance of the device inductive element is $R_d\sqrt{1+U_{sd}^2}$, where $R_d$ is the resistance of the device coil.) Dynamic variation of the mutual inductance between the coils due to motion results in a dynamic variation of $U_{sd}=\omega M_{sd}/\sqrt{R_s R_d}$. Therefore, when both source and device are dynamically tuned, the variation of mutual inductance is seen from the source circuit side as a variation in the source inductive element resistance R. Note that in this type of variation, the resonant frequencies of the resonators may not change substantially, since L may not be changing. Therefore, all the methods and examples presented for dynamic impedance matching may be used for the source circuit of the wireless power transmission system.

Note that, since the resistance R represents both the source coil and the reflected impedances of the device coils to the source coil, in FIGS. 9-12, as R increases due to the increasing U, the associated wireless power transmission efficiency increases. In some embodiments, an approximately constant power may be required at the load driven by the device circuitry. To achieve a constant level of power transmitted to the device, the required output power of the source circuit may need to decrease as U increases. If dynamic impedance matching is achieved via tuning some of the amplifier parameters, the output power of the amplifier may vary accordingly. In some embodiments, the automatic variation of the output power is preferred to be monotonically decreasing with R, so that it matches the constant device power requirement. In embodiments where the output power level is accomplished by adjusting the DC driving voltage of the power generator, using an impedance matching set of tunable parameters which leads to monotonically decreasing output power vs. R will imply that constant power can be kept at the power load in the device with only a moderate adjustment of the DC driving voltage. In embodiments, where the "knob" to adjust the output power level is the duty cycle dc or the phase of a switching amplifier or a component inside an Impedance Matching Network, using an impedance matching set of tunable parameters which leads to monotonically decreasing output power vs. R will imply that constant power can be kept at the power load in the device with only a moderate adjustment of this power "knob".

In the examples of FIGS. 9-12, if $R_s$=0.19Ω, then the range R=0.2–2Ω corresponds approximately to $U_{sd}$=0.3–10.5. For these values, in FIG. 14, we show with dashed lines the output power (normalized to DC voltage squared) required to keep a constant power level at the load, when both source and device are dynamically impedance matched. The similar trend between the solid and dashed lines explains why a set of tunable parameters with such a variation of output power may be preferable.

In some embodiments, dynamic impedance matching may be achieved at the source circuit, but impedance matching may not be achieved or may only partially be achieved at the device circuit. As the mutual inductance between the source and device coils varies, the varying reflected impedance of the device to the source may result in a variation of both the effective resistance R and the effective inductance L of the source inductive element. The methods presented so far for dynamic impedance matching are applicable and can be used for the tunable source circuit of the wireless power transmission system.

Figure 14:
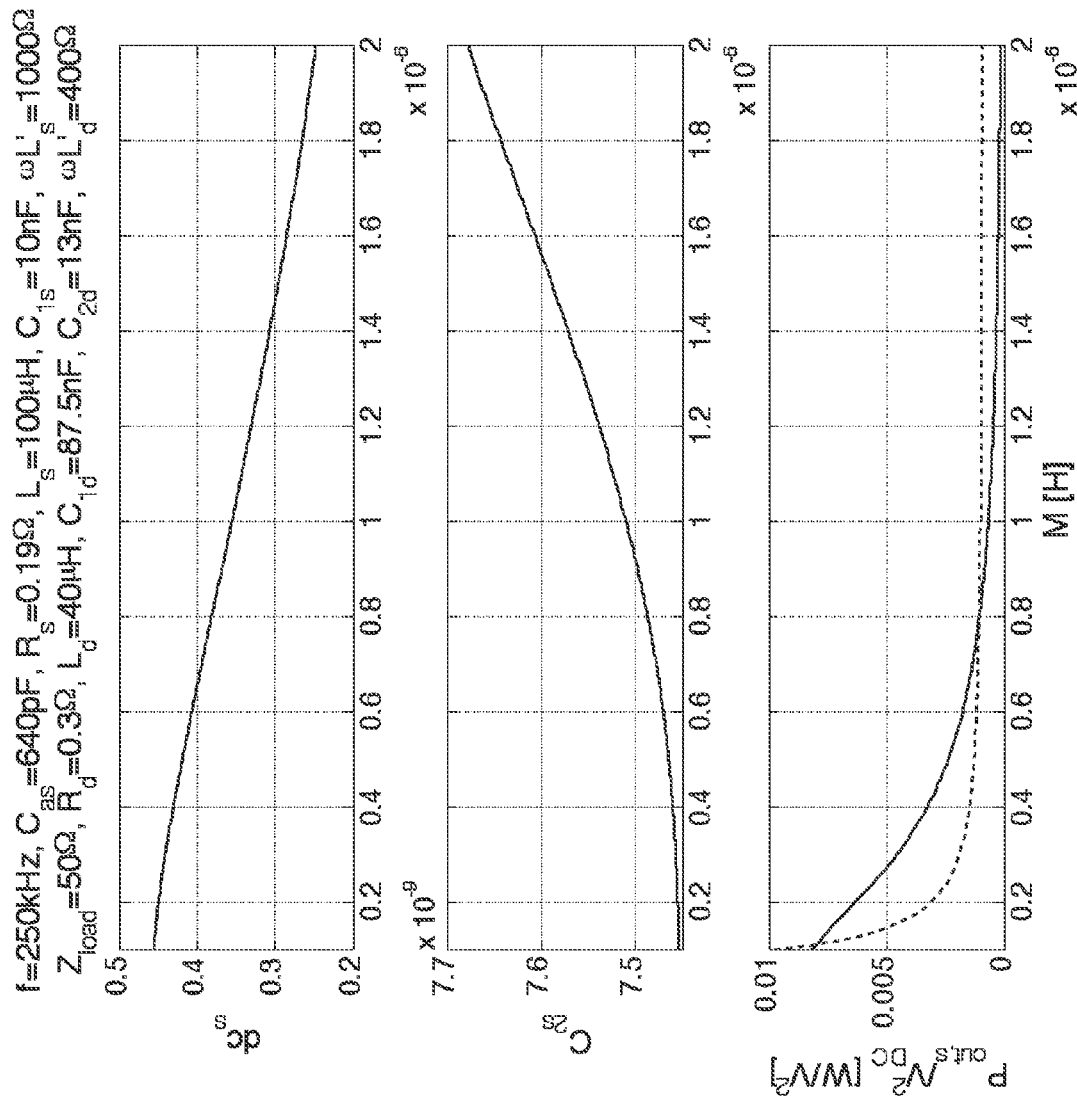
FIG. 14 shows plots of the effects of changes of parameters of a wireless power source.

As an example, consider the circuit of FIG. 14, where f=250 kHz, $C_a$=640 pF, $R_s$=0.19Ω, $L_s$=100 µH, $C_{1s}$=10 nF, $\omega L'_s$=1000Ω, $R_d$=0.3Ω, $L_d$=40 µH, $C_{1d}$=87.5 nF, $C_{2d}$=13 nF, $\omega L'_d$=400Ω and $Z_l$=50Ω, where s and d denote the source and device resonators respectively and the system is matched at $U_{sd}$=3. Tuning the duty cycle dc of the switching amplifier and the capacitor $C_{2s}$ may be used to dynamically impedance match the source, as the non-tunable device is moving relatively to the source changing the mutual inductance M between the source and the device. In FIG. 14, we show the required values of the tunable parameters along with the output power per DC voltage of the amplifier. The dashed line again indicates the output power of the amplifier that would be needed so that the power at the load is a constant value.

Figure 13:
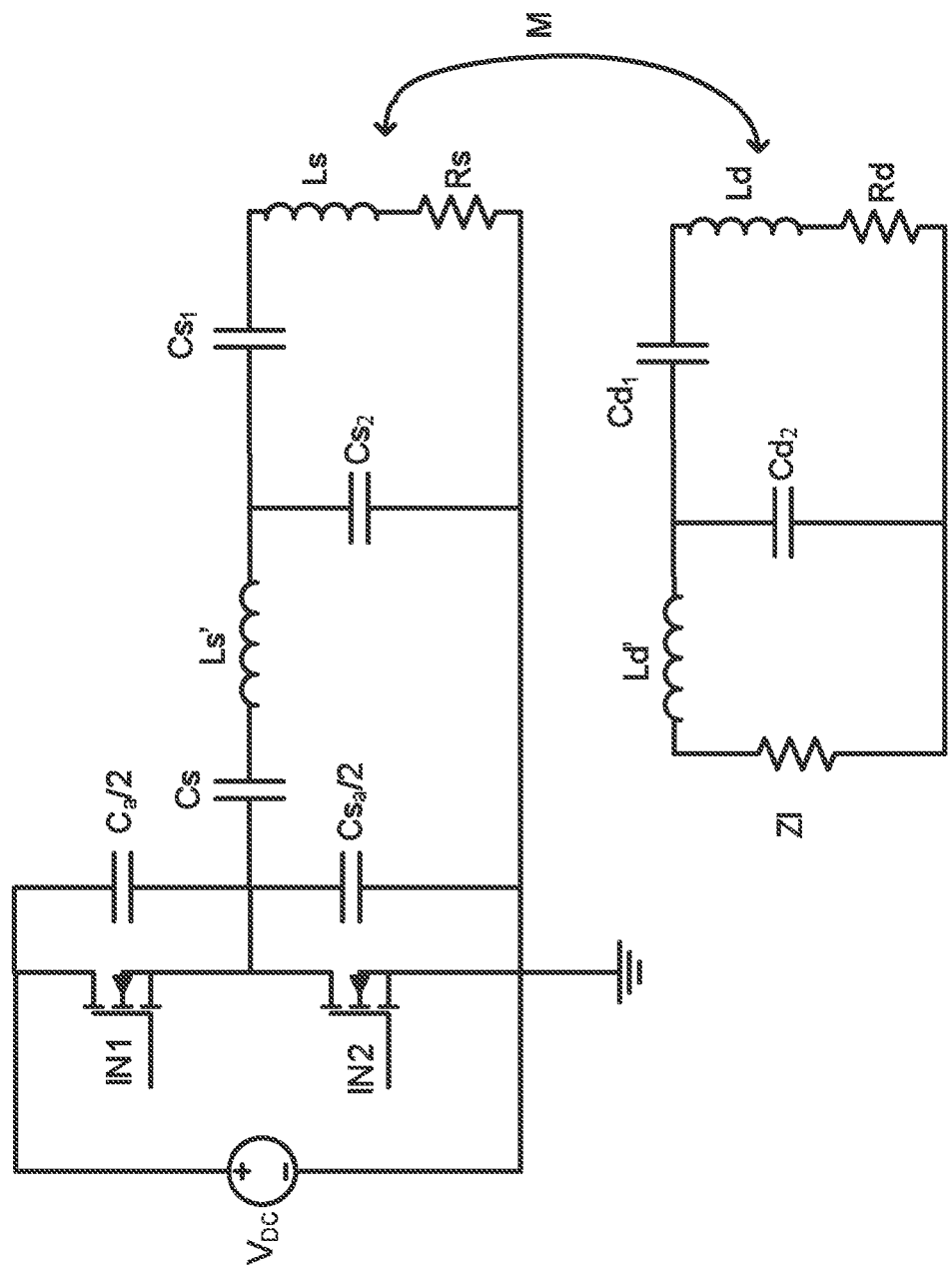
FIG. 13 is a simplified circuit diagram of a wireless energy transfer system comprising a wireless power source with a switching amplifier and a wireless power device.

In some embodiments, tuning the driving frequency f of the source driving circuit may still be used to achieve dynamic impedance matching at the source for a system of wireless power transmission between the source and one or more devices. As explained earlier, this method enables full dynamic impedance matching of the source, even when there are variations in the source inductance $L_s$ and thus the source resonant frequency. For efficient power transmission from the source to the devices, the device resonant frequencies must be tuned to follow the variations of the matched driving and source-resonant frequencies. Tuning a device capacitance (for example, in the embodiment of FIG. 13 $C_{1d}$ or $C_{2d}$) may be necessary, when there are variations in the resonant frequency of either the source or the device resonators. In fact, in a wireless power transfer system with multiple sources and devices, tuning the driving frequency alleviates the need to tune only one source-object resonant frequency, however, all the rest of the objects may need a mechanism (such as a tunable capacitance) to tune their resonant frequencies to match the driving frequency.

Resonator Thermal Management

In wireless energy transfer systems, some portion of the energy lost during the wireless transfer process is dissipated as heat. Energy may be dissipated in the resonator components themselves. For example, even high-Q conductors and components have some loss or resistance, and these conductors and components may heat up when electric currents and/or electromagnetic fields flow through them. Energy may be dissipated in materials and objects around a resonator. For example, eddy currents dissipated in imperfect conductors or dielectrics surrounding or near-by the resonator may heat up those objects. In addition to affecting the material properties of those objects, this heat may be transferred through conductive, radiative, or convective processes to the resonator components. Any of these heating effects may affect the resonator Q, impedance, frequency, etc., and therefore the performance of the wireless energy transfer system.

In a resonator comprising a block or core of magnetic material, heat may be generated in the magnetic material due to hysteresis losses and to resistive losses resulting from induced eddy currents. Both effects depend on the magnetic flux density in the material, and both can create significant amounts of heat, especially in regions where the flux density or eddy currents may be concentrated or localized. In addition to the flux density, the frequency of the oscillating magnetic field, the magnetic material composition and losses, and the ambient or operating temperature of the magnetic material may all impact how hysteresis and resistive losses heat the material.

In embodiments, the properties of the magnetic material such as the type of material, the dimensions of the block, and the like, and the magnetic field parameters may be chosen for specific operating power levels and environments to minimize heating of the magnetic material. In some embodiments, changes, cracks, or imperfections in a block of magnetic material may increase the losses and heating of the magnetic material in wireless power transmission applications.

For magnetic blocks with imperfections, or that are comprised of smaller size tiles or pieces of magnetic material arranged into a larger unit, the losses in the block may be uneven and may be concentrated in regions where there are inhomogeneities or relatively narrow gaps between adjacent tiles or pieces of magnetic material. For example, if an irregular gap exists in a magnetic block of material, then the effective reluctance of various magnetic flux paths through the material may be substantially irregular and the magnetic field may be more concentrated in portions of the block where the magnetic reluctance is lowest. In some cases, the effective reluctance may be lowest where the gap between tiles or pieces is narrowest or where the density of imperfections is lowest. Because the magnetic material guides the magnetic field, the magnetic flux density may not be substantially uniform across the block, but may be concentrated in regions offering relatively lower reluctance. Irregular concentrations of the magnetic field within a block of magnetic material may not be desirable because they may result in uneven losses and heat dissipation in the material.

Figure 15:
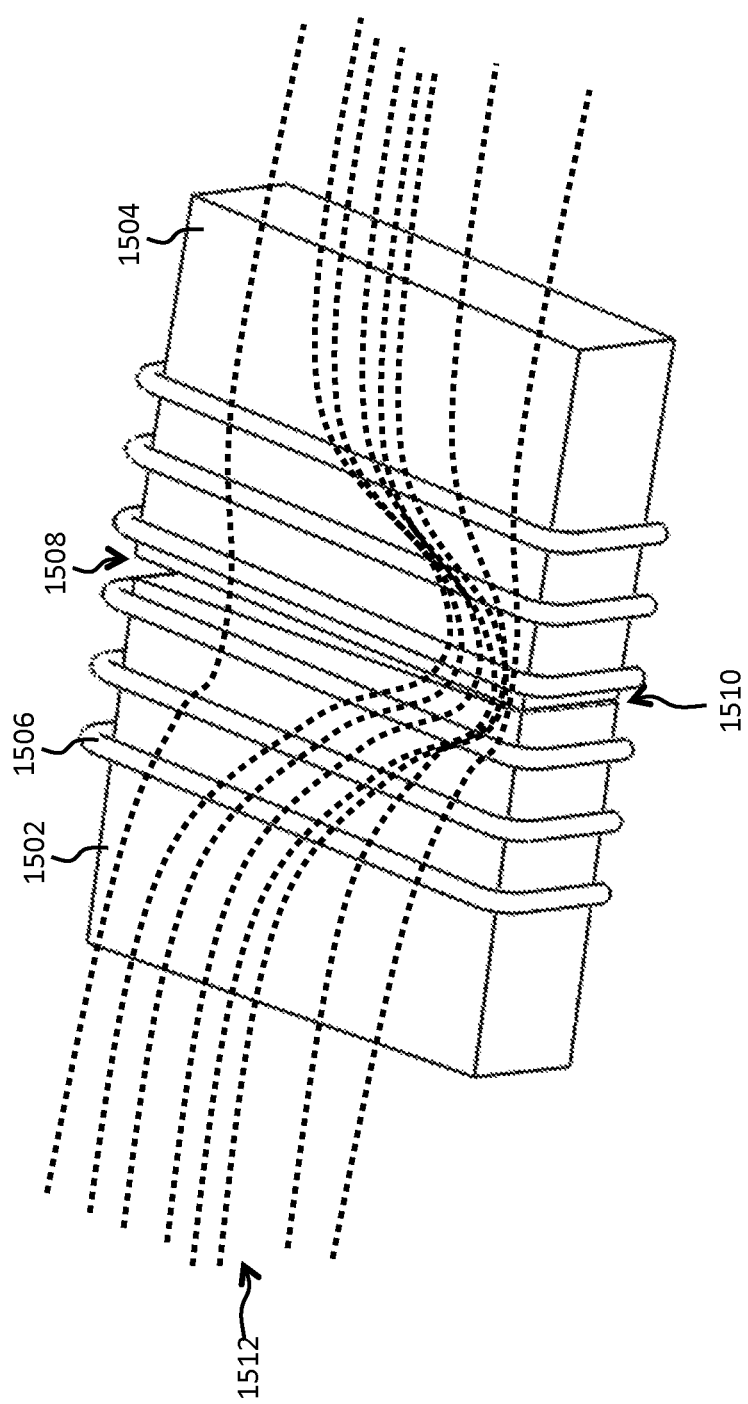
FIG. 15 is a diagram of a resonator showing possible non-uniform magnetic field distributions due to irregular spacing between tiles of magnetic material.

For example, consider a magnetic resonator comprising a conductor 1506 wrapped around a block of magnetic material composed of two individual tiles 1502, 1504 of magnetic material joined such that they form a seam 1508 that is perpendicular to the axis of the conductor 1506 loops as depicted in FIG. 15. An irregular gap in the seam 1508 between the tiles of magnetic material 1502, 1504 may force the magnetic field 1512 (represented schematically by the dashed magnetic field lines) in the resonator to concentrate in a sub region 1510 of the cross section of the magnetic material. Since the magnetic field will follow the path of least reluctance, a path including an air gap between two pieces of magnetic material may create an effectively higher reluctance path than one that traverses the width of the magnetic material at a point where the pieces of magnetic materials touch or have a smaller air gap. The magnetic flux density may therefore preferentially flow through a relatively small cross area of the magnetic material resulting in a high concentration of magnetic flux in that small area 1510.

In many magnetic materials of interest, more inhomogeneous flux density distributions lead to higher overall losses. Moreover, the more inhomogeneous flux distribution may result in material saturation and cause localized heating of the area in which the magnetic flux is concentrated. The localized heating may alter the properties of the magnetic material, in some cases exacerbating the losses. For example, in the relevant regimes of operation of some materials, hysteresis and resistive losses increase with temperature. If heating the material increases material losses, resulting in more heating, the temperature of the material may continue to increase and even runaway if no corrective action is taken. In some instances, the temperature may reach 100 C. or more and may degrade the properties of the magnetic material and the performance of wireless power transfer. In some instances, the magnetic materials may be damaged, or the surrounding electronic components, packaging and/or enclosures may be damaged by the excessive heat.

In embodiments, variations or irregularities between tiles or pieces of the block of magnetic material may be minimized by machining, polishing, grinding, and the like, the edges of the tiles or pieces to ensure a tight fit between tiles of magnetic materials providing a substantially more uniform reluctance through the whole cross section of the block of magnetic material. In embodiments, a block of magnetic material may require a means for providing a compression force between the tiles to ensure the tiles are pressed tight together without gaps. In embodiments, an adhesive may be used between the tiles to ensure they remain in tight contact.

In embodiments the irregular spacing of adjacent tiles of magnetic material may be reduced by adding a deliberate gap between adjacent tiles of magnetic material. In embodiments a deliberate gap may be used as a spacer to ensure even or regular separations between magnetic material tiles or pieces. Deliberate gaps of flexible materials may also reduce irregularities in the spacings due to tile movement or vibrations. In embodiments, the edges of adjacent tiles of magnetic material may be taped, dipped, coated, and the like with an electrical insulator, to prevent eddy currents from flowing through reduced cross-sectional areas of the block, thus lowering the eddy current losses in the material. In embodiments a separator may be integrated into the resonator packaging. The spacer may provide a spacing of 1 mm or less.

In embodiments, the mechanical properties of the spacer between tiles may be chosen so as to improve the tolerance of the overall structure to mechanical effects such as changes in the dimensions and/or shape of the tiles due to intrinsic effects (e.g. magnetostriction, thermal expansion, and the like) as well as external shocks and vibrations. For example, the spacer may have a desired amount of mechanical give to accommodate the expansion and/or contraction of individual tiles, and may help reduce the stress on the tiles when they are subjected to mechanical vibrations, thus helping to reduce the appearance of cracks and other defects in the magnetic material.

In embodiments, it may be preferable to arrange the individual tiles that comprise the block of magnetic material to minimize the number of seams or gaps between tiles that are perpendicular to the dipole moment of the resonator. In embodiments it may be preferable to arrange and orient the tiles of magnetic material to minimize the gaps between tiles that are perpendicular to the axis formed by the loops of a conductor comprising the resonator.

Figure 16:
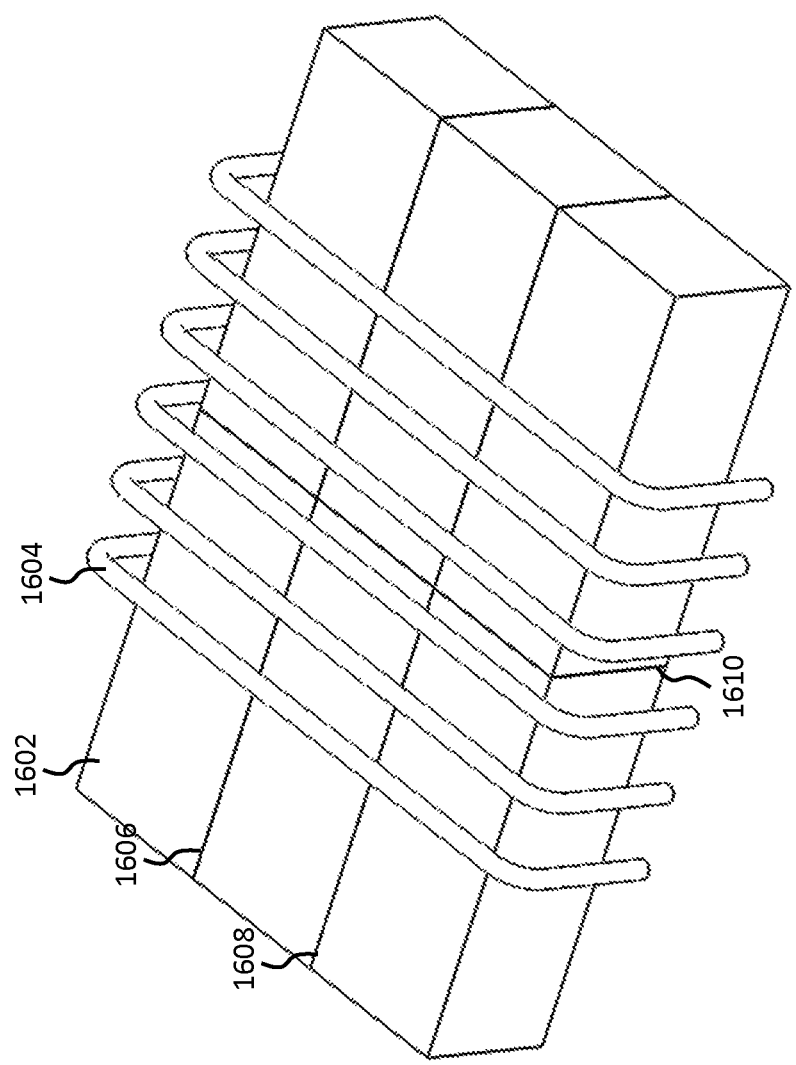
FIG. 16 is a resonator with an arrangement of tiles in a block of magnetic material that may reduce hotspots in the magnetic material block.

For example, consider the resonator structure depicted in FIG. 16. The resonator comprises a conductor 1604 wrapped around a block of magnetic material comprising six separate individual tiles 1602 arranged in a three by two array. The arrangement of tiles results in two tile seams 1606, 1608 when traversing the block of magnetic material in one direction, and only one tile seam 1610 when traversing the block of magnetic material in the orthogonal direction. In embodiments, it may be preferable to wrap the conductor wire 1604 around the block of magnetic material such that the dipole moment of the resonator is perpendicular to the fewest number of tile seams. The inventors have observed that there is relatively less heating induced around seams and gaps 1606, 1608 that are parallel to the dipole moment of the resonator. Seams and gaps that run perpendicular to the dipole moment of the resonator may also be referred to as critical seams or critical seam areas. It may still be desirable, however, to electrically insulate gaps that run parallel to the dipole moment of the resonator (such as 1606 and 1608) so as to reduce eddy current losses. Uneven contact between tiles separated by such parallel gaps may cause eddy currents to flow through narrow contact points, leading to large losses at such points.

In embodiments, irregularities in spacing may be tolerated with adequate cooling of the critical seam areas to prevent the localized degradation of material properties when the magnetic material heats up. Maintaining the temperature of the magnetic material below a critical temperature may prevent a runaway effect caused by a sufficiently high temperature. With proper cooling of the critical seam area, the wireless energy transfer performance may be satisfactory despite the additional loss and heating effects due to irregular spacing, cracks, or gaps between tiles.

Effective heatsinking of the resonator structure to prevent excessive localized heating of the magnetic material poses several challenges. Metallic materials that are typically used for heatsinks and thermal conduction can interact with the magnetic fields used for wireless energy transfer by the resonators and affect the performance of the system. Their location, size, orientation, and use should be designed so as to not excessively lower the perturbed Q of the resonators in the presence of these heatsinking materials. In addition, owing to the relatively poor thermal conductivity of magnetic materials such as ferrites, a relatively large contact area between the heatsink and the magnetic material may be required to provide adequate cooling which may require placement of substantial amount of lossy materials close to the magnetic resonator.

In embodiments, adequate cooling of the resonator may be achieved with minimal effect on the wireless energy transfer performance with strategic placement of thermally conductive materials. In embodiments, strips of thermally conductive material may be placed in between loops of conductor wire and in thermal contact with the block of magnetic material.

One exemplary embodiment of a resonator with strips of thermally conductive material is depicted in FIG. 17. FIG. 17A shows the resonator structure without the conducting strips and with the block of magnetic material comprising smaller tiles of magnetic material forming gaps or seams. Strips of thermally conductive 1708 material may be placed in between the loops of the conductor 1702 and in thermal contact with the block of magnetic material 1704 as depicted in FIGS. 17B and 17C. To minimize the effects of the strips on the parameters of the resonator, in some embodiments it may be preferable to arrange the strips parallel to the loops of conductor or perpendicular to the dipole moment of the resonator. The strips of conductor may be placed to cover as much or as many of the seams or gaps between the tiles as possible especially the seams between tiles that are perpendicular to the dipole moment of the resonator.

In embodiments the thermally conductive material may comprise copper, aluminum, brass, thermal epoxy, paste, pads, and the like, and may be any material that has a thermal conductivity that is at least that of the magnetic material in the resonator (~5 W/(K−m) for some commercial ferrite materials). In embodiments where the thermally conductive material is also electrically conducting, the material may require a layer or coating of an electrical insulator to prevent shorting and direct electrical contact with the magnetic material or the loops of conductor of the resonator.

In embodiments the strips of thermally conductive material may be used to conduct heat from the resonator structure to a structure or medium that can safely dissipate the thermal energy. In embodiments the thermally conductive strips may be connected to a heat sink such as a large plate located above the strips of conductor that can dissipate the thermal energy using passive or forced convection, radiation, or conduction to the environment. In embodiments the system may include any number of active cooling systems that may be external or internal to the resonator structure that can dissipate the thermal energy from the thermally conducting strips and may include liquid cooling systems, forced air systems, and the like. For example, the thermally conducting strips may be hollow or comprise channels for coolant that may be pumped or forced through to cool the magnetic material. In embodiments, a field deflector made of a good electrical conductor (such as copper, silver, aluminum, and the like) may double as part of the heatsinking apparatus. The addition of thermally and electrically conducting strips to the space between the magnetic material and the field deflector may have a marginal effect on the perturbed Q, as the electromagnetic fields in that space are typically suppressed by the presence of the field deflector. Such conducting strips may be thermally connected to both the magnetic material and the field deflector to make the temperature distribution among different strips more homogeneous.

In embodiments the thermally conducting strips are spaced to allow at least one loop of conductor to wrap around the magnetic material. In embodiments the strips of thermally conductive material may be positioned only at the gaps or seams of the magnetic material. In other embodiments, the strips may be positioned to contact the magnetic material at substantially throughout its complete length. In other embodiments, the strips may be distributed to match the flux density within the magnetic material. Areas of the magnetic material which under normal operation of the resonator may have higher magnetic flux densities may have a higher density of contact with the thermally conductive strips. In embodiments depicted in FIG. 17A) for example, the highest magnetic flux density in the magnetic material may be observed toward the center of the block of magnetic material and the lower density may be toward the ends of the block in the direction of the dipole moment of the resonator.

To show how the use of thermally conducting strips helps to reduce the overall temperature in the magnetic material as well as the temperature at potential hot spots, the inventors have performed a finite element simulation of a resonator structure similar to that depicted in FIG. 17C. The structure was simulated operating at a frequency of 235 kHz and comprising a block of EPCOS N95 magnetic material measuring 30 cm×30 cm×5 mm excited by 10 turns of litz wire (symmetrically placed at 25 mm, 40 mm, 55 mm, 90 mm and 105 mm from the plane of symmetry of the structure) carrying 40 A of peak current each, and thermally connected to a 50 cm×50 cm×4 mm field deflector by means of three 3×¾×1' hollow square tubes (⅛" wall thickness) of aluminum (alloy 6063) whose central axes are placed at −75 mm, 0 mm, and +75 from the symmetry plane of the structure. The perturbed Q due to the field deflector and hollow tubes was found to be 1400 (compared to 1710 for the same structure without the hollow tubes). The power dissipated in the shield and tubes was calculated to be 35.6 W, while that dissipated in the magnetic material was 58.3 W. Assuming the structure is cooled by air convection and radiation and an ambient temperature of 24° C., the maximum temperature in the structure was 85° C. (at points in the magnetic material approximately halfway between the hollow tubes) while the temperature in parts of the magnetic material in contact with the hollow tubes was approximately 68° C. By comparison, the same resonator without the thermally conducting hollow tubes dissipated 62.0 W in the magnetic material for the same excitation current of 40 W peak and the maximum temperature in the magnetic material was found to be 111° C.

The advantage of the conducting strips is more apparent still if we introduce a defect in a portion of the magnetic material that is in good thermal contact with the tubes. An air gap 10 cm long and 0.5 mm placed at the center of the magnetic material and oriented perpendicular to the dipole moment increases the power dissipated in the magnetic material to 69.9 W (the additional 11.6 W relative to the previously discussed no-defect example being highly concentrated in the vicinity of the gap), but the conducting tube ensures that the maximum temperature in the magnetic material has only a relative modest increase of 11° C. to 96° C. In contrast, the same defect without the conducting tubes leads to a maximum temperature of 161° C. near the defect. Cooling solutions other than convection and radiation, such as thermally connecting the conducting tubes body with large thermal mass or actively cooling them, may lead to even lower operational temperatures for this resonator at the same current level.

In embodiments thermally conductive strips of material may be positioned at areas that may have the highest probability of developing cracks that may cause irregular gaps in the magnetic material. Such areas may be areas of high stress or strain on the material, or areas with poor support or backing from the packaging of the resonator. Strategically positioned thermally conductive strips may ensure that as cracks or irregular gaps develop in the magnetic material, the temperature of the magnetic material will be maintained below its critical temperature. The critical temperature may be defined as the Curie temperature of the magnetic material, or any temperature at which the characteristics of the resonator have been degraded beyond the desired performance parameters.

In embodiments the heastsinking structure may provide mechanical support to the magnetic material. In embodiments the heatsinking structure may be designed to have a desired amount of mechanical give (e.g., by using epoxy, thermal pads, and the like having suitable mechanical properties to thermally connect different elements of the structure) so as to provide the resonator with a greater amount of tolerance to changes in the intrinsic dimensions of its elements (due to thermal expansion, magnetostriction, and the like) as well as external shocks and vibrations, and prevent the formation of cracks and other defects.

In embodiments where the resonator comprises orthogonal windings wrapped around the magnetic material, the strips of conducting material may be tailored to make thermal contact with the magnetic material within areas delimited by two orthogonal sets of adjacent loops. In embodiments a strip may contain appropriate indentations to fit around the conductor of at least one orthogonal winding while making thermal contact with the magnetic material at least one point. In embodiments the magnetic material may be in thermal contact with a number of thermally conducting blocks placed between adjacent loops. The thermally conducting blocks may be in turn thermally connected to one another by means of a good thermal conductor and/or heatsinked.

Throughout this description although the term thermally conductive strips of material was used as an exemplary specimen of a shape of a material it should be understood by those skilled in the art that any shapes and contours may be substituted without departing from the spirit of the inventions. Squared, ovals, strips, dots, elongated shapes, and the like would all be within the spirit of the present invention.

Medical and Surgical Applications

Wireless power transfer may be used in hospital and operating room environments. A large number of electric and electronic equipment is used in hospitals and operating rooms to monitor patients, administer medications, perform medical procedures, maintain administrative and medical records, and the like. The electric and electronic equipment is often moved, repositioned, moved with a patient, or attached to a patient. The frequent movement may result in problems related to power delivery to the devices. Equipment and electronic devices that are often moved and repositioned may create a power cable hazards and management problem due to cables that become tangled, strained, unplugged, that become a tripping hazard, and the like. Devices with a battery backup that are capable of operating for a period of time without a direct electrical connection require frequent recharging or plugging and unplugging from electrical outlets every time a device is used or repositioned. Wireless power transfer may be used to eliminate the problems and hazards of traditional wired connection in hospital and operating room environments.

Wireless power transfer may be used to power surgical robots, equipment, sensors, and the like. Many medical procedures and surgical operations utilize robots or robotic equipment to perform or aid in medical procedures or operations. Wireless power transfer may be used to transfer power to the robotic equipment, to parts of the equipment, or to instruments or tools manipulated by the equipment which may reduce the potentially hazardous and troublesome wiring of the systems.

Figure 18:
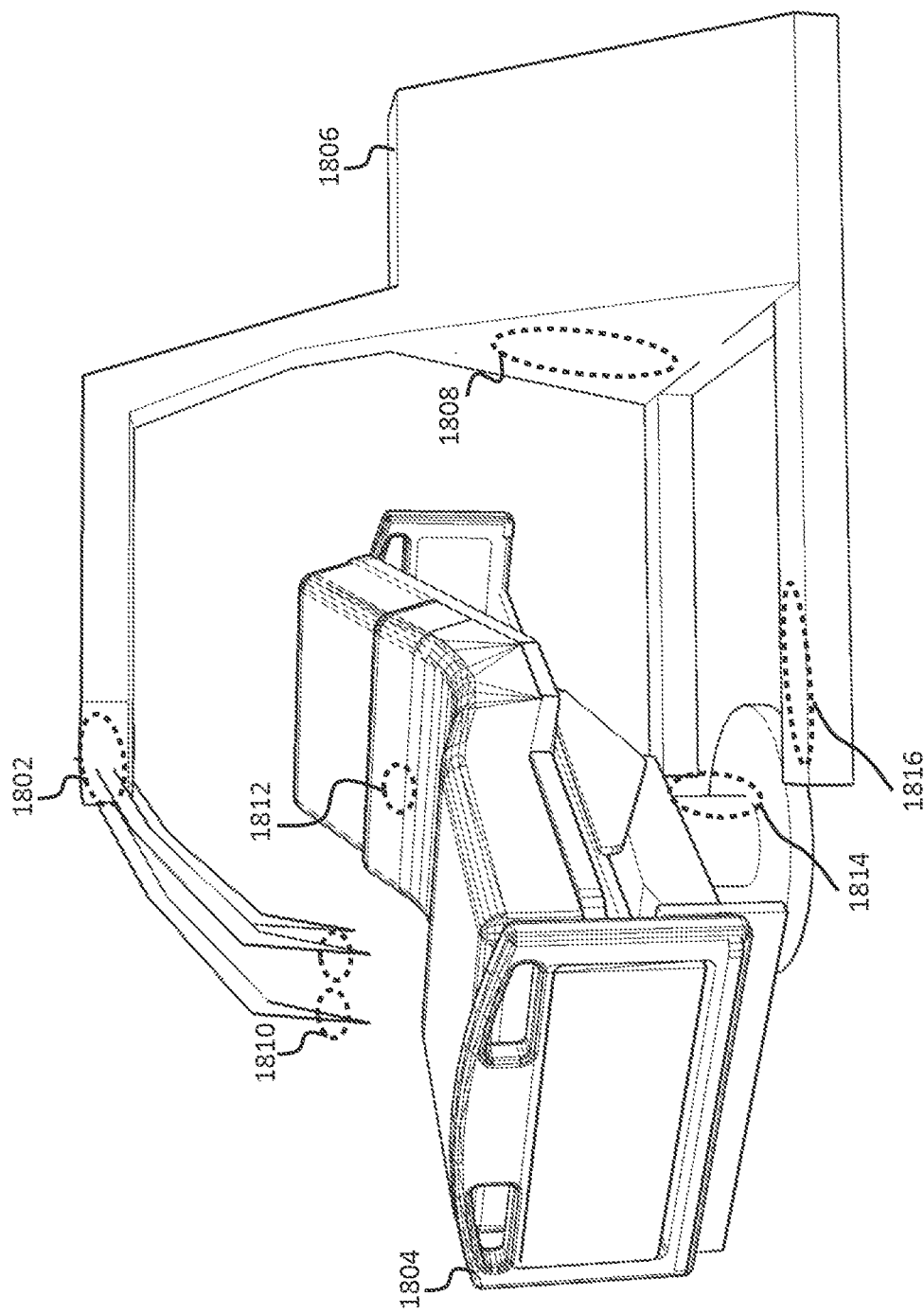
FIG. 18 is an embodiment of a surgical robot and a hospital bed with wireless energy sources and devices.

One example configuration of a surgical robot utilizing wireless power transfer is shown in FIG. 18. The figure depicts a surgical robot 1806 and an operating bed 1804. The surgical robot may be powered wirelessly from a wireless source embedded in the bed, floor, or other structure. The wireless energy transfer may allow the robot to be repositioned without changing the position of power cables. In some embodiments the surgical robot may receive power wirelessly for operation or charging its battery or energy storage system. The received power may be distributed to systems or parts such as motors, controllers, and the like via conventional wired methods. The surgical robot may have a device resonator in its base 1816, neck 1802, main structure 1808, and the like for capturing oscillating magnetic energy generated by a source. In some embodiments the robot may be wirelessly powered from a source 1814 that is integrated, attached, or next to the operating bed.

Figure 19:
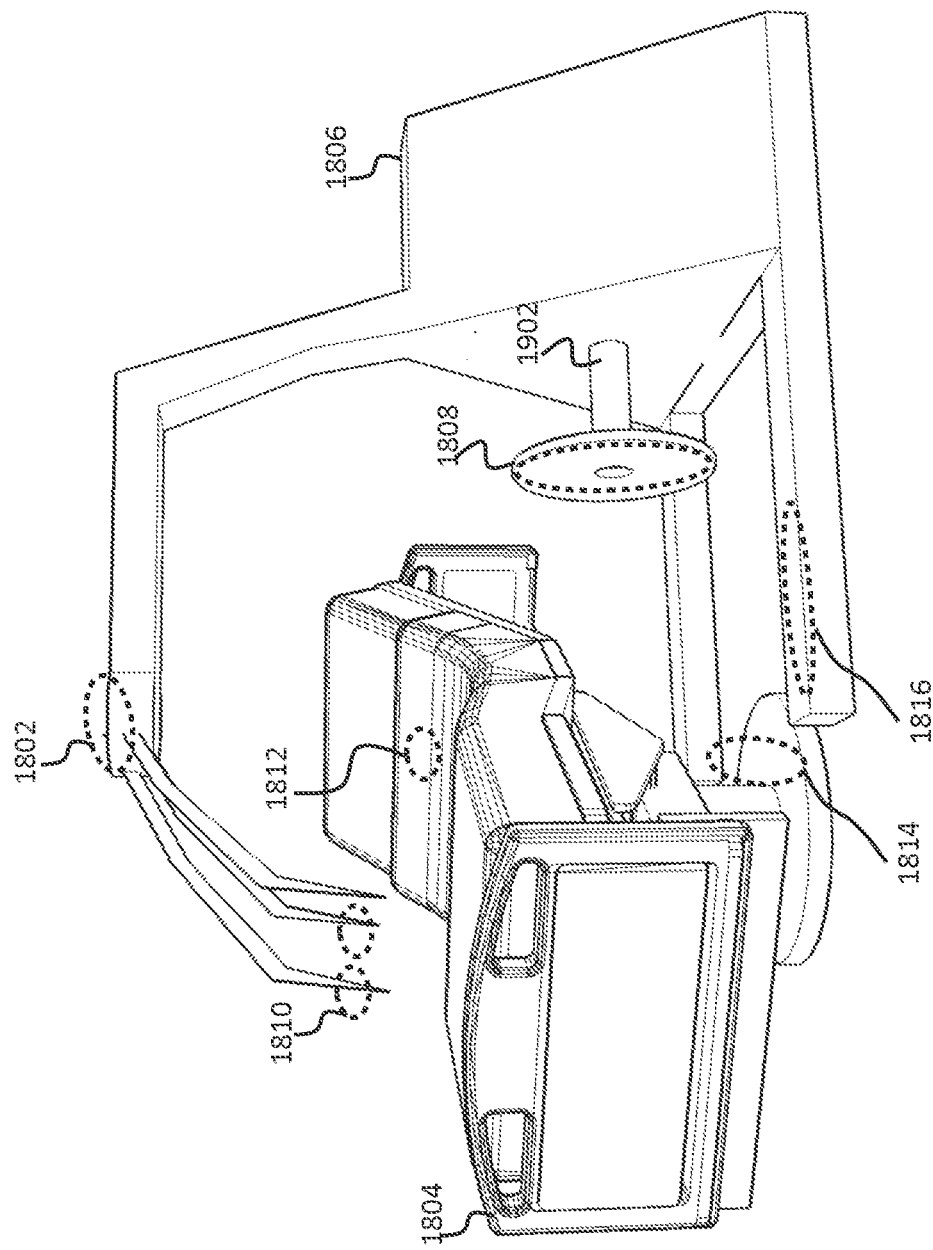
FIG. 19 is an embodiment of a surgical robot and a hospital bed with wireless energy sources and devices.

In some embodiments the source resonator or the device resonator may be mounted on an articulating arm, or a moving or configurable extension as depicted in FIG. 19. The arm or moving extension 1902 may be configured to respond to positional changes of the robot, power demands, or efficiency of the wireless power transfer to reposition the source or the device to ensure that adequate levels of power are delivered to the robot. In some embodiments the movable source or device may be moved manually by an operator or may be automatic or computerized and configured to align or to maintain a specific separation range or orientation between the source and the device.

In embodiments the movable arm or extension may be used in situations or configurations where there may be a positional offset, mismatch, later offset, or height offset between the source and the device. In embodiments the movable arm that houses or is used to position the source or device resonator may be computer controlled and may autonomously position itself to obtain the best power transfer efficiency. The arm, for example, may move in all direction scanning the most efficient configuration or position and may use learning or other algorithms to fine tune its position and alignment. In embodiments the controller may use any number of measurements from the sensor to try to align or seek the best or most efficient position including, but limited to, impedance, power, efficiency, voltage, current, quality factor, coupling rate, coupling coefficient measurements, and the like.

In other embodiments the surgical robot may use wireless power transfer to power motors, sensors, tools, circuits, devices, or systems of the robot, that are manipulated by the robot, or that are integrated into the robot. For example, many surgical robots may have complex appendages that have multiple degrees of freedom of movement. It may be difficult to provide power along or through the various joints or moving parts of the appendages due to bulkiness, inflexibility, or unreliability of wires.

Likewise, powering of the various tools or instruments necessary for a procedure may pose reliability and safety problems with power connections and connectors in the presence of body fluids. A surgical robot may utilize one or more source resonator 1802 and one or more device resonators 1810, 1812 located in the appendages or tools to power motors, electronics, or devices to allow movement of the appendages or powering of tools, cameras, and the like that the robot manipulates which may be inside, or outside of a patient. The power may be transferred wirelessly without any wires regardless of the articulation or rotation of the appendages and may increase the degrees or articulation capability of the appendages. In some embodiments the sources may be integrated into the robot and powered by the robot that may receive its own power wirelessly or from a wired connection. In some embodiments the source powering the appendages and the tools may be mounted on the operating bed, under the bed, or next to the patient.

As those skilled in the art will appreciate, the systems described and shown in the figures are specific exemplary embodiments and systems may utilize any one of many different robot devices of various shapes and capabilities, tools, and the like. Likewise the source may be mounted on any number of objects of various dimensions depending on the application and use of the robot. The source may be mounted on the operating room bed or pedestal as shown in the FIG. 18. In other embodiments a source may be mounted in the floor, walls, ceilings, other devices, and the like.

Wireless power transfer may be used to power or recharge movable equipment such as an IV or drug delivery racks or computer stands. Such stands or racks are often repositioned temporarily or moved from one location to another with a patient. The electronic devices attached to these racks often have battery backup allowing them to operate for a period of time without a direct electrical connection such that they can be moved or repositioned and maintain their functionality. However, every time a traditional rack is moved or repositioned it needs to be unplugged and plugged back into an outlet for recharging or powering and the cable must be wound or untangled from other cables.

Figure 20B:
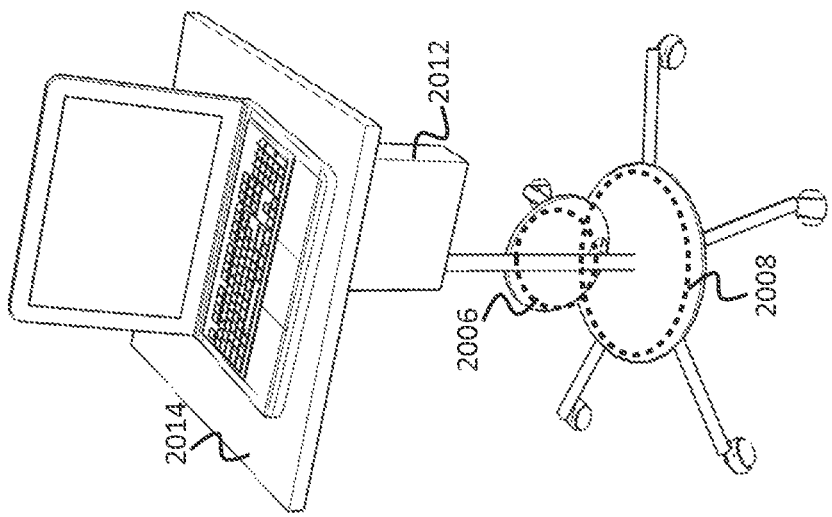
FIG. 20B is a computer cart with a wireless energy transfer resonator.
Figure 20A:
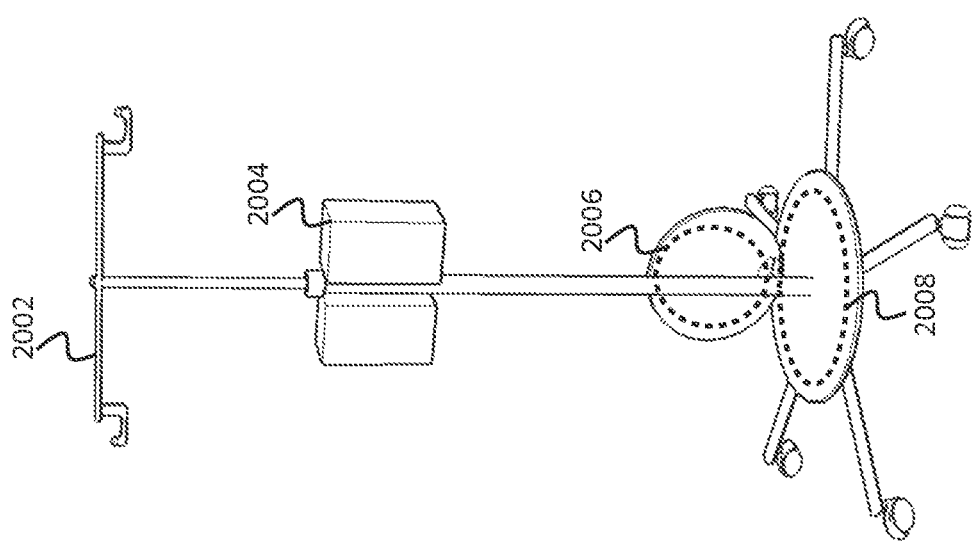
FIG. 20A is a medical cart with a wireless energy transfer resonator.

The problems with traditional movable wired drug delivery, patient monitoring, or computer racks may be overcome by integrating a wireless power transfer system to the devices. For example, sample embodiments of a drug delivery rack and a computer rack are depicted in FIG. 20A and FIG. 20B. Device resonators 2008, 2006 and power and control circuitry may be integrated or attached to the base or the body of the rack or the supporting structure allowing wireless power transfer from a source resonator mounted into the floor, wall, charging station, or other objects. To be charged or powered the rack 2002 or stand 2014 may be positioned in the proximity of the source, within a meter distance of the source, or within a foot separation of the source. The wireless power transfer enabled rack and the electrical equipment does not require plugging or unplugging or cable management. The wireless power transfer enabled rack or electrical equipment may be powered by positioning the rack or electrical equipment in a specific area of a room or in proximity to the source that may be integrated into the floor, carpet, walls, baseboard, other equipment and the like. In this configuration, for example, a device or rack that may is only used for short period of time to measure or diagnose a patient may be moved from the charging location and brought anywhere close to the patient to take a measurement and moved back into the charging location without requiring precise positioning or plugging or unplugging of the equipment.

In some embodiments the device capturing wireless energy may require additional electric and electronic components in addition to a resonator. As described herein, additional AC to DC converters, AC to AC converters, matching networks, active components may be necessary to condition, control, and convert the voltages and currents from the resonator to voltages and currents that may be usable by the device to be powered. In some devices and embodiments, the voltages and currents of the resonator may be used directly without an additional conditioning or conversion step. Surgical tools such as cauterizers, electric scalpels, and the like use oscillating high voltages to effectively cut, stimulate, or cauterize tissue. The oscillating voltages on the device resonator may be directly used to power such devices reducing their size, cost, and complexity.

For example, in some embodiments a surgical tools such as a cauterizer may be fitted with a device resonator capable of capturing magnetic energy from one or more source resonators. Depending on the inductance, quality factor, resistance, relative distance to the source resonators, power output of the source resonators, frequency, and the like the parameters of the voltages and currents on the device resonator may be enough to directly cauterize or cut tissue. Voltages of 30 or more volts with frequencies of 1 KHz to over 5 MHz may be generated on the device resonator and may be used directly as the output of the surgical tool. The oscillating electrical energy from the resonator may be directly connected to a cauterizing tip of the tool. In some embodiments the electrical energy from the resonator may be coupled to the tool through a passive electrical network of components such as resistors, capacitors, and/or inductors. In other embodiments, the electrical energy from the resonator may be coupled to the tool (e.g., cauterizing tip) directly without use of additional components prior to direct connection to the cauterizing tip, such as by a direct, wired electrical connection from two terminals of the resonator to two terminals of the tool. In some embodiments monitoring circuitry, such as a voltage sensor or other voltage or current sensing circuitry may integrated into the device resonator along with a wireless communication capability to relay the measured values to a source. The source may monitor the received current and voltage values and adjust its operating parameters to maintain a specific voltage, frequency, or current at the device or to adjust the current or voltage in response to the operator input.

A block diagram of a wirelessly powered cauterizing tool is shown in FIG. 21. A device resonator 2106 configured to capture oscillating magnetic fields generated from the source resonator 2102 may be integrated into the body 2104 of the tool. The oscillating electrical energy from the device resonator 2106 may be directly connected to the cauterizing or cutting tip 2114 of the tool. An optional voltage and current sensors 2110 may be integrated into the tool to monitor the voltage and current at the output of the resonator and wirelessly transmit the readings to the source 2102. The tool may therefore be powered completely wirelessly from the source and may be able to receive power over a distance of at least 5 cm away from the source resonator 2102.

While the invention has been described in connection with certain preferred embodiments, other embodiments will be understood by one of ordinary skill in the art and are intended to fall within the scope of this disclosure, which is to be interpreted in the broadest sense allowable by law.

All documents referenced herein are hereby incorporated by reference in their entirety as if fully set forth herein.

What is claimed is:

1. A wirelessly powered surgical device comprising:
a device resonator configured to generate an oscillating high voltage from a captured oscillating magnetic field;
a surgical device electrically coupled to the device resonator, the surgical device having a functional output directly powered by the oscillating high voltage; and
wherein the oscillating high voltage is at least 30 volts and has a frequency of at least 1 kHz.

2. The device of claim 1, wherein the oscillating high voltage is at least 50 volts rms.

3. The device of claim 1, wherein the oscillating high voltage is at least 100 volts rms.

4. The device of claim 1, wherein the functional output includes an electric scalpel powered by the oscillating high voltage.

5. The device of claim 1, wherein the functional output includes a cauterizer powered by the oscillating high voltage.

6. The device of claim 1, further comprising a voltage sensor to measure a voltage of the oscillating high voltage, thereby providing a voltage measurement.

7. The device of claim 6, further comprising a wireless communication channel to transmit the voltage measurement.

8. The device of claim 7, further comprising a source resonator, wherein the source resonator is at least 5 cm from the device resonator and generates the captured oscillating magnetic field.

9. The device of claim 8, wherein at least one of the source resonator and the device resonator has a quality factor greater than 100.

10. The device of claim 8, wherein at least one parameter of the source resonator is adjusted in response to receiving the voltage measurement from the voltage sensor.

11. The device of claim 10, wherein a frequency of the oscillating magnetic fields generated by the source resonator is adjustable in response to the voltage measurement received from the voltage sensor.

12. The device of claim 10, wherein an output power of the source resonator is adjustable in response to the voltage measurement received from the voltage sensor.

13. A wirelessly powered surgical system comprising:
a source resonator configured to generate an oscillating magnetic field;
a device resonator wirelessly coupled to the source resonator and configured to generate an oscillating high voltage energy from the oscillating magnetic field;
a surgical tool having an electrical output directly powered by the oscillating high voltage energy; and wherein the oscillating high voltage is at least 30 volts and has a frequency of at least 1 kHz.

14. The system of claim 13, wherein the surgical tool comprises an electric scalpel.

15. The system of claim 13, wherein the surgical tool comprises a tissue cauterizer.

16. The system of claim 13, further comprising a voltage sensor to measuring a voltage of the oscillating high voltage energy, thereby providing a voltage measurement.

17. The system of claim 16, further comprising a communication interface that couples the voltage sensor to the source resonator, the voltage sensor configured to transmit the voltage measurement to the source resonator.

18. The system of claim 16, wherein at least one parameter of the source resonator is adjusted in response to the voltage measurement from the voltage sensor.

* * * * *

UNITED STATES PATENT AND TRADEMARK OFFICE
CERTIFICATE OF CORRECTION

PATENT NO.        : 8,937,408 B2
APPLICATION NO.   : 13/090369
DATED             : January 20, 2015
INVENTOR(S)       : Steven J. Ganem et al.

It is certified that error appears in the above-identified patent and that said Letters Patent is hereby corrected as shown below:

On the Title Page

Page 1, Item (63)

Col. 1 (Related U.S. Application Data), Line 4, delete "and" and insert -- which is --

Page 8, Item (56)

Col. 1 (Other Publications), Line 58, delete "Linksw" and insert -- Links --

Page 9, Item (56)

Col. 1 (Other Publications), Line 34, delete "non-readiative" and insert -- non-radiative --

Col. 1 (Other Publications), Line 48, delete "Sascular" and insert -- Vascular --

Col. 1 (Other Publications), Line 52, delete "Supples" and insert -- Supplies --

Col. 2 (Other Publications), Line 23, delete "propogation" and insert -- propagation --

Col. 2 (Other Publications), Line 60, delete "NewScientistsTech.com" and insert -- NewScientistTech.com --

Page 10, Item (56)

Col. 1 (Other Publications), Line 17, delete "Weireless" and insert -- Wireless --

Col. 2 (Other Publications), Line 26, delete "Photomic-Crystal" and insert -- Photonic-Crystal --

Signed and Sealed this
Fifth Day of May, 2015

Michelle K. Lee
*Director of the United States Patent and Trademark Office*